(12) United States Patent
deLong

(10) Patent No.: US 7,074,942 B2
(45) Date of Patent: Jul. 11, 2006

(54) 2-DECARBOXY-2-PHOSPHINICO PROSTAGLANDIN DERIVATIVES AND METHODS FOR THEIR PREPARATION AND USE

(75) Inventor: Mitchell Anthony deLong, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 41 days.

(21) Appl. No.: 11/035,602

(22) Filed: Jan. 14, 2005

(65) Prior Publication Data
US 2005/0124587 A1    Jun. 9, 2005

Related U.S. Application Data

(62) Division of application No. 09/633,180, filed on Aug. 4, 2000, now Pat. No. 6,894,175.

(60) Provisional application No. 60/158,637, filed on Oct. 8, 1999, provisional application No. 60/148,042, filed on Aug. 4, 1999.

(51) Int. Cl.
  *C07F 9/06* (2006.01)
  *C07F 9/00* (2006.01)
(52) U.S. Cl. ........................ 549/222; 559/19
(58) Field of Classification Search ............... 549/222; 559/19
  See application file for complete search history.

(56) References Cited

U.S. PATENT DOCUMENTS

| | | | |
|---|---|---|---|
| 3,435,053 A | 3/1969 | Beal et al. |
| 3,524,867 A | 8/1970 | Beal et al. |
| 3,598,858 A | 8/1971 | Bergstrom et al. |
| 3,691,216 A | 9/1972 | Bergstrom et al. |
| 3,706,789 A | 12/1972 | Bergstrom et al. |
| 3,776,938 A | 12/1973 | Bergstrom et al. |
| 3,776,939 A | 12/1973 | Bergstrom et al. |
| 3,839,409 A | 10/1974 | Bergstrom et al. |
| 3,852,337 A | 12/1974 | Bergstrom et al. |
| 3,882,241 A | 5/1975 | Pharriss |
| 3,882,245 A | 5/1975 | DuCharme |
| 3,896,156 A | 7/1975 | Beal et al. |
| 3,928,588 A | 12/1975 | Robert |
| 3,966,792 A | 6/1976 | Hayashi et al. |
| 3,984,455 A | 10/1976 | Beal et al. |
| 4,011,262 A | 3/1977 | Hess et al. |
| 4,024,179 A | 5/1977 | Bindra et al. |
| 4,061,671 A | 12/1977 | Beck et al. |
| 4,073,934 A | 2/1978 | Skuballa et al. |
| 4,089,885 A | 5/1978 | Husbands |
| 4,123,441 A | 10/1978 | Johnson |
| 4,128,720 A | 12/1978 | Hayaski et al. |
| 4,158,667 A | 6/1979 | Axen |
| 4,171,331 A | 10/1979 | Biddlecom et al. |
| 4,225,507 A | 9/1980 | Sih |
| 4,225,508 A | 9/1980 | Sih |
| 4,284,646 A | 8/1981 | Vorbruggen et al. |
| 4,489,092 A | 12/1984 | Vorbruggen et al. |
| 4,499,293 A | 2/1985 | Johnson et al. |
| 4,621,100 A | 11/1986 | Lund et al. |
| 4,704,386 A | 11/1987 | Mueller |
| 4,889,845 A | 12/1989 | Ritter et al. |
| 5,063,057 A | 11/1991 | Spellman et al. |
| 5,219,885 A | 6/1993 | Frolich et al. |
| 5,280,018 A | 1/1994 | Ritter et al. |
| 5,340,813 A | 8/1994 | Klein et al. |
| 5,422,371 A | 6/1995 | Liao et al. |
| 5,464,868 A | 11/1995 | Frolich et al. |
| 5,508,303 A | 4/1996 | Isogaya et al. |
| 5,516,652 A | 5/1996 | Abramovitz et al. |
| 5,567,079 A | 10/1996 | Felder |
| 5,576,315 A | 11/1996 | Hallinan et al. |
| 5,578,640 A | 11/1996 | Hanson |
| 5,578,643 A | 11/1996 | Hanson |
| 5,605,814 A | 2/1997 | Abramovitz et al. |
| 5,605,931 A | 2/1997 | Hanson |
| 5,658,897 A | 8/1997 | Burk |
| 5,663,203 A | 9/1997 | Ekerdt et al. |
| 5,670,506 A | 9/1997 | Leigh et al. |
| 5,681,850 A | 10/1997 | Frolich et al. |
| 5,703,108 A | 12/1997 | Cameron et al. |
| 5,719,140 A | 2/1998 | Chandrakumar et al. |
| 5,759,789 A | 6/1998 | Abramovitz et al. |
| 5,770,759 A | 6/1998 | Ueno et al. |
| 5,792,851 A | 8/1998 | Schuster et al. |
| 5,834,498 A | 11/1998 | Burk |
| 5,840,847 A | 11/1998 | Abramovitz et al. |
| 5,869,281 A | 2/1999 | Abramovitz et al. |
| 5,877,211 A | 3/1999 | Woodward |
| 5,885,766 A | 3/1999 | Mahe et al. |

(Continued)

FOREIGN PATENT DOCUMENTS

BE    746615 A    7/1970

(Continued)

OTHER PUBLICATIONS

DeLong MA Prostaglandin receptor ligands: Recent patent activity. *IDrugs* 2000 3(9); 1039-1052.

(Continued)

*Primary Examiner*—Deborah C. Lambkin
(74) *Attorney, Agent, or Firm*—James Derry; Jay A. Krebs

(57) ABSTRACT

2-Decarboxy-2-phosphinico prostaglandin derivatives are disclosed. These derivatives comprise a modified α-chain and an Ω-chain bonded to a ring structure. The modified α-chain has a 2-decarboxy-2-phosphinico group. The derivatives can be used to treat a variety of pharmaceutical and cosmetic conditions.

4 Claims, No Drawings

U.S. PATENT DOCUMENTS

| | | | |
|---|---|---|---|
| 5,885,974 A | 3/1999 | Danielov |
| 5,889,052 A | 3/1999 | Klimko et al. |
| 5,892,099 A | 4/1999 | Maruyama et al. |
| 5,958,723 A | 9/1999 | Abramovitz et al. |
| 5,972,965 A | 10/1999 | Taniguchi et al. |
| 5,973,002 A | 10/1999 | Frolich et al. |
| 5,977,173 A | 11/1999 | Wos et al. |
| 5,985,597 A | 11/1999 | Ford-Hutchinson et al. |
| 5,990,346 A | 11/1999 | Kataoka et al. |
| 5,994,397 A | 11/1999 | Selliah et al. |
| 6,013,823 A | 1/2000 | Mamarella et al. |
| 6,025,375 A | 2/2000 | Taniguchi et al. |
| 6,025,392 A | 2/2000 | Selliah et al. |
| 6,030,959 A | 2/2000 | Tremont et al. |
| 6,030,999 A | 2/2000 | Stjernschantz et al. |
| 6,031,001 A | 2/2000 | Stjernschantz et al. |
| 6,031,079 A | 2/2000 | Ford-Hutchinson et al. |
| 6,037,364 A | 3/2000 | Burk |

FOREIGN PATENT DOCUMENTS

| | | |
|---|---|---|
| DE | 1617477 A1 | 1/1970 |
| DE | 2460990 A1 | 7/1976 |
| EP | 249194 A2 | 12/1987 |
| EP | 648488 A1 | 4/1995 |
| EP | 911321 A2 | 4/1999 |
| EP | 925787 A1 | 6/1999 |
| EP | 947500 A1 | 10/1999 |
| EP | 970697 A1 | 1/2000 |
| EP | 1008588 A1 | 6/2000 |
| EP | 1016660 A1 | 7/2000 |
| FR | 2108027 A1 | 5/1972 |
| FR | 2730811 A1 | 8/1996 |
| GB | 1251750 A | 10/1971 |
| GB | 1285371 A | 8/1972 |
| GB | 1285372 A | 8/1972 |
| GB | 1456512 A | 11/1976 |
| GB | 1456513 A | 11/1976 |
| GB | 1456514 A | 11/1976 |
| GB | 2048254 A | 12/1980 |
| GB | 2330307 A | 4/1999 |
| JP | 49-101356 A2 | 9/1974 |
| JP | 49-102647 A2 | 9/1974 |
| JP | 61-218510 A2 | 9/1986 |
| JP | 3-83925 | 4/1991 |
| JP | 3-83926 | 4/1991 |
| JP | 4-300833 A2 | 10/1992 |
| JP | 9-295921 A2 | 11/1997 |
| JP | 10-287532 A2 | 10/1998 |
| WO | WO 86/00616 A1 | 1/1986 |
| WO | WO 94/08585 A1 | 4/1994 |
| WO | WO 95/00552 A1 | 1/1995 |
| WO | WO 95/11003 A1 | 4/1995 |
| WO | WO 95/11033 A1 | 4/1995 |
| WO | WO 95/19964 A1 | 7/1995 |
| WO | WO 96/10407 A1 | 4/1996 |
| WO | WO 97/09049 A2 | 3/1997 |
| WO | WO 97/15319 A1 | 5/1997 |
| WO | WO 97/23223 A1 | 7/1997 |
| WO | WO 97/23225 A1 | 7/1997 |
| WO | WO 97/23226 A1 | 7/1997 |
| WO | WO 97/29735 A1 | 8/1997 |
| WO | WO 97/39754 A1 | 10/1997 |
| WO | WO 98/00100 A1 | 1/1998 |
| WO | WO 98/12175 A1 | 3/1998 |
| WO | WO 98/13016 A1 | 4/1998 |
| WO | WO 98/19680 A1 | 5/1998 |
| WO | WO 98/20880 A2 | 5/1998 |
| WO | WO 98/20881 A1 | 5/1998 |
| WO | WO 98/21180 A1 | 5/1998 |
| WO | WO 98/21181 A2 | 5/1998 |
| WO | WO 98/21182 A2 | 5/1998 |
| WO | WO 98/27976 A1 | 7/1998 |
| WO | WO 98/28264 A1 | 7/1998 |
| WO | WO 98/33497 A1 | 8/1998 |
| WO | WO 98/39293 A2 | 9/1998 |
| WO | WO 98/50024 A1 | 11/1998 |
| WO | WO 98/53809 A1 | 12/1998 |
| WO | WO 98/57930 A1 | 12/1998 |
| WO | WO 98/57942 A1 | 12/1998 |
| WO | WO 98/58911 A2 | 12/1998 |
| WO | WO 99/02165 A1 | 1/1999 |
| WO | WO 99/12550 A1 | 3/1999 |
| WO | WO 99/12551 A1 | 3/1999 |
| WO | WO 99/12895 A1 | 3/1999 |
| WO | WO 99/12896 A1 | 3/1999 |
| WO | WO 99/12897 A1 | 3/1999 |
| WO | WO 99/12898 A1 | 3/1999 |
| WO | WO 99/12899 A1 | 3/1999 |
| WO | WO 99/19300 A1 | 4/1999 |
| WO | WO 99/21562 A1 | 5/1999 |
| WO | WO 99/22731 A1 | 5/1999 |
| WO | WO 99/25357 A1 | 5/1999 |
| WO | WO 99/25358 A1 | 5/1999 |
| WO | WO 99/30675 A1 | 6/1999 |
| WO | WO 99/30718 A2 | 6/1999 |
| WO | WO 99/32441 A1 | 7/1999 |
| WO | WO 99/32640 A1 | 7/1999 |
| WO | WO 99/32641 A1 | 7/1999 |
| WO | WO 99/33794 A1 | 7/1999 |
| WO | WO 99/47497 A2 | 9/1999 |
| WO | WO 99/50241 A1 | 10/1999 |
| WO | WO 99/50242 A1 | 10/1999 |
| WO | WO 99/61029 A1 | 12/1999 |
| WO | WO 99/64621 A1 | 12/1999 |
| WO | WO 99/65303 A1 | 12/1999 |
| WO | WO 99/65527 A1 | 12/1999 |
| WO | WO 00/02450 A1 | 1/2000 |
| WO | WO 00/03736 A1 | 1/2000 |
| WO | WO 00/03980 A1 | 1/2000 |
| WO | WO 00/04898 A1 | 2/2000 |
| WO | WO 00/04899 A1 | 2/2000 |
| WO | WO 00/07627 A2 | 2/2000 |
| WO | WO 00/09557 A1 | 2/2000 |
| WO | WO 00/13664 A1 | 3/2000 |
| WO | WO 00/15608 A1 | 3/2000 |
| WO | WO 00/16760 A2 | 3/2000 |
| WO | WO 00/51979 A1 | 9/2000 |
| WO | WO 00/51980 A1 | 9/2000 |

OTHER PUBLICATIONS

Negishi, M.; Sugimoto, Y.; Ichikawa, A.; Molecular mechanisms of diverse actions of prostanoid receptors. *Biochimica et Biophysica Acta 1259* 1995 109-120.

Collins, PW; Djuric SW; Synthesis of therapeutically useful prostaglandin and prostacyclin analogs *Chem. Rev.* 1993 93 1533-1564.

Coleman RA, Kennedy I, Humphrey PPA, Bunce K, Lumley P Prostanoids and their receptors. *Comprehensive Medicinal Chemistry*, vol. 3; Membranes and Receptors. 1990 643-714.

Coleman RA, Smith WL, Narumiya S *Pharmacol. Rev.* 1994 46 205-229.

Albert Alm, MD The Potential of prostaglandin derivates in glaucoma therapy; Prostaglandins and derivates *Current Opinion in Ophthamology* 1993 4(11) 44-50.

Coleman RA, Smith WL, Narumia S Classification of prostanoid receptors: properties, distribution, and structure of the receptors and their subtypes *Pharmacological Reviews* 1994 46(2) 205-229.

Kiriyama M, Ushikubi F, Kobayashi T, Hirata M, Sugimoto Y, Narumiya S Ligand binding specificities of the eight types and subtypes of the mouse prostanoid receptors expressed in Chinese hamster ovary cells *British Journal of Pharmacology* 1997 (122) 217-224.

Funk CD, Furci L, Fitzgerald GA, Cloning and expression of a cDNA for the human prostaglandin E receptor $EP_1$ subtype* *Journal of Bioogical Chemistry* 1993 (268) 26767-26772.

Abramovitz M, Boie Y, Nguyen T, Rushmore TH, Bayne MA, Metters KM, Slipetz DM and Grygorczyk R Cloning and expression of a cDNA for the human prostanoid FP receptor *Journal of Bioogical Chemistry* 1994 269 2632-2636.

Ichikawa EA, Sugimoto Y, Negishi M Molecular aspects of the structures and functions of the prostaglandin E receptors *Journal of Lipid Mediators Cell Signalling* 14 1996 83-87.

Krauss AHP, Woodward DF, Gibson LL, Protzman CE, Williams LS, Burk RM, Gac TS, Roof MB, Abbas F, Marshall K, Senior J Evidence for human thromboxane receptor heterogeneity using a novel series of 9,11-cyclic carbonate derivatives of prostaglandin-$F_2$-*alpha British Journal of Pharmacology* 1996 117(6) 1171-1180.

Corsini A, Folco GC, Fumagalli R, Nicosia S, Noe MA, Oliva D (5Z)-Carbacyclin discriminates between prostacyclin receptors coupled to adenylate cyclase in vascular smooth muscle and platelets *British Journal of Pharmacology* 1987 90 255-261.

Woodward DF, Gil DW, Chen J, Burk RM, Kedzie KM, Krauss AH-P Emerging evidence for additional prostanoid receptor subtypes *Cur. Top. Pharmacol.* 1998 4 153-162.

Woodward DF, Madhu C, Rix P, Kharlamb A Studies on the ocular effects of a pharmacologically novel agent prostaglandin $F_2$ alpha 1-$OCH_3$ (AGN 191129) *N-S Archives of Pharmacology* 1998 358 (1). p. 1713.

Orlicky DJ Negative regulatory activity of a prostaglandin $F_{2a}$ receptor associated protein (FPRP) *Prostaglandins, Leukotrienes and Essential Fatty Acids* 1996 54(4) 247-259.

Jakobsson PJ, Morgenstern R, Mancini J, Ford-Hutchinson A, Persson B Membrane-associated proteins in eicosanoid and glutathione metabolism (MAPEG)-A widespread protein superfamily *Am. J. Resp. Crit. Care Med.* 2000 (161) S20-S24.

Abramovitz M, Adam M, Boie Y, Carriere MC, Denis D, Godbout C, Lamontagne S, Rochette C, Sawyer N, Tremblay NM, Belley M, Gallant M, Dufresne C, Gareau Y, Ruel R, Juteau H, Labelle M, Ouimet N, Metters KM The utilization of recombinant prostanoid receptors to determine the affinities and selectivities of prostaglandins and related analogs *Biochimica et Biophysica Acta* 2000 1483 (2) 285-293.

Ruel R, Lacombe P, Abramovitz M, Godbout C, Lamontagne S, Rochette C, Sawyer N, Stocco R, Tremblay NM, Metters KM, Labelle M New class of biphenylene dibenzazocinones as potent ligands for the human $EP_1$ prostanoid receptor *Bioorganic & Medicinal Chemistry Letters.* 1999 (9) 2699-2704.

Hallinan EA, Hagen TJ, Tsymbalov S, Husa RK, Lee AC, Staplefield A, Savage MA Aminoacetyl moiety as a potential surrogate for diacylhydrazine group of SC-51089, a potent $PGE_2$ antagonist, and its analogs *J. Med. Chem.* 1996 39 609-613.

Pharmaprojects No. 6321.

Maruyama T, Koketsu M, Yamamoto H, Yamamoto K, Yamamoto L T, Hayashida K I, Ohuchida S, Kondo K $EP_1$ receptor antagonists suppress tactile allodynia in rats *Prostaglandins Lipid Mediat.* 1999 59 217.

ADIS, ADISINSIGHT: ZD-6416 Mar. 27, 2000.

Ueda K, Saito A, Nakano H, Aoshima M, Yokota M, Muraoka R, Iwaya T Brief clinical and laboratory observations: Cortical hyperostosis following long-term administration of prostaglandin $E_1$ in infants with cyanotic congenital heart disease *The Journal of Pediatrics* 1980 97 834-836.

Shih MS, Norridin RW $PGE_2$ induces regional remodeling changes in Haversian envelope: A histomorphometric study of fractured ribs in beagles *Bone and Mineral* 1986 (1) 227-234.

Mori S, Jee WSS, Li XJ, Chan S, Kimmel DB Effects of prostaglandin $E_2$ on production of new cancellous bone in the axial skeleton of ovariectomized rats *Bone* 1990 (11) 103-113.

Chyun YS, Raisz LG Stimulation of bone formation by prostaglandin $E_2$ *Prostaglandins* 1984 (27) 97-103.

Norridin RW, Jee WSS, High WB The role of prostaglandins in bone in vivo *Prostaglandins, Leukotrienes and Essential Fatty Acids* 1990 (41) 139-149.

Roof SL, deLong MA, Charest RP mRNA expression of prostaglandin receptors $EP_1$, $EP_2$, $EP_3$ and $EP_4$ in human osteoblast-like cells and 23 human tissues *Journal Bone Min. Res.* 1996 (11) S337.

Hartke JR, Jankowsky ML, deLong MA, Soehner ME, Jee WSS, Lundy MW Prostanoid FP agonists buld bone in the ovariectomized rat *J. Bone Min. Res.* 1999 (14) T326, p. S207.

Lundy MW, deLong MA, Combs KS, Gross GJ, Soehner ME, Hartke JR Restoration of cancellous architecture and increased bone strength in aged osteopenic rats treated with fluprostenol *J. Bone Min. Res.* 1999 1(4) SA368, p. S401.

Wang Y, Wos JA, Dirr MA, Soper DL, deLong MA, Mieling G, De B, Amburgey J, Suchanek E, Taylor CJ The design and synthesis of 13, 14- dihydro prostaglandin $F_1$a analogs as potent and selective ligands for the human FP receptor. *J. Med. Chem.* 2000 43(5) 945-952.

Sakuma Y, Tanaka K, Suda M, Yasoda A, Natsui K, Tanaka I, Ushikubi F, Narumiya S, Segi E, Sugimoto Y, Ichikawa A, Nakao K Crucial involvement of the $EP_4$ subtype of prostaglandin E receptor in osteoclast formation by proinflammatory cytokines and lipopolysaccharide *J. Bone and Mineal Research.* 2000 15(2) 218-227.

DelToro F Jr, Sylvia VL, Schubkegel SR, Campos R, Dean DD, Boyan BD, Schwartz Z Characterization of prostaglandin $E_2$ receptors and their role in 24,25-$(OH)_2D_3$-mediated effects on resting zone chondrocytes *J. Cell. Physiol.* 2000 182(2) 196-208.

Narumiya S Roles of prostanoids in health and disease, lessons from receptor-knockout mice *Int. Congr. Ser.* 1999 1181 261-269.

Audoly LP, Tilley J, Goulet J, Key M, Nguyen M, Stock JL, McNeish JD, Koller BH, Coffman TM Identification of specific EP receptors responsible for the hemodynamic effects of $PGE_2$ *Am. J. Physiol.* 1999 46(3) H924-930.

Vayssairat M Preventive effect of an oral prostacyclin analog, beraprost sodium, on digital necrosis in systemic sclerosis *J. Rheumatol.* 1999 26(10) 2173-2178.

Murakami T, Sawada K, Taneda K, Hayashi M, Katsuura Y, Tanabe H, Kiyoki M, and Araki H. Effect of isocarbacyclin methyl ester incorporated in lipid microspheres on experimental models of peripheral obstructive disease. *Arzheim.-Forsh./Drug Res.* 1995 45(II) Nr. 9, p. 991-994.

Hall A, Smith WHT Clinprost Teijin *Current Opinion in Cardiovascular, Pulmonary & Renal Investigations Drugs* 1999 1(5) 605-610.

Terada N, Yamakoshi T, Hasegawa M, Tanikawa H, Nagata H, Maesako KI, Konno A Effect of a thromboxane $A_2$ receptor antagonist, ramatroban (BAY U3405), on inflammatory cells, chemical mediators and non-specific nasal hyperreactivity after allergen challenge in patients with perennial allergic rhinitis *Allergology Internatioanl.* 1998 47(1), 59-67.

Miyamoto T, Takishima T A comparison in the efficacy and safety between ramatroban (BAY u 3405) and ozagrel-HCl for bronchial asthma: a phase III, multi-center, randomized, double-blind, group comparative study *Rinsho Iyaku.* 1997 13 599-639.

Rampton DS, Carty E, Van Nueten L Anti-inflammatory profile in vitro of ridogrel, a putative new treatment for inflammatory bowel disease *Gastroenterology* 1999 (116)G3477, p. 801.

McCullough PA Ridogrel (Janssen) *Current Opinion in Anti-inflammatory & Immunomodulatory Investigational Durgs* 1999 1(3), 265-276.

Inoue H Thromboxane $A_2$ receptor antagonists *Farumashia* 1996 32(10) 1221-1225.

Lardy C, Rousselot C, Chavernac G, Depin JC, Guerrier D Antiaggregant and antivasospastic properties of the new thromboxane $A_2$ receptor antagonist sodium 4-[[1-[[[(4-chlorophenyl) sulfonyl]amino] methyl] cyclopentyl] methyl] benzeneacetate Arzneim.-Forsch./Drug Res. 1994 44(11) 1196-1202.

Cayatte AJ, Du Y, et al The thromboxane $A_2$ receptor antagonist, S18886, decreases atherosclerotic lesions and serum intracellular adhesion molecule-1 in the Apo E knockout mouse *Circulation.* 1998 98 115.

Verbeuren T, Descombes JJ The TP-receptor antagonist S 18886 unmasks vascular relaxation and potentiates the antiplatelet action of $PGD_2$ *Thromb. Haemostasis.* 1997 693.

Yoshida K, Sato H Synthesis and pharmacological activities of the new $TXA_2$ receptor antagonist Z-335 and related compounds *AFMC* 1995 95 53.

Kerstetter JR, Brubaker RF, Wilson SE, Kullerstrand LJ Prostaglandin $F_2$ *alpha* -1-isopropylester lowers intraocular pressure without decreasing aqueous humor flow *American Journal of Ophthalmology* 1988 105 30-34.

AGN-192024 *Pharmaprojects* Oct. 1999 HB4 S1G.

VanDenburgh AM, Laibovitz RA, Felix C A one-month dose-response study of AGN 192024, a novel antiglaucoma agent, in patients with elevated intraocular pressure *IOVS,* 1999 40 (4) 4373-B176, p. S830.

Chen J, Woodward DF, Gil DW, Messier T, Marshall K, Senior J AGN 191129: A neutral prostaglandin F-2 *alpha* ($PGF_{2a}$) analog that lacks the mitogenic and uterotonic effects typical of FP receptor agonists *IOVS.* 1999 40 3562-B420, p. S675.

Sharif NA, Davis TL, Williams GW $^3H$ AL-5848 ([$^3H$]9 *beta*-(+)-Fluprostenol). Carboxylic acid of travoprost (AL-6221), a novel FP prostaglandin to study the pharmacology and autoradiographic localization of the FP receptor *J. Phar. Pharmacol.* 1999 51(6) 685-94.

Garadi R, Silver L, Landry T, Turner FD Travoprost: A new once-daily dosed prostaglandin for the reduction of elevated intraocular pressure *IOVS.* 1999 40(4) 4378-B181, p. S831.

Dean TR, Barnes GE, Li B, Chandler ML Improvement of optic nerve head blood flow after one-week topical treatment with travoprost (AL-06221) in the rabbit *IOVS.* 1999 40(4) 2688-B563, p. S509.

Griffin BW, Klimko P, Crider JY, Sharif NA Al-8810: a novel prostaglandin $F_{2a}$ analog with selective antagonist effects at the prostaglandin $F_{2a}$ (FP) receptor *J. Pharmacol. Exp. Ther.* 1999 290(3) 1278-1284.

Woodward DF, Bogardus AM, Donello JE, Fairbairn CE, Gil DW, Kedzie KM, Burke JA, Kharlamb A, Runde E Molecular characterization and ocular hypotensive properties of the prostanoid $EP_2$ receptor *J. Oc. Pharm. Therap.* 1995 11(3) 447-454.

Karim SMM, Adaikin PG, Kottegoda SR Prostaglandins and human respiratory tract smooth muscle: Structure activity relationship *Adv. Prostaglandin Thromboxane Res.* 1980 7 969-980.

Maw GN Pharmacological therapy for the treatment of erectile dysfunction *Annu. Rep. Med. Chem.* 1999 34 71-80.

Anon. Alprostadil (nexmed): Alprox-TD, Befar, Femprox, prostaglandin $E_1$ (nexmed) *Drugs R&D* 1999 2(6) 413-414.

Matsumura H Prostaglandins and sleep *Saishin No to Shinkei Kagaku Shirizu* 1998 10 79-89.

Tomita Y, Maeda K, Tagami H Melanocyte-stimulating properties of arachidonic acid metabolites: possible role in postinflammatory pigmentation *Pigm. Cell Res.* 1992 5(5, Pt. 2) 357-61.

Huang A, Katori M, Kawamura M, Li B, Harada Y Different modes of inhibition of increase in cytosolic calcium and aggregation of rabbit platelets by two thromboxane $A_2$ antagonists *Asia Pacific Journal of Pharmacology* 1994 9 163-171.

Flisiak R, Prokopowicz D Effect of misoprostol on the course of viral hepatitis B *Hepato-Gastroenterology* 1997 44(17) 1419-1425.

Mihele D, Cristea E, Mihele D, Cocu F The testing of the hepatoprotective action of some new synthetic prostaglandins *Farmacia (Bucharest)* 1999 47(5) 43-58.

Vengerovsky AI, Baturina NO, Saratikov AS Hepatoprotective action of prostaglandins *Eksp. Klin. Farmakol.* 1997 60(5) 78-82.

Clissold D The potential for prostaglandin pharmaceuticals *Spec. Publ.—R. Soc. Chem.* 1999 244 115-129.

Zimbric, M.L.; Cappas, A.A.; Uno, H.; Albert, D.M.; Effects of Latanoprost of Hair Growth in the Bald Scalp of Stumptailed Macaques. *IOVS,* 1999 (40) 3569-B427, p. S676.

Voss, N.G.; Lindstrom, M.J.; Zimbric, M.L.; Albert, D.M.; Uno, H Induction of Anagen Hair Growth in Telogen Mouse Skin by Topical Latanoprost Application . *IOVS,* 1999 (40) 3570-B428, p. S676.

Johnstone, M.A Hypertrichosis and increased pigmentation of eyelashes and adjacement hair in the region of the ipsilateral eyelids of patients treated with unilateral topical latanoprost. *American Journal of Ophthalmology* 1997 544-547.

Eisenberg DL, Camras CB A preliminary risk-benefit assessment of latanoprost and unoprostone in open-angle glaucoma and ocular hypertension. *Drug Safety* 1999 20(6), 505-514.

Millikan LE, Treatment of Alopecia. *Journal Clinical Pharmocology* 1987 (27) No. 9, p. 715.

Depperman, W.H. jr.; Up-to-date scalp tonic. *New England Journal of Medicine*, (Nov. 12, 1970) 283 (20) 1115.

Johnstone MA Brief latanoprost Rx induces hypertrichosis. *Iovs,* (Mar. 15, 1998) vol. 39, No. 4, p. S258).

Al-Sereiti, M.R.; Abu-Amer, K.M.; Sen, P.; Al-Fateh University of Medical Sciences, Tripoli, Libya, Indian J. Pharmacology of rosemary (*rosmarinus officinalis linn.*) and its therapeutic potentials *Exp. Biol.* (1999), 37(2), 124-130.

Olsen EA, and Delong E. Transdermal viprostol in the treatment of male pattern baldness. *Journal of American Acad. Dermatology*, (1990) 23 (3 Part 1), 470-472.

Houssay AB, Arias NH, Davison TA, and Epper CE Effects of prostaglandins upon hair growth in mice. *Acta Physiol. Lat. Am.* (1976), 266(3), 186-191.

Millikan LE Treatment of male pattern baldness. *Drug Therapy* 1989 19, No. 3, 62-73.

Roenigk HH New topical agents for hair growth. *Clinics in Dermatology* 1988 6 (4) 119-21.

Vincent JE Prostaglandin synthesis and selenium deficiency a hypothesis. *Prostaglandins*, (1974) 8 (4), 339-340.

Malkinson FD, Geng L, and Hanson W R, Prostaglandins protect against murine hair injury produced by ionizing radiation or doxorubicin. *Journal Invest. Dermatol.* (1993) 101 (1, Suppl.), 135s-137s.

Jimenez JJ, Hussein AM, and Yunis AA. Stimulated monocyte-conditioned media protect from cytosine arabinoside-induced alopecia in rat. *Clin. Res.* (38, No. 4, 973a, (1990).

Hanson, W.R.; Pelka, A.E.; Nelson, A.K.; and Malkinson, F.D; Rush Medical Center, Chicago. 16,16 dm prostaglandin 2 protects from acute radiation-induced alopecia in mice. *Clin. Res.* (36, No. 6, 906a, 1988).

Ling G, Hanson WR, Malkinson FD, 16,16 dm prostaglandin E2 protects mice from fractionated radiation-induced alopecia. *Clin. Res.* , 1988 36, No. 6, 906a.

Hanson, W.R.; Geng, L.; and Malkinson, F. D.; Loyola and Hines Medical Centers, Maywood, IL Prostaglandin-induced protection from radiation or doxorubicin is tissue specific in mice. *Journal of Investigative Dermatology*, (1996) vol. 106, No. 4, p. 858.

Geng L, Malkinson FD, Hanson WR, Misoprostol, a PGE-1 analog that is radioprotective for murine intestine and hair, induces widely different cytokinetic changes in these tissues. *Journal of Investigative Dermatology*, (1996) vol. 106, No. 4, p. 858.

Geng L, Hanson WR, Malkinson FD, Topical or systemic 16,16 dm-prostaglandin E2 or WR-2721 (WR-1065) protects mice and alopecia after fractionated irradiation. *Int. Journal Radiat. Biol.* (1992), 61(4), 533-7.

Hanson WR, Pellka AE, Nelson AK, Malkinson FD Subcutaneous or topical administration of 16,16 dimethyl prostaglandin E2 protects from radiation-induced alopecia in mice. *Int. Journal Radiat. Oncol., Biol, Phys.* (1992), 23(2), 333-7.

Hulan HW, Kramer JKG, The effect of long-chain monoenes on prostaglandin E2 synthesis by rat skin. *Lipids* (1977), 12(7), 604-9.

Hulan HW, Hunsaker WG, Kramer JKG, Mahadevan S, The development of dermal lesions and alopecia in male rats fed rapeseed oil. *Can. J. Physiol Pharmacol*, (1976) 54, (1), 1-6.

Sredni B, Xu RH, et al The protective role of the immunomodulator AS101 against chemotherapy-induced alopecia studies on human and animal models. . *Int. J. Cancer* (1996), 65 (1), 97-103.

Kvedar JC, Baden HP, Topical minoxidil in the treatment of male pattern alopecia. *Pharmacotherapy* 1987 (7) No. 6, 191-97.

Hecker M; Ullrich, V; Studies on the interaction of minoxidil with prostacyclin synthase in-vitro. *Biochem. Pharmacol.*, (1988) 37(17), 3363-3365.

Michelet JF,Commo S, Billoni N, Mahe YF, Bernard BA Activation of cytoprotective prostaglandin synthase-1 by minoxidil as a possible explanation for its hair growth-stimulation effect. *Journal of Investigative Dermatology* (1997), 108(2), 205-209.

Lachgar S, Charveron M, Bouhaddioui N, Gall Y, Bonafe JL Modulation by minoxidil and VEGF of the production of inflammatory mediators by hair follicle dermal papilla cells. *Journal Invest. Dermatol.* 1995 104, No. 1, 161.

Lachgar, S. Charverson, M.; et al; Hair dermal papilla cell metabolsm is influenced by minoxidil. *Fundam. Clin. Pharmacol.* 1997 (11, No. 2)178.

Lachgar, S. Charverson, M.; et al; Laboratoire Culture De Peau, Clinical and Bio-Clinical Research Group Dermatology, Toulouse, France. Effect of VEGF and minoxidil on the production of arachidonic acid metabolites by cultured hair, dermal papilla cells. *European Journal of Dematol.* (1996), 6(5), 365-368.

Sauk JJ, White JG, Witkop CJ Influence of prostaglandin E-1 prostaglandin E-2 and arachidonate on melanosomes in melanocytes and keratinocytes of anagen bulbs in-vitro. *Journal Invest. Dermatol*, (1975) 64(5), 332-337.

2-DECARBOXY-2-PHOSPHINICO PROSTAGLANDIN DERIVATIVES AND METHODS FOR THEIR PREPARATION AND USE

CROSS REFERENCE

This application is a divisional of U.S. application Ser. No. 09/633,180, filed Aug. 4. 2000, now U.S. Pat. No. 6,894,175 which claims priority under Title 35, United States Code §119(e) from Provisional Application Ser. No. 60/148,042, filed Aug. 4, 1999 and Provisional Application Ser. No. 60/158,637, filed Oct. 8, 1999.

FIELD OF THE INVENTION

This invention relates to prostaglandin derivatives and methods for their preparation and use. More specifically, this invention relates to 2-decarboxy-2-phosphinico prostaglandin derivatives and methods for their preparation and use.

BACKGROUND OF THE INVENTION

Prostaglandins are twenty carbon ($C_{20}$) fatty acid derivatives. Prostaglandins bind with prostaglandin receptors. These receptors, eight of which have been reported to date, are members of the superfamily of seven transmembrane domain G-coupled receptors. Prostaglandin agonists activate the receptors to which they bind, and prostaglandin antagonists inhibit the receptors to which they bind; thereby producing biological effects.

For example, four receptors couple to an increase in intracellular cAMP, and are smooth muscle relaxants. $EP_4$, DP, IP (prostacyclin) and $EP_2$ are in this category. Three receptors couple to an increase in intracellular calcium and contract smooth muscle: the $EP_1$ (see Funk C D, Furci L, Fitzgerald G A, Cloning and expression of a cDNA for the human prostaglandin receptor $EP_1$ subtype. *J. Biol. Chem.* 1995 270, 18910–18916), the FP (ligand: $PGF_{2\alpha}$) (see Abramovitz M, Boie Y, Mguyen T, Rushmore T H, Bayne M A, Metters K M, Slipetz D M and Grygorczyk R Cloning and expression of a cDNA for the human prostanoid FP receptor. *J. Biol. Chem* 1994 269 2632–2636), and the TP (thromboxane) receptors. Finally, the $EP_3$ receptor couples to a lowering of intracellular cAMP, and thus prevents relaxation of smooth muscle. Activation of this receptor blocks the forskolin-induced increase in intracellular cAMP. In addition to the gene products, alternate splicing gives rise to multiple isoforns of the $EP_3$ (eight isoforms) (see Ichikawa E A Molecular aspects of the structures and functions of the prostaglandin E receptors *J. Lipid Med. Cell Signal.* 1996 14 83–87) and the TP (two isoforms) (see Krauss A H P, Woodward D F, Gibson L L, Protzman C E, Williams L S, Burk R M, Gac T S, Roof M B, Abbas F, Marshall K, Senior J Evidence for human thromboxane receptor heterogeneity using a novel series of 9,11-cyclic carbonate derivatives of prostaglandin-F2-alpha *Br. J. Pharm.* 1996 117(6) 1171–1180). These isoforms alter the carboxy-terminal region and thus the coupling of the G-proteins, rather than the prostaglandin binding regions. Pharmacological studies have provided evidence for the existence of other subtypes of receptors (see Corsini A. Folco G C, Fumagalli R. (5Z)-Carbacyclin discriminates between prostacyclin receptors coupled to adenylate cyclase in vascular smooth muscle and platelets. *Br. J. Pharmacol.* 1987 90, 255–261) or splice variants. The evidence is particularly compelling for the DP receptor and an FP or $EP_1$ variant (Id., and see Woodward D F, Gil D W, Chen J, Burk R M, Kedzie, K M, Krauss, A H-P, Emerging evidence for additional prostanoid receptor subtypes *Cur. Top. Pharmacol.* 1998 4, 153–162; and Woodward D F, Madhu C, Rix P, Kharlamb A Studies on the ocular effects of a pharmacologically novel agent prostaglandin F2 alpha 1-OCH3 *N-S Arch. Pharm.*, 1998. 358, (1). P1713—P1713). In addition, negative regulatory proteins (see Orlicky, D J Negative regulatory activity of a prostaglandin F2a receptor associated protein (FPRP) *Prostaglandins, Leukotr. Ess. Fatty Acids* 1996 54(5) 247–259; and Jakobsson P J, Morgenstern R, Mancini J, FordHutchinson A, Persson B Membrane-associated proteins in ecosanoid and glutathione metabolism (MAPEG)-A widespread protein superfamily *Am. J. Resp. Crit. Care Med.* 2000 161, S20–S24) and active transport proteins have recently been identified.

The receptors' nomenclature describes the naturally occurring prostaglandin to which they have the highest affinity, e.g., the EP series of receptors have the highest affinity for the ligand $PGE_2$ (see Coleman R A, Smith, W L, Narumia S Classification of prostanoid receptors: properties, distribution, and structure of the receptors and their subtypes. *Pharmacol. Rev.* 1994 46, 205–229). However, all the naturally-occurring prostaglandins have some affinity for all eight of the receptors (see Kiriyama M, Ushikubi F, Kobayashi T, Hirata M, Sugimoto Y, Narumiya S Binding specificities of the prostanoid receptors. *Br. J. Pharmacol.* 1997 122 217–224).

Naturally-occurring prostaglandins include $PGE_1$ and $PGE_2$, $PGF_{2\alpha}$, prostacyclin (PGI), thromboxane and $PGD_2$. Naturally occurring prostaglandins have substituent groups at the $C_9$ and $C_{11}$ positions on the cyclopentyl ring, a cis double bond between $C_5$ and $C_6$, and a trans double bond between $C_{13}$ and $C_{14}$. Thus, the naturally occurring prostaglandins are exemplified by the following structures.

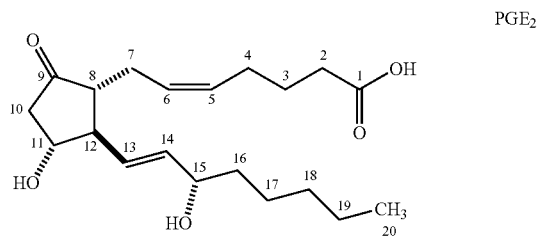

PGE$_2$

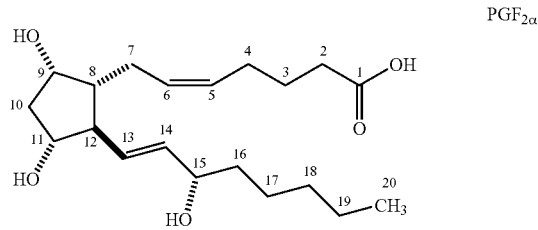

PGF$_{2\alpha}$

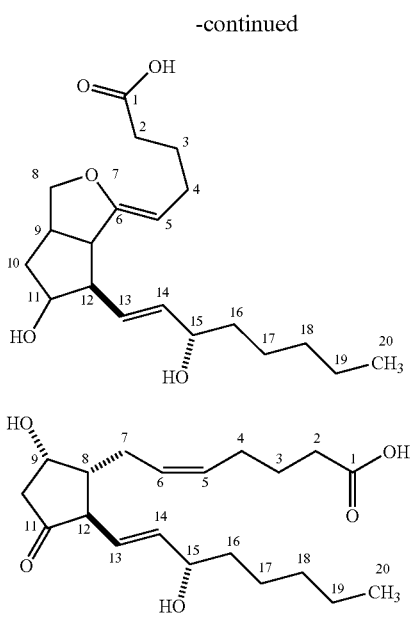

All naturally occurring prostaglandins have a carboxylic acid moiety at the $C_1$ position. The carboxylic acid moiety is a site for metabolic degradation by beta oxidation, which contributes to the rapid metabolism of the naturally occurring prostaglandins. Attempts have been made to prevent beta oxidation by modifying the carboxylic acid moiety at the 1 position as an ester moiety, a sulfonamide moiety, and as a tetrazole (see PCT Publication Nos. WO 99/12895, WO 99/12896, and WO 99/12898). However, such modifications have either resulted in only modest increases in half-life (such as the esters) or resulted in compounds with diminished potency.

An alternative approach has been to replace $C_1$ with a heteroatom. For example, PGF analogs containing a sulfonic acid moiety at $C_1$ (see Iguchi, Y.; Kori, S.; Hayashi, The chemistry of prostaglandins containing the sulfo group. M. *J. Org. Chem.*, 1975 40, 521–523) and PGF analogs containing a phosphonic acid moiety at $C_1$ (see Kluender, H. C. & Woessner, W., The Synthesis of dimethylphosphonoprostaglandin analogs, *Prostaglandins and Medicine*, 1979 2: pp.441–444,) have been disclosed. However, such compounds suffer from significantly diminished potency.

Further research in the area of heteroatom-containing $C_1$ replacements has been hampered by the lack of a general synthetic route to advanced or key intermediates that would allow for the rapid preparation of a multitude of variants to replace $C_1$. The Corey route to prostaglandins was specifically designed for a carboxcyclic acid moiety, and modifications which create reagents with relatively acidic protons are either incompatible with this route or cause significant optimization of this difficult step for each new $C_1$ replacement. Syntheses of Prostaglandin analogs via the Corey route are described in the following references: Corey, E. J.; Weinshenker, N. M.; Schaaf, T. K.; Huber, W *J. Am. Chem. Soc.*, 1969, 91, 5675 and Corey, E. J.; Schaaf, T. K.; Huber, W; Koelliker, U.; Weinshenker, N. M.; *J. Am. Chem. Soc.*, 1970, 92, 397.

Thus, while a few prostaglandin analogs wherein $C_1$ has been replaced with a heteroatom-containing moiety have been disclosed, there is a continuing need for suitable $C_1$ replacements that result in potent, selective prostaglandin derivatives for the treatment of a variety of diseases and other conditions. Therefore, it is an object of this invention to provide 2-decarboxy-2-phosphinico derivatives of prostaglandins that can be used to treat medical and cosmetic conditions.

Prostaglandin analogs have potent biological activities of a hormonal or regulatory nature. Examples of the biological activities and the conditions they can be used to treat are discussed below.

PGE Analogs

Analogs of PGE are useful for treating a variety of medical conditions including pain. For example, $EP_1$ receptor antagonists have been used to block the pain induced by $PGE_2$ injections in mice, because of their affinities for the $EP_1$ receptor (see Ruel R, Lacombe P, Abramovitz M, Godbout C, Lamontagne S, Rochette C, Sawyer N, Stocco R, Tremblay N M, Metters K M, Labelle M New class of biphenylene dibenzazocinones as potent ligands for the human $EP_1$ prostanoid receptor *Bioorg. Med. Chem. Lett.* 1999 9 2699–2704; and Hallinan E A, Hagen T J, Tsymbalov S, Husa R K, Lee A C, Staplefield A, Savage M A Aminoacetyl moiety as a potential surrogate for diacylhydrazine group of SC-51089, a potent $PGE_2$ antagonist, and its analogs *J. Med. Chem.* 1996 39 609).

Another use for PGE analogs is the treatment of arthritis. As opposed to using an $EP_1$ antagonist to prevent pain as a treatment for arthritis, an alternate approach for the attenuation of the disease is by activating chondrocytes with a prostaglandin that activates the $EP_3$ receptor, and possibly the $EP_4$ receptor (see Kiriyama M, Ushikubi F, Kobayashi T, Hirata M, Sugimoto Y, Narumiya S Binding specificities of the prostanoid receptors. *Br. J. Pharmacol.* 1997 122 217–224; and Narumiya S Roles of prostanoids in health and disease, lessons from receptor-knockout mice *Int. Congr. Ser.* 1999 1181 261–269).

PGE analogs are also useful to treat bone disorders such as osteoporosis. Bone stimulating properties of prostaglandins have been noticed in infants being dosed with $PGE_1$ as a part of treatment for patent ductus arteriosis (see Ueda K, Saito A, Nakano H, Aoshima M, Yokota M. Muraoka R, Iwaya T Brief clinical and laboratory observations. Cortical hyperostosis following long-term administration of prostaglandin E1 in infants with cyanotic congenital heart disease. *J. Pediat.* 1980, 97, 834). Systemically administered $PGE_2$ was subsequently found to stimulate new bone formation in dogs (see Shih M S, Norridin R W $PGE_2$ induces regional remodeling changes in Haversian envelope: A histomorphometric study of fractured ribs in beagles *Bone and Mineral* 1986 1 227), in estrogen-depleted rats (see Mori S, Jee W S S, Li X J, Chan S, Kimmel D B Effects of prostaglandin E2 on production of new cancellous bone in the axial skeleton of ovariectomized rats. *Bone* 1990 11 103) and to stimulate remodeling in the proximal tibia of estrogen-depleted rats (see Chyun Y S, Raisz L G Stimulation of bone formation by prostaglandin E2 *Prostaglandins* 1984 27 97). $PGE_2$ strongly stimulates bone resorption as well as bone formation. However, it is thought that more than one receptor may be responsible for the bone anabolic effects of $PGE_2$ (see Roof S L, deLong M A, Charest R P Messenger-RNA expression of prostaglandin receptors $EP_1$, $EP_2$, $EP_3$ and $EP_4$ in human osteoblast-like cells and 23 human tissues. *J. Bone Min. Res.*, 1996 11, S337; Maruyama, T, Ohuchida S New 3,7 dithiaprostanoic acid derivatives useful for the prevention and treatment of abnormal bone formation and neuronal cell death. EP 855389, 29 Jul. 1998; Sakuma Y, Tanaka K, Suda M, Yasoda A, Natsui K, Tanaka I, Ushikubi F, Narumiya S, Segi E, Sugimoto Y, Ichikawa A, Nakao K Crucial involvement of the $EP_4$ subtype of prostaglandin E receptor in osteoclast formation by proinflammatory cytokines and lipopolysaccharide *J. Bone Miner. Res.* 2000 15(2) 218–227).

PGE derivatives may also be used to treat vascular disease. $PGE_1$ is used clinically to lower blood pressure and improve vascular circulation. The role that the EP receptors have in the vasculature is now being determined. In a recent report of murine prostanoid receptor knockout (KO) mice, there was demonstrated a sexual dimorphism in EP-mediated blood pressure regulation (see Audoly L P, Tilley J, Key M, Nguyen M, Stock J L, McNeish J D, Koller B H, Coffman T M Identification of specific EP receptors responsible for the hemodynamic effects of $PGE_2$ *Am. J. Physiol.* 1999 46(3) H924–930). In female KO mice, the $EP_2$ and $EP_4$ receptors mediated a vasodepressor response, whilst in the males it is the $EP_1$ receptor that mediates the vasodepressor response, which is opposed by the $EP_3$ receptor.

Additionally, antagonists of prostaglandin $E_2$ receptors, particularly $EP_4$ receptors have a diuretic effect and may be used for treating hypertension and premenstrual tension), protecting agents for nerve cells, lowering intraocular pressure for treating glaucoma (see $EP_2$ selective agonists, and selective agonists of the $EP_1$ receptor were similarly effective at lowering intraocular pressure. However, the $EP_1$ selective agonists may cause pain as a side effect.

PGE analogs can be used to sexual dysfunction such as erectile dysfunction (see Maw G N Pharmacological therapy for the treatment of erectile dysfunction *Annu. Rep. Med. Chem.* 1999 34 71–80; and Anon. Alprostadil (nexmed): Alprox-TD, Befar, Femprox, prostaglandin E1 (nexmed) *Drugs R&D* 1999, 2(6) 413–414) and to treat women's sexual arousal dysfunction).

PGE analogs can be used to treat asthma (see Karim S M M, Adaikin P G, Kottegoda S R Prostaglandins and human respiratory tract smooth muscle: Structure activity relationship. *Adv. Prostaglandin Thromboxane Res.* 1980 7 969–980). To date, asthma treatment with prostaglandins has focused on the relaxant $EP_2$ and $EP_4$ receptors and thromboxane antagonists.

PGE analogs can be used for enhancing skin pigmentation. For example, $PGE_1$ can be used in conjunction with phosphodiesterase inhibitors to enhance skin pigmentation. The enhancement of activity in the presence of diesterase inhibitors suggests that the $EP_2$ and the $EP_4$ receptors may be responsible.

PGE analogs, such as those having affinity for the $EP_2$ and $EP_4$ receptors can be used to inhibit cell migration.

Furthermore, $EP_3$ selective agonists can be used to enhance the uterine contractions of $PGF_{2\alpha}$, and inhibit gastric acid secretion.

$EP_3$-selective ligands may useful in preventing or treating, or both, such conditions as hepatic diseases, renal diseases, pancreatitis, and myocardial infarct (see Flisiak R, Prokopowicz D Effect of misoprostol on the course of viral hepatitis B Hepato-Gastroenterology 1997 44(17), 1419–1425; and Mihele, Denisa; Cristea, Elena; Mihele, Dana; Cocu, F. The testing of the hepatoprotective action of some new synthetic prostaglandins *Farmacia (Bucharest)* 1999 47(5), 43–58; and Vengerovsky A I, Baturina N O, Saratikov A S Hepatoprotective action of prostaglandins *Eksp. Klin. Farmakol.* 1997 60(5), 78–82).

The $EP_4$ selective ligands have also been used for the prevention of neuronal cell death. $EP_2$ selective ligands can be used for protection against neuronal damage in the eye.

Therefore, it is an object of this invention to provide novel prostaglandin derivatives that can be used as protective agents for nerve cells.

PGF Analogs

Analogs of $PGF_{2a}$ are also useful for the treatment of a variety of medical conditions. For example, PGF analogs can be used to treat bone disorders, such as osteoporosis. For example, one approach is to selectively activate the excitatory FP receptor as a means of reversing osteoporosis (see Hartke, J R, Jankowsky, M L, deLong M A, Soehner M E, Jee W S S, Lundy M W Prostanoid F P agonists build bone in the ovariectomized rat. *J. Bone Min. Res.* 1999, 14, S207; and Lundy M W, deLong M A, Combs K S, Gross G J, Soehner M E, Hartke J R Restoration of cancellous architecture and increased bone strength in aged osteopenic rats treated with fluprostenol *J. Bone Min. Res.* 1999 14, S401.29).

FP ligands have also been proposed for the management of vascular diseases e.g., as vasorelaxants. It is likely that the activity of these ligands is mediated by a distinct subtype or splice variant of the FP receptor. $PGF_1$ analogs have also been disclosed for use in the treatment of diabetic and other forms of peripheral vascular disease (see Ueno, R Ueno, R, Oda, T. Prostaglandins of the F series U.S. Pat. No. 5,770, 759. Jun. 23 1998), perhaps mediated by the same receptor.)

FP receptor ligands may be used to treat ocular disorders such as glaucoma (see Kerstetter J R, Brubaker R F, Wilson S E, Kullerstrand L J Prostaglandin F2 alpha-1-isopropylester lowers intraocular pressure without decreasing aqueous humor flow *Am. J. Ophth.* 1988 105 30–34).

PGF analogs can be used as sleep inducing agents (see Matsumura H Prostaglandins and sleep *Saishin No to Shinkei Kagaku Shirizu* 1998 10 79–89).

Other uses for the PGF derivatives include treating skin disorders; circulatory disorders, such as hypertension; gastrointestinal disorders; hair loss; respiratory disorders; and fertility control. More information regarding the biological effects of Prostaglandin F analogs is disclosed in the following references: PCT Publication No. WO 99/12895, 1999; PCT Publication No. WO 99/12896, 1999; PCT Publication No. WO 99/12898; *Abstr.* 1999, 194116 Molecular mechanisms of diverse actions of prostanoid receptors, *Biochimica et Biophysica Acta,* 1259 (1995) 109–120; U.S. Pat. Nos. 3,776,938 and 3,882,241; G.B. Patent No. 1,456,512 (1976) issued to Pfizer Inc., Bundy, G. L.; Lincoln, F. H., Synthesis of 17-Phenyl-18,19,20-trinor prostaglandins I. The PG1 Series *Prostaglandins* 1975 9 1–4; CRC Handbook of Eicosanoids: Prostaglandins and Related Lipids Vol. 1, Chemical and Biochemical Aspects, Parts A & B, A. L. Willis, eds., CRC Press (1987); Liljebris, C.; et. al. Derivatives of 17-Phenyl-18,19,20-trinorprostaglandin F2a Isopropyl Ester: Potential Antiglaucoma Agents, *Journal of Medicinal Chemistry* 1995 38 289–304; Collins, P. W.; Djuric, S. W. Synthesis of Therapeutically Useful Prostaglandin and Prostacyclin Analogs, *Chemical Reviews* 1993 93 1533–1564.

PGI Analogs

PGI analogs of prostaglandins have been disclosed for use in the reproductive system (see Negishi, M., Sugimoto, Y., Ichikawa, A. Molecular mechanisms of the diverse actions of prostanoid receptors. *Biochim. Biophys. Acta* 1259 1995 109–120; and Collins P W, Djuric S W Synthesis of therapeutically useful prostaglandin and prostacyclin analogs Chem. Rev. 1993 93 1533–1564). PGI derivatives function as cervical maturing agents and can be used to inhibit uterine contraction and prevent premature delivery. Prostacyclin ($PGI_2$) is also used clinically to lower blood pressure and improve vascular circulation.

IP ligands have also been proposed for this area, e.g., treating peripheral vascular disease, treating pulmonary hypertension, and reducing blood pressure (see Vayssairat M Preventive effect of an oral prostacyclin analog, beraprost sodium, on digital necrosis in systemic sclerosis J. Rheumatol. 1999 26(10) 2173–2178; Murakami T, Sawada K Effect of isocarbacyclin methyl ester incorporated in lipid microspheres on experimental models of peripheral obstructive disease. Arzn. Forschung. 1995 45 991–994: and Hall A, Smith W H T Clinprost Teijin Curr. Opin. Cardiovasc; Pulm. Renal Invest. Drugs 1999 1(5) 605–610).

Prostaglandins have been proposed as protective agents for nerve cells. Several receptors several receptors have been investigated, with the 'relaxant' receptors being preferred.

PGD Analogs

PGD analogs can be used as sleep inducing agents. Sleep induction is generally thought to arise as a result of stimulation of the DP receptor (see Matsumura H Prostaglandins and sleep Saishin No to Shinkei Kagaku Shirizu 1998 10 79–89). Antagonists of the DP receptor, may be orally active and may be used as anti-allergy agents.

Thromboxanes

Some thromboxane analogs are orally active and may be used as anti-allergy agents. Thromboxane analogs may also be used to treat vascular disease; thromboxane antagonists are used to prevent platelet coagulation.

Thromboxane mediates potent vasoconstriction and irreversible platelet aggregation (see Terada N, Yamakoshi T, Hasegawa M, Tanikawa H, Nagata H, Maesako K I, Konno A Effect of a thromboxane A2 receptor antagonist, ramatroban (BAY u3405), on inflammatory cells, chemical mediators and non-specific nasal hyperreactivity after allergen challenge in patients with perennial allergic rhinitis. Allergol. Int. 1998 47(1), 59–67; and Miyamoto T, Takishima T A comparison in the efficacy and safety between ramatroban (BAY u 3405) and ozagrel-HCl for bronchial asthma: a phase III, multi-center, randomized, double-blind, group comparative study. Rinsho Iyaku. 1997 13 599–639). Thromboxane synthesis inhibitors have also been proposed for these applications (see McCullough P A Ridogrel (Janssen) Curr. Opin. Anti-Inflammatory Immunomodulatory Invest. Drugs 1999 1(3), 265–276; Inoue H Thromboxane A2 receptor antagonists Farumashia 1996, 32(10), 1221–1225; Cayatte A J, Du Y The thromboxane A2 receptor antagonist, S18886, decreases atherosclerotic lesions and serum intracellular adhesion molecule-1 in the Apo E knockout mouse. Circulation. 1998 98 115; Verbeuren T, Descombes J J The TP-receptor antagonist S 18886 unmasks vascular relaxation and potentiates the anti-platelet action of $PGD_2$. Thromb. Haemostasis. 1997 693; and Yoshida K, Sato H Synthesis and pharmacological activities of the new TXA2 receptor antagonist Z-335 and related compounds. AFMC 1995 95 53).

Other Prostaglandins

Other prostaglandins, such as $PGA_1$ in conjunction with phosphodiesterase inhibitors, may be used to enhance skin pigmentation. The enhancement of activity in the presence of diesterase inhibitors suggests that the $EP_2$ and the $EP_4$ receptors may be responsible.

Alzheimer's Disease and renal salt wasting may be controlled by inhibition of the synthesis or activity of delta-12-$PGJ_2$. This prostaglandin is a known ligand of PPARγ.

However, none of the PGE, PGD, thromboxane, and PGI analogs disclosed above have a 2-decarboxy-2-phosphinico group at $C_1$. Therefore, it is an object of this invention to provide prostaglandin derivatives wherein $C_1$ has been replaced with a 2-decarboxy-2-phosphinico group. Furthermore, prostaglandins having a carboxyl group at $C_1$ suffer from the drawback that they are rapidly metabolized and excreted. It is a further object of this invention to provide prostaglandin derivatives that are less rapidly metabolized and excreted than known prostaglandins and derivatives thereof.

SUMMARY OF THE INVENTION

This invention relates to 2-decarboxy-2-phosphinico prostaglandin derivatives and methods for their preparation and use. These derivatives comprise a modified α-chain and an Ω-chain bonded to a ring structure. The modified α-chain has a 2-decarboxy-2-phosphinico group at position $C_1$. Without wishing to be bound by theory, it is thought that the reason prior art prostaglandins are rapidly metabolized and excreted is because transport proteins in a subject's kidneys bind with the carboxyl group at $C_1$ and actively metabolize and excrete the prostaglandins. It is further theorized that these transport proteins do not recognize, or at least do not as readily bind with, the 2-decarboxy-2-phosphinico group at position $C_1$, thereby rendering the 2-decarboxy-2-phosphinico prostaglandin derivatives longer lasting.

DETAILED DESCRIPTION OF THE INVENTION

Publications and patents are referred to throughout this disclosure. All U.S. Patents cited herein are hereby incorporated by reference.

All percentages, ratios, and proportions used herein are by weight unless otherwise specified.

Definition and Usage of Terms

The following is a list of definitions for terms, as used herein:

"Activate" means binding and signal transduction of a receptor.

"Acyl group" means a monovalent group suitable for acylating a nitrogen atom to form an amide or carbamate, an alcohol to form a carbonate, or an oxygen atom to form an ester group. Preferred acyl groups include benzoyl, acetyl, tert-butyl acetyl, para-phenyl benzoyl, and trifluoroacetyl. More preferred acyl groups include acetyl and benzoyl. The most preferred acyl group is acetyl.

"Agonist" means a compound that activates a receptor.

"Antagonist" means a compound that inhibits a receptor.

"Aromatic group" means a monovalent group having a monocyclic ring structure or fused bicyclic ring structure. Monocyclic aromatic groups contain 5 to 10 carbon atoms, preferably 5 to 7 carbon atoms, and more preferably 5 to 6 carbon atoms in the ring. Bicyclic aromatic groups contain 8 to 12 carbon atoms, preferably 9 or 10 carbon atoms in the ring. Bicyclic aromatic groups include groups wherein only one ring is aromatic. Aromatic groups are unsubstituted. The most preferred aromatic group is phenyl.

"Carbocyclic group" means a monovalent saturated or unsaturated hydrocarbon ring. Carbocyclic groups are monocyclic, or are fused, spiro, or bridged bicyclic ring systems. Monocyclic carbocyclic groups contain 4 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups are unsubstituted. Preferred carbocyclic groups include cyclopentyl, cyclohexyl, cyclohexenyl, cycloheptyl, and cyclooctyl. More preferred carbocyclic groups include cyclohexyl, cycloheptyl, and cyclooctyl. The most preferred carbocyclic group is cycloheptyl. Carbocyclic groups are not aromatic.

"DP receptor" means known human DP receptors, their splice variants, and undescribed receptors that have similar binding and activation profiles as the known human DP receptors.

"EP receptor" means known human EP receptors, their splice variants, and undescribed receptors that have similar binding and activation profiles as the known human EP receptors.

"FP receptor" means known human FP receptors, their splice variants, and undescribed receptors that have similar binding and activation profiles as the known human FP receptors.

"Halogen atom" means F, Cl, Br, or I. Preferably, the halogen atom is F, Cl, or Br; more preferably Cl or F; and most preferably F.

"Halogenated hydrocarbon group" means a substituted monovalent hydrocarbon group or a substituted carbocyclic group, wherein at least one substituent is a halogen atom. Halogenated hydrocarbon groups can have a straight, branched, or cyclic structure. Preferred halogenated hydrocarbon groups have 1 to 12 carbon atoms, more preferably 1 to 6 carbon atoms, and most preferably 1 to 3 carbon atoms. Preferred halogen atom substituents are Cl and F. The most preferred halogenated hydrocarbon group is trifluoromethyl.

"Heteroaromatic group" means an aromatic ring containing carbon and 1 to 4 heteroatoms in the ring. Heteroaromatic groups are monocyclic or fused bicyclic rings. Monocyclic heteroaromatic groups contain 5 to 10 member atoms (i.e., carbon and heteroatoms), preferably 5 to 7, and more preferably 5 to 6 in the ring. Bicyclic heteroaromatic rings contain 8 to 12 member atoms, preferably 9 or 10 in the ring. Heteroaromatic groups are unsubstituted. Preferred heteroaromatic groups include thienyl, thiazolyl, purinyl, pyrimidyl, pyridyl, and furanyl. More preferred heteroaromatic groups include thienyl, furanyl, and pyridyl. The most preferred heteroaromatic group is thienyl.

"Heteroatom" means an atom other than carbon in the ring of a heterocyclic group or the chain of a heterogeneous group. Preferably, heteroatoms are selected from the group consisting of nitrogen, sulfur, and oxygen atoms. Groups containing more than one heteroatom may contain different heteroatoms.

"Heterocyclic group" means a saturated or unsaturated ring structure containing carbon and 1 to 4 heteroatoms in the ring. No two heteroatoms are adjacent in the ring. Heterocyclic groups are not aromatic. Heterocyclic groups are monocyclic, or are fused or bridged bicyclic ring systems. Monocyclic heterocyclic groups contain 4 to 10 member atoms (i.e., including both carbon atoms and at least 1 heteroatom), preferably 4 to 7, and more preferably 5 to 6 in the ring. Bicyclic heterocyclic groups contain 8 to 12 member atoms, preferably 9 or 10 in the ring. Heterocyclic groups are unsubstituted. Preferred heterocyclic groups include piperzyl, morpholinyl, tetrahydrofuranyl, tetrahydropyranyl, and piperdyl.

"Heterogeneous group" means a saturated or unsaturated chain containing 1 to 18 member atoms (i.e., including both carbon and at least one heteroatom). No two heteroatoms are adjacent. Preferably, the chain contains 1 to 12 member atoms, more preferably 1 to 6, and most preferably 1 to 4. The chain may be straight or branched. Preferred branched heterogeneous groups have one or two branches, preferably one branch. Preferred heterogeneous groups are saturated. Unsaturated heterogeneous groups have one or more double bonds, one or more triple bonds, or both. Preferred unsaturated heterogeneous groups have one or two double bonds or one triple bond. More preferably, the unsaturated heterogeneous group has one double bond. Heterogeneous groups are unsubstituted.

"IP receptor" means known human IP receptors, their splice variants, and undescribed receptors that have similar binding and activation profiles as the known human IP receptors.

"Monovalent hydrocarbon group" means a chain of 1 to 18 carbon atoms, preferably 1 to 12, more preferably 1 to 6, carbon atoms. "Lower monovalent hydrocarbon group" means a monovalent hydrocarbon group having 1 to 4, preferably 1 to 3 carbon atoms, more preferably 1 to 2, carbon atoms. Preferred lower monovalent hydrocarbon groups include alkyl groups such as methyl and ethyl. Monovalent hydrocarbon groups may have a straight chain or branched chain structure. Preferred monovalent hydrocarbon groups have one or two branches, preferably 1 branch. Preferred monovalent hydrocarbon groups are saturated. Unsaturated monovalent hydrocarbon groups have one or more double bonds, one or more triple bonds, or combinations thereof. Preferred unsaturated monovalent hydrocarbon groups have one or two double bonds or one triple bond; more preferred unsaturated monovalent hydrocarbon groups have one double bond.

"Pharmaceutically acceptable" means suitable for use in a human or other mammal.

"Prostaglandin" means a fatty acid derivative which has a variety of potent biological activities of a hormonal or regulatory nature.

"Protecting group" is a group that replaces the active hydrogen of a hydroxyl moiety thus preventing undesired side reaction at the hydroxyl moiety. Use of protecting groups in organic synthesis is well known in the art. Examples of protecting groups are found in *Protecting Groups in Organic Synthesis* by Greene, T. W. and Wuts, P. G. M., $2^{nd}$ ed., Wiley & Sons, Inc., 1991. Preferred protecting groups include silyl ethers, alkoxymethyl ethers, tetrahydropyranyl, tetrahydrofuranyl, esters, and substituted or unsubstituted benzyl ethers.

"Selective" means having a binding or activation preference for a specific receptor over other receptors which can be quantitated based upon receptor binding or activation assays.

"Subject" means a living vertebrate animal such as a mammal (preferably human) in need of treatment.

"Substituted aromatic group" means an aromatic group wherein 1 to 4 of the hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, aromatic groups, substituted aromatic groups, or any combination thereof. More preferred substituents include halogen atoms, monovalent hydrocarbon groups, and substituted monovalent hydrocarbon groups. Preferred substituted aromatic groups include naphthyl. The substituents may be substituted at the ortho, meta, or para position on the ring, or any combination thereof. The preferred substitution pattern on the ring is ortho or meta. The most preferred substitution pattern is ortho.

"Substituted carbocyclic group" means a carbocyclic group wherein 1 to 4 hydrogen atoms bonded to carbon atoms in the ring have been replaced with other substituents. Preferred substituents include: halogen atoms, cyano groups, monovalent hydrocarbon groups, monovalent heterogeneous groups, substituted monovalent hydrocarbon groups, aromatic groups, substituted aromatic groups, or any combination thereof. More preferred substituents include halogen atoms and substituted monovalent hydrocarbon groups. Carbocyclic group does not include aromatic rings.

"Substituted heteroaromatic group" means a heteroaromatic group wherein 1 to 4 hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, substituted heterogeneous groups, phenyl groups, phenoxy groups, or any combination thereof. More preferred substituents include halogen atoms, halogenated hydrocarbon groups, monovalent hydrocarbon groups, and phenyl groups.

"Substituted heterocyclic group" means a heterocyclic group wherein 1 to 4 hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, substituted heterogeneous groups, halogenated hydrocarbon groups, phenyl groups, phenoxy groups, or any combination thereof. More preferred substituents include halogen atoms and halogenated hydrocarbon groups. Substituted heterocyclic groups are not aromatic.

"Substituted heterogeneous group" means a heterogeneous group, wherein 1 to 4 of the hydrogen atoms bonded to carbon atoms in the chain have been replaced with other substituents. Preferred substituents include halogen atoms, hydroxy groups, alkoxy groups (e.g., methoxy, ethoxy, propoxy, butoxy, and pentoxy), aryloxy groups (e.g., phenoxy, chlorophenoxy, tolyloxy, methoxyphenoxy, benzyloxy, alkyloxycarbonylphenoxy, and acyloxyphenoxy), acyloxy groups (e.g., propionyloxy, benzoyloxy, and acetoxy), carbamoyloxy groups, carboxy groups, mercapto groups, alkylthio groups, acylthio groups, arylthio groups (e.g., phenylthio, chlorophenylthio, alkylphenylthio, alkoxyphenylthio, benzylthio, and alkyloxycarbonylphenylthio), aromatic groups (e.g., phenyl and tolyl), substituted aromatic groups (e.g., alkoxphenyl, alkoxycarbonylphenyl, and halophenyl), heterocyclic groups, heteroaromatic groups, and amino groups (e.g., amino, mono- and di-alkylamino having 1 to 3 carbon atoms, methylphenylamino, methylbenzylamino, alkanylamido groups of 1 to 3 carbon atoms, carbamamido, ureido, and guanidino).

"Substituted monovalent hydrocarbon group" means a monovalent hydrocarbon group wherein 1 to 4 of the hydrogen atoms bonded to carbon atoms in the chain have been replaced with other substituents. Preferred substituents include halogen atoms; halogenated hydrocarbon groups; alkyl groups (e.g., methyl, ethyl, propyl, and butyl); hydroxy groups; alkoxy groups (e.g., methoxy, ethoxy, propoxy, butoxy, and pentoxy); aryloxy groups (e.g., phenoxy, chlorophenoxy, tolyloxy, methoxyphenoxy, benzyloxy, alkyloxycarbonylphenoxy, and acyloxyphenoxy); acyloxy groups (e.g., propionyloxy, benzoyloxy, and acetoxy); carbamoyloxy groups; carboxy groups; mercapto groups; alkylthio groups; acylthio groups; arylthio groups (e.g., phenylthio, chlorophenylthio, alkylphenylthio, alkoxyphenylthio, benzylthio, and alkyloxycarbonylphenylthio); aryl groups (e.g., phenyl, tolyl, alkoxyphenyl, alkoxycarbonylphenyl, and halophenyl); heterocyclyic groups; heteroaryl groups; and amino groups (e.g., amino, mono- and di-alkanylamino groups of 1 to 3 carbon atoms, methylphenylamino, methylbenzylamino, alkanylamido groups of 1 to 3 carbon atoms, carbamamido, ureido, and guanidino).

"TP receptor" means known human TP receptors, their splice variants, and undescribed receptors that have similar binding and activation profiles as the known human TP receptors.

2-Decarboxy-2-phosphinico prostaglandin derivatives

The 2-decarboxy-2-phosphinico prostaglandin derivatives comprise a modified α-chain having a phosphinico group at position 2 and an Ω-chain, both bonded to a 5-membered ring structure. The modified α-chain has the formula

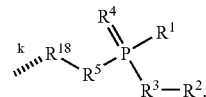

Bond k is selected from the group consisting of a single bond and a double bond. Bond k is preferably a single bond.

$R^1$ is selected from the group consisting of a hydrogen atom, a monovalent hydrocarbon group having 1 to 4 carbon atoms, and a monovalent heterogenous group having 1 to 4 member atoms. Preferably $R^1$ is a hydrogen atom or a monovalent hydrocarbon group. When $R^1$ is a monovalent hydrocarbon group, it preferably has 1 to 3 carbon atoms, more preferably 1 to 2 carbon atoms, most preferably 1 carbon atom. Most preferably, $R^1$ is a methyl group.

$R^2$ is selected from the group consisting of a hydrogen atom, a monovalent hydrocarbon group, a substituted monovalent hydrocarbon group, a monovalent heterogeneous group, a substituted monovalent heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group. Preferably, $R^2$ is a hydrogen atom.

$R^3$ is selected from the group consisting of an oxygen atom, a sulfur atom, and NH. Preferably, $R^3$ is an oxygen atom.

$R^4$ is selected from the group consisting of an oxygen atom and a sulfur atom. $R^4$ is preferably an oxygen atom.

$R^5$ is a divalent group. $R^5$ is selected from the group consisting of a hydrocarbon group, a substituted hydrocarbon group, a heterogeneous group, and a substituted heterogeneous group. When $R^5$ is a heterogeneous group, $R^5$ has only one heteroatom, which is selected from the group consisting of oxygen, sulfur, and nitrogen. $R^5$ preferably has 1 to 5 member atoms when $R^5$ is a heterogenous group. $R^5$ preferably has 1 to 5 carbon atoms in the chain when $R^5$ is a hydrocarbon group. $R^5$ is preferably a hydrocarbon group.

R[5] may be saturated or unsaturated. R[5] preferably has a cis double bond at the $C_5$–$C_6$ position in the modified α-chain.

R[18] is selected from the group consisting of a sulfur atom and —$CH_2$—. R[18] is preferably —$CH_2$—.

In a preferred embodiment of the invention, the modified α-chain has 5 to 8 member atoms from the first carbon atom after the ring up to and including the phosphorous atom.

The Ω-chain has the formula

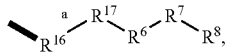

wherein bond a is selected from the group consisting of a single bond, a trans double bond, and a triple bond. Preferably, bond a is a single bond or a cis double bond.

R[6] is a bond or a divalent group selected from the group consisting of —$CH_2$—, —C(O)— and —$C(R^{10})(OR^{10})$—. Preferably, R[6] is —$C(R^{10})(OR^{10})$—.

R[7] is a bond or a divalent group having the formula —$(CD(D))_p$—X—$(CD(D))_q$—, wherein p is an integer from 0 to 3 and q is an integer from 0 to 3, X is selected from the group consisting of an oxygen atom, a divalent hydrocarbon group, a sulfur atom, SO, $SO_2$, and ND, and each D is independently selected from the group consisting of a hydrogen atom, a monovalent hydrocarbon group of 1 to 4 carbon atoms, and a monovalent heterogenous group of 1 to 4 member atoms. R[7] is preferably selected from the group consisting of —$CH_2O$—, —CH=CH—, —CH=C=CH—, —$CH_2S$—, —$CH_2CH_2$—, —$CH_2NH$—, —$CH_2NCH_2$—, and —$CH_2O(CH_2)_3O$—.

R[8] is selected from the group consisting of a hydrocarbon group, a substituted hydrocarbon group, a heterogenous group, a substituted heterogenous group, a carbocyclic group, a substituted carbocyclic group, a heterocyclic group, a substituted heterocyclic group, an aromatic group, a substituted aromatic group, a heteroaromatic group, and a substituted heteroaromatic group. When R[8] is a monocyclic group, it has 5 to 10 member atoms. When R[8] is a bicyclic group, it has 8 to 12 member atoms. R[8] is preferably selected from the group consisting of a methyl group, aromatic groups, substituted aromatic groups, heteroaromatic groups, and substituted heteroaromatic groups.

R[10] is selected from the group consisting of a hydrogen atom, a monovalent hydrocarbon group of 1 to 4 carbon atoms, and a monovalent heterogenous group of 1 to 4 member atoms. Preferably, R[10] is a hydrogen atom or a monovalent hydrocarbon group of 1 to 4 carbon atoms. When R[10] is a monovalent hydrocarbon group, R[10] preferably has 1 carbon atom. Most preferably, R[10] is a hydrogen atom.

R[16] is selected from the group consisting of —$CH_2$—, —NH—, and —$NR^{19}$—, wherein R[19] is selected from the group consisting of hydrocarbon groups, substituted hydrocarbon groups, heterogenous groups, and substituted heterogenous groups; with the proviso that R[19] may optionally be bonded together with R[8] to form a ring structure selected from the group consisting of heterocyclic groups and substituted heterocyclic groups. R[16] is preferably —$CH_2$—.

R[17] is selected from the group consisting of —$SO_2$—, C(O)—, and —$CH_2$—. R[17] is preferably —$CH_2$—.

In a preferred embodiment of the invention, the Ω-chain has 7 to 12 member atoms in the chain from the first carbon atom after the ring to R[8].

The ring structure is a 5-membered selected from the group consisting of a carbocyclic group, a substituted carbocyclic group, a heterocyclic group, and a substituted heterocyclic group.

The prostaglandin derivatives of this invention preferably have the general formula:

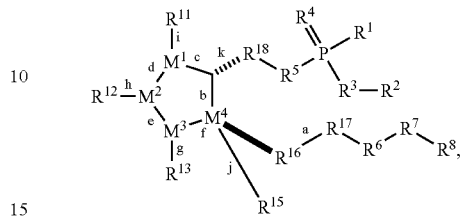

wherein bond a, bond k, R[1], R[2], R[3], R[4], R[5], R[6], R[7], R[8], R[16], R[17], and R[18] are as described above.

Each of bonds b, c, d, e, and f are independently selected from the group consisting of a single bond and a double bond. Preferably, 0 to 1 of bonds b, c, d, e, and f is a double bond. More preferably, each of bonds b, c, d, e, and f is a single bond.

Each of bonds g, h, i, and j are independently selected from the group consisting of nil, a single bond, and a double bond. Preferably, bond h is a single bond.

M[1], M[2], M[3], and M[4] are each independently selected from the group consisting of a carbon atom and a heteroatom. No two heteroatoms are adjacent. No more than two of M[1], M[2], M[3], and M[4] are heteroatoms. Preferably, no more than one of M[1], M[2], M[3], and M[4] is a heteroatom. Preferred heteroatoms for M[1], M[2], M[3], and M[4] include nitrogen and oxygen. More preferably, M[1], M[2], M[3], and M[4] are each carbon atoms.

R[11], R[12], R[13], and R[15] are each independently selected from the group consisting of nil, a halogen atom, a heteroatom, and R[2], with the proviso that, optionally, R[11] and R[12], R[12] and R[13], or R[11] and R[13] may be bonded together to form a ring structure such as a carbocyclic group, a heterocyclic group, an aromatic group, a heteroaromatic group, a substituted carbocyclic group, a substituted heterocyclic group, a substituted aromatic group, or a substituted heteroaromatic group. R[12] is preferably a hydrogen atom. R[11] is preferably selected from the group consisting of a hydrogen atom; an oxygen atom (i.e., when bond i is a double bond); and OR[9], wherein R[9] is selected from the group consisting of a hydrogen atom, a monovalent hydrocarbon group of 1 to 4 carbon atoms, and a monovalent heterogenous group of 1 to 4 member atoms.

When R[11] is OR[9], R[12] is a hydrogen atom, and M[2] is a carbon atom; R[13] is not a hydrogen atom, OR[9], a monovalent hydrocarbon group of 1 to 4 carbon atoms, a monovalent heterogenous group of 1 to 4 carbon atoms, a substituted monovalent hydrocarbon group of 1 to 4 carbon atoms, or a substituted monovalent heterogenous group of 1 to 4 carbon atoms.

R[13] is not $N(R^9)(OR^9)$ when bond g is a single bond and R[13] is not NOR[9] when bond g is a double bond. R[13] is preferably selected from the group consisting of a hydrogen atom; an oxygen atom (i.e., when bond i is a double bond); and OR[9]; with the proviso that R[13] is not OR[9] when R[11] is OR[9], M[1], M[2], M[3], and M[4] are each carbon atoms, and R[12] is a hydrogen atom.

Preferred prostaglandin derivatives of the above formula are selected from the group consisting of PGD, PGE, PGI, and thromboxane derivatives.

Derivatives suitable to use in this invention may also be any optical isomer, diastereomer, and enantiomer of the above structure; or any pharmaceutically-acceptable salts of the above structure; or any biohydrolyzable amides, esters, and imides of the above structure; or combinations thereof.

Typically, the 2-decarboxy-2-phosphinico prostaglandin derivative of the general formula described above has a formula selected from the group consisting of:

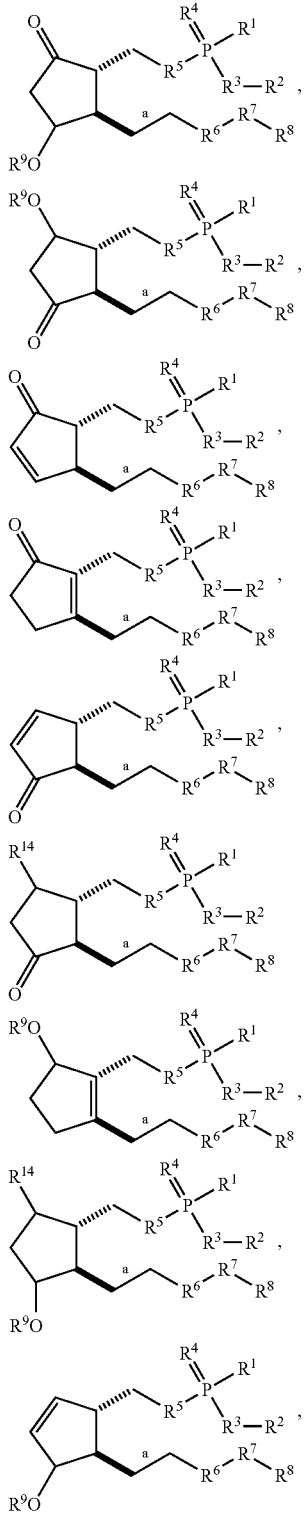

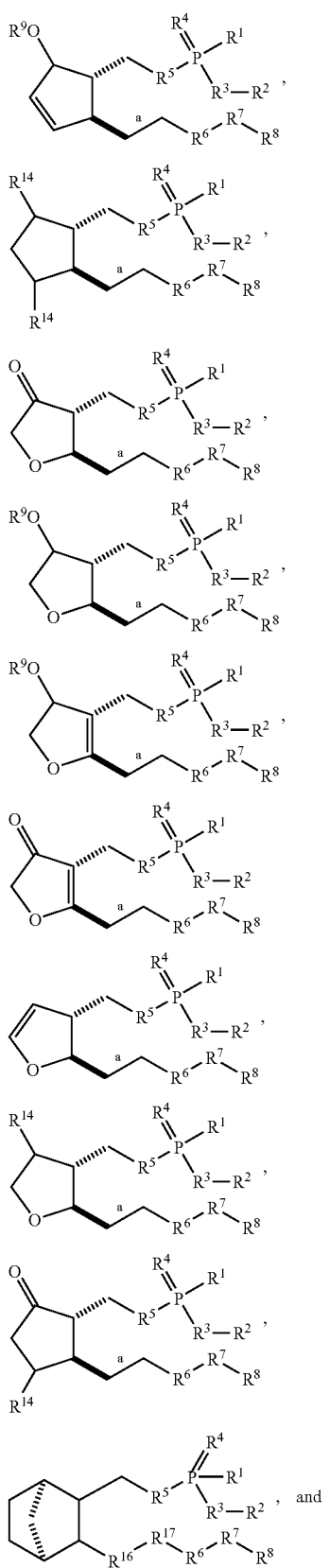

-continued

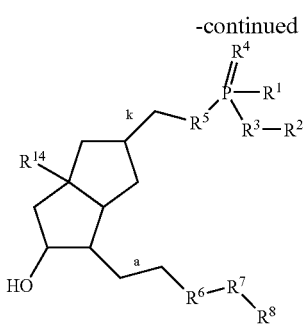

wherein bond a, bond k, $R^1$, $R^2$, $R^3$, $R^4$, $R^5$, $R^6$, $R^7$, $R^8$, $R^9$, $R^{16}$, and $R^{17}$ are as described above, and each $R^{14}$ is independently selected from the group consisting of nil, a hydrogen atom, a halogen atom, a monovalent hydrocarbon group of 1 to 4 carbon atoms, and a monovalent heterogenous group of 1 to 4 member atoms. Preferably, $R^9$ is a hydrogen atom.

Compositions

This invention further relates to compositions containing a prostaglandin derivative described above as an active ingredient (hereinafter, component A). The compositions can be pharmaceutical or cosmetic compositions, administered for treatment or prophylaxis of various conditions. Standard pharmaceutical formulation techniques are used, such as those disclosed in *Remington's Pharmaceutical Sciences*, Mack Publishing Company, Easton, Pa. (1990).

The composition further comprises component B) a carrier. "Carrier" means one or more compatible substances that are suitable for administration to a mammal. Carrier includes solid or liquid diluents, hydrotropes, surface-active agents, and encapsulating substances. "Compatible" means that the components of the composition are capable of being commingled with component A), and with each other, in a manner such that there is no interaction which would substantially reduce the efficacy of the composition under ordinary use situations. Carriers must be of sufficiently high purity and sufficiently low toxicity to render them suitable for administration to the mammal being treated. The carrier can be inert, or it can possess pharmaceutical benefits, cosmetic benefits, or both.

The choice of carrier for component B) depends on the route by which component A) will be administered and the form of the composition. The composition may be in a variety of forms, suitable, for example, for systemic administration (e.g., oral, rectal, nasal, sublingual, buccal, or parenteral) or topical administration (e.g., local application on the skin, ocular, liposome delivery systems, or iontophoresis).

Carriers for systemic administration typically comprise one or more ingredients selected from the group consisting of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others.

Ingredient a) is a diluent. Suitable diluents include sugars such as glucose, lactose, dextrose, and sucrose; polyols such as propylene glycol; calcium carbonate; sodium carbonate; glycerin; mannitol; and sorbitol. The amount of ingredient a) in the systemic composition is typically about 50 to about 90%.

Ingredient b) is a lubricant. Suitable lubricants are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of ingredient b) in the systemic composition is typically about 5 to about 10%.

Ingredient c) is a binder. Suitable binders include polyvinylpyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%.

Ingredient d) is a disintegrant. Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic composition is typically about 0.1 to about 10%.

Ingredient e) is a colorant such as an FD&C dye. The amount of ingredient e) in the systemic composition is typically about 0.005 to about 0.1%.

Ingredient f) is a flavor such as menthol, peppermint, and fruit flavors. The amount of ingredient f) in the systemic composition is typically about 0.1 to about 1.0%.

Ingredient g) is a sweetener such as aspartame and saccharin. The amount of ingredient g) in the systemic composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic composition is typically about 1 to about 5%.

Ingredient j) is a preservative such as methyl paraben and sodium benzoate. The amount of ingredient j) in the systemic composition is typically about 1 to about 5%.

Ingredient k) is a glidant such as silicon dioxide. The amount of ingredient k) in the systemic composition is typically about 1 to about 5%.

Ingredient m) is a solvent, such as water, isotonic saline, ethyl oleate, alcohols such as ethanol, and phosphate buffer solutions. The amount of ingredient m) in the systemic composition is typically 0 to about 10%.

Ingredient n) is a suspending agent. Suitable suspending agents include AVICEL® RC-591 from FMC Corporation of Philadelphia, Pa. and sodium alginate. The amount of ingredient n) in the systemic composition is typically about 1 to about 8%.

Ingredient o) is a surfactant such as lecithin, polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp.587–592; Remington's Pharmaceutical Sciences, 15th Ed. 1975, pp. 335–337; and McCutcheon's Volume 1, Emulsifiers & Detergents, 1994, North American Edition, pp. 236–239. The amount of ingredient o) in the systemic composition is typically about 0.1 to about 2%.

Although the amounts of components A) and B) in the systemic compositions will vary depending on the type of systemic composition prepared, the specific derivative selected for component A) and the ingredients of component B), in general, system compositions comprise 0.01% to 50% of component A) and 50 to 99.99% of component B).

Compositions for parenteral administration typically comprise A) 0.1 to 10% of a prostaglandin and B) 90 to 99.9% of a carrier comprising a) a diluent and m) a solvent. Preferably, component a) is propylene glycol and m) is ethanol or ethyl oleate.

Compositions for oral administration can have various dosage forms. For example, solid forms include tablets, capsules, granules, and bulk powders. These oral dosage forms comprise a safe and effective amount, usually at least 5%, and preferably from 25% to 50%, of component A). The oral dosage compositions further comprise 50 to 95% of component B), preferably 50 to 75%.

Tablets can be compressed, tablet triturates, enteric-coated, sugar-coated, film-coated. coated, or multiple-compressed. Tablets typically comprise component A), and component B) a carrier comprising ingredients selected from the group consisting of a) diluents, b) lubricants, c) binders, d) disintegrants, e) colorants, f) flavors, g) sweeteners, k) glidants, and combinations thereof. Preferred diluents include calcium carbonate, sodium carbonate, mannitol, lactose and cellulose. Preferred binders include starch, gelatin, and sucrose. Preferred disintegrants include alginic acid and croscarmelose. Preferred lubricants include magnesium stearate, stearic acid, and talc. Preferred colorants are the FD&C dyes, which can be added for appearance. Chewable tablets preferably contain g) sweeteners such as aspartame and saccharin, or f) flavors such as menthol, peppermint, and fruit flavors, or both.

Capsules (including time release and sustained release formulations) typically comprise component A), and B) a carrier comprising one or more a) diluents disclosed above in a capsule comprising gelatin. Granules typically comprise component A), and preferably further comprise k) glidants such as silicon dioxide to improve flow characteristics.

The selection of ingredients in the carrier for oral compositions depends on secondary considerations like taste, cost, and shelf stability, which are not critical for the purposes of this invention. One skilled in the art would know how to select appropriate ingredients without undue experimentation.

The solid compositions may also be coated by conventional methods, typically with pH or time-dependent coatings, such that A) the prostaglandin is released in the gastrointestinal tract in the vicinity of the desired application, or at various times to extend the desired action. The coatings typically comprise one or more components selected from the group consisting of cellulose acetate phthalate, polyvinylacetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise A) the prostaglandin and B) a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethylcellulose, and hydroxypropylmethylcellulose. Such compositions may further comprise b) lubricants, e) colorants, f) flavors, g) sweeteners, h) antioxidants, and k) glidants.

In an alternative embodiment of the invention, the prostaglandins are topically administered. Topical compositions that can be applied locally to the skin may be in any form including solutions, oils, creams, ointments, gels, lotions, shampoos, leave-on and rinse-out hair conditioners, milks, cleansers, moisturizers, sprays, skin patches, and the like. Topical compositions comprise: component A) the prostaglandin described above and component B) a carrier. The carrier of the topical composition preferably aids penetration of the prostaglandins into the skin. Component B) may further comprise one or more optional components.

The exact amounts of each component in the topical composition depend on various factors. The amount of component A) added to the topical composition is:

$$IC_{50} \times 10^{-2} \geq \% \text{ of component } A) \geq IC_{50} \times 10^{-3},$$

where $IC_{50}$ of component A) is expressed in nanomolar units. For example, if the $IC_{50}$ of the prostaglandin is 1 nM, the amount of component A) will be 0.001 to 0.01%. If the $IC_{50}$ of the prostaglandin is 10 nM, the amount of component A) will be 0.01 to 0.1%. If the $IC_{50}$ of the prostaglandin is 100 nM, the amount of component A) will be 0.1 to 1.0%. If the $IC_{50}$ of the prostaglandin is 1000 nM, the amount of component A) will be 1.0 to 10%, preferably 1.0 to 5%. The amount and dosage of component A) are critical. If the amount of component A) is outside the ranges specified above (i.e., either higher or lower), efficacy of the treatment may be reduced. $IC_{50}$ can be calculated according to the method in Reference Example 1, below. One skilled in the art would know how to calculated $IC_{50}$. The remainder of the composition, up to 100%, is component B).

The amount of B) the carrier employed in conjunction with component A) is sufficient to provide a practical quantity of composition for administration per unit dose of the prostaglandin. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Component B) the carrier may comprise a single ingredient or a combination of two or more ingredients. In the topical compositions, component B) is a topical carrier. Preferred topical carriers include one or more ingredients selected from the group consisting of water, alcohols, aloe vera gel, allantoin, glycerin, vitamin A and E oils, mineral oil, propylene glycol, PPG-2 myristyl propionate, dimethyl isosorbide, combinations thereof, and the like. More preferred carriers include propylene glycol, dimethyl isosorbide, and water.

The carrier of the topical composition may further comprise one or more ingredients selected from the group consisting of q) emollients, r) propellants, s) solvents, t) humectants, u) thickeners, v) powders, w) fragrances, and x) pigments.

Ingredient q) is an emollient. The amount of ingredient q) in the topical composition is typically 5 to 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Preferred emollients include stearyl alcohol and polydimethylsiloxane.

Ingredient r) is a propellant. The amount of ingredient r) in the topical composition is typically 5 to 95%. Suitable propellants include propane, butane, isobutane, dimethyl ether, carbon dioxide, nitrous oxide, and combinations thereof.

Ingredient s) is a solvent. The amount of ingredient s) in the topical composition is typically 5 to 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Preferred solvents include ethyl alcohol.

Ingredient t) is a humectant. The amount of ingredient t) in the topical composition is typically 5 to 95%. Suitable humectants include glycerin, sorbitol, sodium 2-pyrrolidone-5-carboxylate, soluble collagen, dibutyl phthalate, gelatin, and combinations thereof. Preferred humectants include glycerin.

Ingredient u) is a thickener. The amount of ingredient u) in the topical composition is typically 0 to 95%.

Ingredient v) is a powder. The amount of ingredient v) in the topical composition is typically 0 to 95%. Suitable powders include chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, and combinations thereof.

Ingredient w) is a fragrance. The amount of ingredient w) in the topical composition is typically 0.001 to 0.5%, preferably 0.001 to 0.1%.

Ingredient x) is a pigment. Suitable pigments include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically 0 to 10%.

In an alternative embodiment of the invention, topical pharmaceutical compositions for ocular administration are prepared by conventional methods. Topical pharmaceutical compositions for ocular administration typically comprise component A) and B) a carrier, such as purified water, and one or more ingredients selected from the group consisting of y) sugars such as dextrans, particularly dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethylcellulose, ethylcellulose, methylcellulose, and hydroxypropylmethylcellulose. Hydroxypropylmethylcellulose is preferred.

Examples of aa) salts suitable for use in the for use in the topical pharmaceutical composition for ocular administration include sodium chloride, potassium chloride, and combinations thereof.

Examples of cc) pH adjusting additives include HCl or NaOH in amounts sufficient to adjust the pH of the topical pharmaceutical composition for ocular administration to 7.2–7.5.

Component A) may also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines. A preferred formulation for topical delivery of the present compounds uses liposomes as described in Dowton et al., Influence of Liposomal Composition on Topical Delivery of Encapsulated Cyclosporin A: I. An in vitro Study Using Hairless Mouse Skin, *S.T.P. Pharma Sciences,* 1993 Vol. 3, pp. 404–407; Wallach and Philippot, New Type of Lipid Vesicle: Novasome®, *Liposome Technology,* 1993 Vol. 1, pp. 141–156; U.S. Pat. Nos. 4,911,928; 5,834,014.

Component A) may also be administered by iontophoresis (see, e.g., Internet site www.unipr.it/arpa/dipfarm/erasmus/erasm14.html; Banga et al., Hydrogel-based Iontotherapeutic Delivery Devices for Transdermal Delivery of Peptide/Protein Drugs, *Pharm. Res.* 1993 Vol. 10(5), pp. 697–702; Ferry, Theoretical Model of Iontophoresis Utilized in Transdermal Drug Delivery, *Pharmaceutical Acta Helvetiae,* 1995 Vol 70, pp. 279–287; Gangarosa et al., Modern Iontophoresis for Local Drug Delivery, *Int. J. Pharm,* 1995 Vol. 123, pp. 159–171; Green et al., Iontophoretic Delivery of a Series of Tripeptides Across the Skin in vitro, *Pharm. Res.,* 1991 Vol 8, pp. 1121–1127; Jadoul et al., Quantification and Localization of Fentanyl and TRH Delivered by Iontophoresis in the Skin, *Int. J. Pharm.* 1995 Vol. 120, pp. 221–8; O'Brien et al., An Updated Review of its Antiviral Activity, Pharmacokinetic Properties and Therapeutic Efficacy, *Drugs,* 1989Vol. 37, pp. 233–309; Parry et al., Acyclovir Biovailability in Human Skin, *J. Invest. Dermatol.,* 1992 Vol. 98 (6), pp. 856–63; Santi et al., Drug Reservoir Composition and Transport of Salmon Calcitonin in Transdermal Iontophoresis, *Pharm. Res.,* 1997 Vol 14 (1), pp. 63–66; Santi et al., Reverse Iontophoresis—Parameters Determining Electroosmotic Flow: I. pH and Ionic Strength, *J. Control. Release,* 1996 Vol. 38, pp. 159–165; Santi et al., Reverse Iontophoresis—Parameters Determining Electroosmotic Flow: II. Electrode Chamber Formulation, *J. Control. Release,* 1996 Vol. 42, pp. 29–36; Rao et al., Reverse Iontophoresis: Noninvasive Glucose Monitoring in vivo in Humans, *Pharm. Res.,* 1995 Vol. 12 (12), pp. 1869–1873; Thysman et al., Human Calcitonin Delivery in Rats by Iontophoresis, *J. Pharm. Pharmacol.,* 1994 Vol. 46, pp. 725–730; and Volpato et al., Iontophoresis Enhances the Transport of Acyclovir through Nude Mouse Skin by Electrorepulsion and Electroosmosis, *Pharm. Res.,* 1995 Vol. 12 (11), pp. 1623–1627.

Component A) may be included in kits comprising component A), a systemic or topical composition described above, or both; and information, instructions, or both that use of the kit will provide treatment for cosmetic and medical conditions in mammals (particularly humans). The information and instructions may be in the form of words, pictures, or both, and the like. In addition or in the alternative, the kit may comprise a prostaglandin derivative, a composition, or both; and information, instructions, or both, regarding methods of application of the prostaglandin derivative or composition, preferably with the benefit of treating or preventing cosmetic and medical conditions in mammals.

Use of the Prostaglandin Derivatives and Compositions

This invention further relates to methods for treating medical and cosmetic conditions in mammals. The prostaglandin derivatives, and compositions containing the derivatives, of this invention can be used to treat subjects suffering from many medical and cosmetic conditions. Generally, the method comprises administering to a mammal in need of treatment, a prostaglandin derivative (or composition) described above.

The conditions that can be treated depend on the type of derivative, i.e., the receptor or receptors for which the derivative has affinity and whether the derivative is an agonist or antagonist for the receptor.

Whether the derivative has affinity for the receptor typically depends on the substituent groups bonded to the ring ($R^{11}$ or $R^{13}$, or both, in the general structure above). For example, in PGE derivatives, which have affinity for the $EP_1$, $EP_2$, $EP_3$, and $EP_4$, receptors, typically $R^{11}$ is an oxygen atom and bond i is a double bond.

Whether the derivative is an agonist or antagonist of the receptor typically depends on the stereochemistry of the ring and the Ω-chain up to and including $R^6$ in the general formula above. If the stereochemistry of this portion of the derivative is the same as, or similar to, that of the naturally occurring prostaglandin, the derivative will be an agonist. If the stereochemistry differs from that of the naturally occurring prostaglandin, the derivative can be an antagonist. For example, naturally occurring $PGE_2$ has the formula:

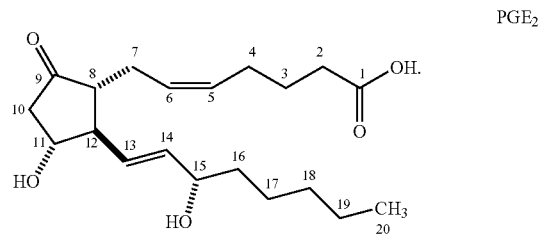

A PGE derivative according to this invention has the formula:

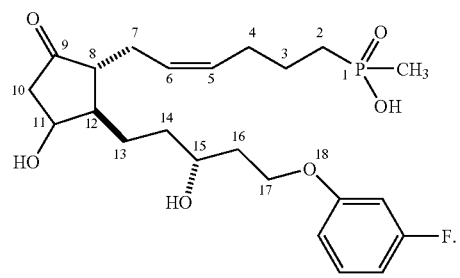

The α-configuration of the bond at position $C_{15}$ is the same in both naturally occurring $PGE_2$ and the PGE derivative of this invention, indicating that the PGE derivative is an agonist.

In contrast, naturally occurring $PGF_{2\alpha}$ has the formula:

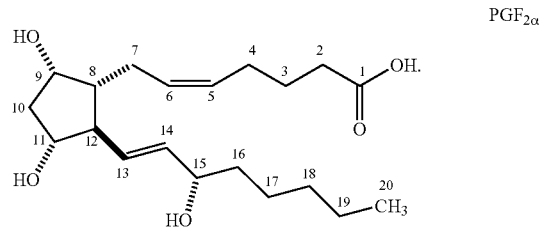

A PGF derivative according to this invention has the formula:

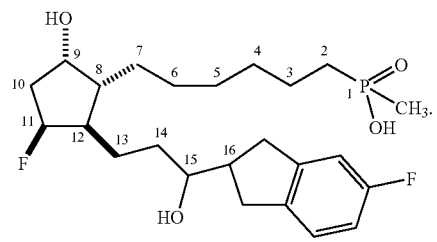

Naturally occurring $PGF_{2\alpha}$ has a bond in the alpha configuration at position $C_{11}$. The PGF derivative has a bond in the beta configuration at position $C_{11}$. The difference in bond configuration at position $C_{11}$ indicates that the PGF derivative may be an antagonist.

Selectivity of prostaglandin derivatives toward different receptors can be controlled by varying certain groups at specified positions in the prostaglandin derivative. (Numbering is based on that of naturally-occurring prostaglandins, so they must be translated to the appropriate position on the derivative.) A 9-ketone or other sp2-hybridized group is preferred for the derivative to have selectivity toward the EP receptors. A 9-hydroxyl and a 15-hydroxyl are preferred for the derivative to have selectivity toward the FP receptor. Different groups may be present at position 11, but a hydroxyl group is preferred for PGF derivatives. An 11-ketone or other sp2-hybridized group is preferred for the derivative to have selectivity toward the DP receptor. A bicyclic ring system gives compounds with selectivity toward the IP receptor. A hydrophobic cyclopentyl ring is preferred to confer selectivity to the TP receptor, and a 5,6 alkene is also preferred.

One skilled in the art would, without undue experimentation, be able to determine the receptor for which a derivative has affinity and whether the derivative is an agonist or antagonist, using the above guidelines for determining affinity, and the appropriate biological assays. One skilled in the art would be able to control the receptor for which a derivative has affinity and whether the derivative is an agonist or antagonist using the above guidelines and conventional organic syntheses.

PGE $EP_1$ agonists can be used to treat bone disorders such as osteoporosis, vascular diseases such as high blood pressure and poor vascular circulation, sexual dysfunction such as erectile dysfunction and women's sexual arousal dysfunction. $PGE_1$ agonists can also be used to enhance skin pigmentation.

$EP_1$ antagonists can be used to treat pain.

$EP_2$ agonists can be used to treat asthma and bone disorders such as osteoporosis. $EP_2$ agonists can be used to inhibit cell migration and protect against neuronal damage in the eye. $EP_2$ agonists can also be used to enhance skin pigmentation.

$EP_2$ antagonists have a diuretic effect and may be used to treat hypertension and premenstrual tension.

$EP_3$ agonists can be used to treat arthritis, bone disorders such as osteoporosis, vascular disease such as high blood pressure and poor vascular circulation. $EP_3$ agonists can also be used to enhance uterine contractions and inhibit gastric acid secretion. $EP_3$ agonists can also be used to prevent or treat, or both, hepatic diseases, renal diseases, pancreatitis, mycardial infarct, and gastric disturbances such as ulcers.

$EP_3$ antagonists can be used to control blood pressure.

$EP_4$ agonists can be used to treat arthritis, bone disorders such as osteoporosis, vascular disease such as high blood pressure and poor vascular circulation, and asthma. $EP_4$ agonists can also be used to inhibit cell migration and prevent neuronal cell death. $EP_4$ agonists can also be used to enhance skin pigmentation.

$EP_4$ antagonists have a diuretic effect and can be used to treat hypertension and premenstrual tension and to lower intraocular pressure to treat conditions such as glaucoma.

PGE derivatives suitable to use to treat the above conditions include those selected from the group consisting of:

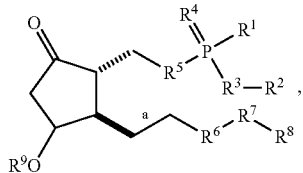

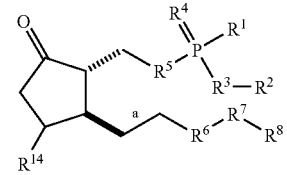

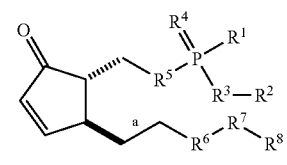

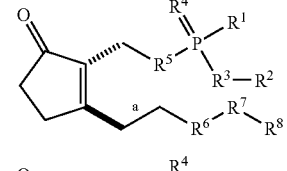

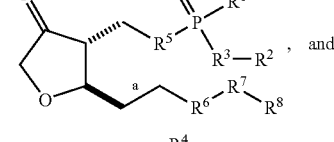

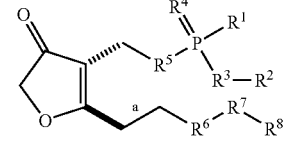

wherein bond a, $R^1$, $R^2$, $R^3$, $R^4$, $R^5$, $R^6$, $R^7$, $R^8$, $R^9$, and $R^{14}$ are as described above. One skilled in the art would be able to select appropriate PGE analogs for each condition without undue experimentation.

PGF

FP agonists can be used to treat bone disorders such as osteoporosis, ocular disorders such as glaucoma, skin disorders, circulatory disorders such as hypertension, gastrointestinal disorders, hair loss, and respiratory disorders. FP agonists can also be used for fertility control, to manage vascular diseases such as diabetic and other forms of peripheral vascular disease, to induce labor, and as nasal decongestants.

FP antagonists can be used to prevent premature labor and to prevent hyper-pigmentation of the skin.

PGF derivatives suitable to treat the above conditions include those having a structure selected from the group consisting of:

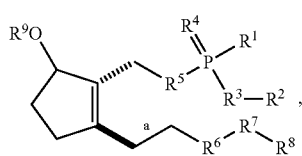

-continued

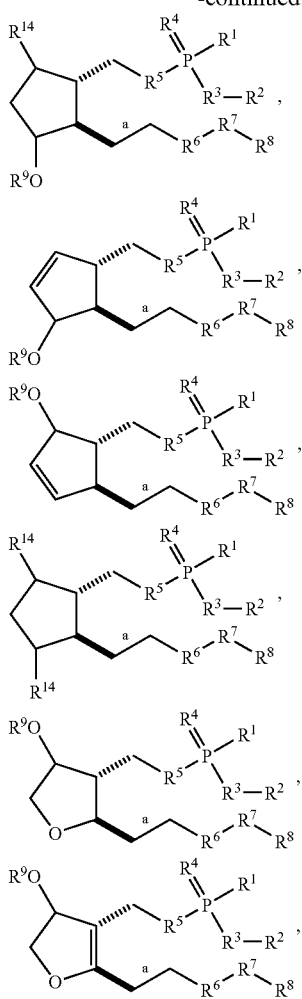

wherein bond a, $R^1$, $R^2$, $R^3$, $R^4$, $R^5$, $R^6$, $R^7$, $R^8$, $R^9$, and $R^{14}$ are as described above.

PGI

IP agonists can be used to treat vascular disorders such as peripheral vascular disease, pulmonary hypertension, high blood pressure and poor vascular circulation; reproductive disorders such as cervical immaturity, to inhibit uterine contractions, and to prevent premature delivery.

Suitable PGI derivatives for treating the above conditions include those having the structure:

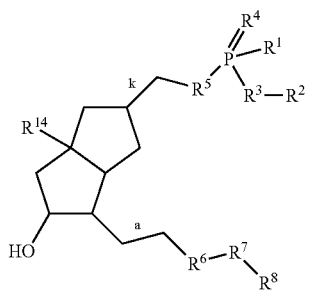

wherein bond a, bond k, $R^1$, $R^2$, $R^3$, $R^4$, $R^5$, $R^6$, $R^7$, $R^8$, and $R^{14}$ are as described above.

PGD

PGD agonists can be used to induce sleep, e.g. for treating sleeping disorders such as insomnia. PGD antagonists can be used to treat allergies. PGD derivatives suitable to treat the above conditons include those having a structure selected from the group consisting of:

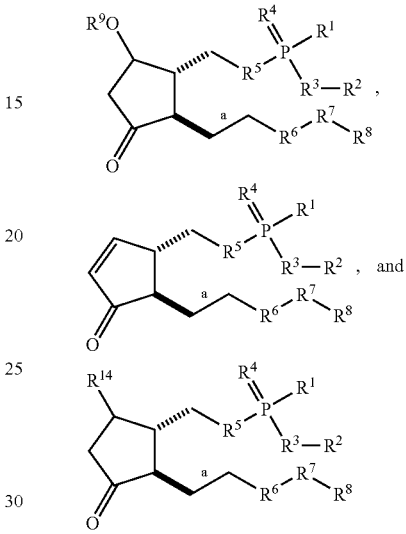

wherein bond a, $R^1$, $R^2$, $R^3$, $R^4$, $R^5$, $R^6$, $R^7$, $R^8$, $R^9$, and $R^{14}$ are as described above.

Thromboxanes

Thromboxane antagonists can be used as anti-allergy agents, to treat vascular disease, and to prevent platelet coagulation.

Suitable thromboxane antagonists for treating the above conditions include those having the structure:

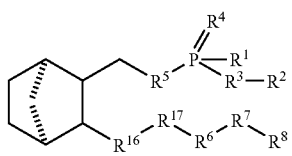

wherein $R^1$, $R^2$, $R^3$, $R^4$, $R^5$, $R^6$, $R^7$, $R^8$, $R^{14}$, $R^{16}$, and $R^{17}$ are as described above.

One skilled in the art will recognize that each of the classifications as a PGE, PGD, PGF, or PGI derivative above is merely exemplary and should not limit the scope of the invention claimed. One skilled in the art would recognize that the structures shown above may have affinity and activity towards more than one receptor. One skilled in the art would be able to determine the receptor for which a structure has affinity without undue experimentation.

The dosage of the prostaglandin derivative administered depends on a variety of factors, including the method of administration. For systemic administration, (e.g., oral, rectal, nasal, sublingual, buccal, or parenteral), typically, 0.5 mg to 300 mg, preferably 0.5 mg to 100 mg, more preferably 0.1 mg to 10 mg, of a prostaglandin derivative described above is administered per day. These dosage ranges are merely exemplary, and daily administration can be adjusted depending on various factors. The specific dosage of the prostaglandin derivative to be administered, as well as the duration of treatment, the condition being treated, and whether the treatment is topical or systemic are interdependent. The dosage and treatment regimen will also depend upon such factors as the condition being treated, the specific prostaglandin derivative used, the treatment indication, the efficacy of the compound, the personal attributes of the subject (such as, for example, weight, age, sex, and medical condition of the subject), compliance with the treatment regimen, and the presence and severity of any side effects of the treatment.

Systemic administration (e.g., parenteral, oral, sublingual, buccal and nasal) is preferably carried out four times per day for the duration of treatment. Systemic administration is preferred for treating allergies and vascular disease such high blood pressure and poor vascular circulation.

For topical administration (e.g., local application on the skin, ocular, liposome delivery systems, or iontophoresis), the topical composition is typically administered once per day for the duration of treatment. For,some conditions, 6 to 12 weeks is sufficient. Topical administration is preferred in treating conditions such as hair loss, treating skin conditions (e.g., enhancing skin pigmentation), treating ocular disorders such as glaucoma, and for local vasodilation.

EXAMPLES

These examples are intended to illustrate the invention to those skilled in the art and should not be interpreted as limiting the scope of the invention set forth in the claims. The compounds of the present invention are prepared according to methods which are known to those skilled in the art. The starting materials used in preparing the compounds of the invention are known, made by known methods, or are commercially available as a starting material.

It is recognized that the skilled artisan in the art of organic chemistry can readily carry out standard manipulations of organic compounds without further direction. Examples of such manipulations are discussed in standard texts such as J. March, *Advanced Organic Chemistry*, John Wiley & Sons, 1992.

The skilled artisan will readily appreciate that certain reactions are best carried out when other functionalitics are masked or protected in the compound, thus increasing the yield of the reaction and/or avoiding any undesirable side reactions. Often, the skilled artisan utilizes protecting groups to accomplish such increased yields or to avoid the undesired reactions. These reactions are found in the literature and are also well within the scope of the skilled artisan. Examples of many such manipulations can be found in, for example, T. Greene, *Protecting Groups in Organic Synthesis*, John Wiley & Sons, 1981.

The following abbreviations are used in the examples.
"DMAP" means dimethylaminopyridine.
"Et" means an ethyl group.
"EtOAc" means ethyl acetate.
"LAH" means lithium aluminum hydride.
"Me" means a methyl group.
"MeOH" means methanol.
"PCC" means pyridinium chlorochromate.
"TBDMS" means tert-butyldimethylsilyl.
"TBDMSOTf" means tert-butyldimethylsilyl triflate.
"THF" means tetrahydrofuran.
"TLC" means thin layer chromatography.
"TMS" means trimethylsilyl.

Example 1

Preparation of 2-decarboxy-2-bromo-13,14-dihydro-17-(3,5-difluorophenyl)-17-trinor-PGF$_{2\alpha}$11,15-bis tert-butyldimethylsilylate, 9-acetate (E1b)

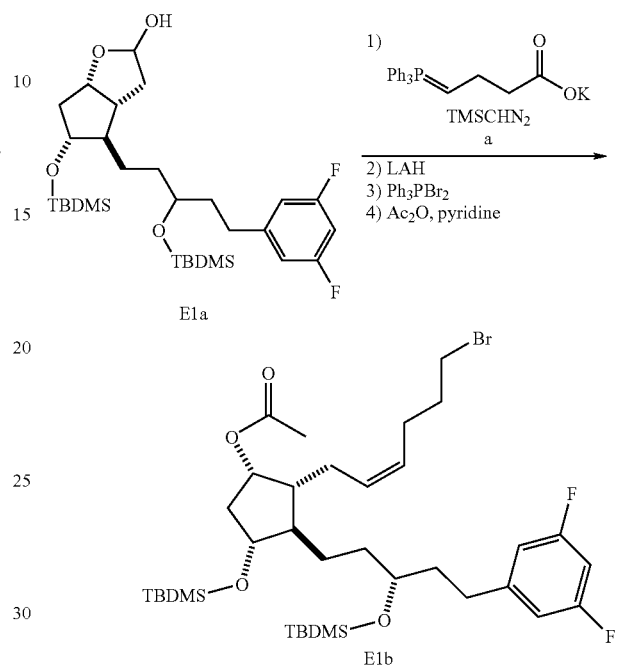

In a round bottom flask under argon the Wittig salt (a) (2.2 equiv.) is added to THF, and cooled to −78° C. Sodium hexamethyidisilazide (4.4 equiv.) is then added in one portion and the reaction is stirred for 15 minutes at −78° C. The solution is then warmed to 0° C. for two hours. The reaction mixture is recooled to −78° C. and the lactol E1a in THF is added over 10 minutes.

The lactol E1a is prepared from Corey Aldehyde in a manner analogous to that taught in U.S. Pat. No. 6,048,895. The solution is stirred at −78° C. for 1 hour and then allowed to warm to room temperature and stirred an additional 17 hours. The reaction mixture is quenched with water and the THF is removed under reduced pressure. The residue is brought up in EtOAc/hexane and washed two times with 1N HCl. The organic layer is dried with Na$_2$SO$_4$ and solvent is removed under reduced pressure. The residue is taken up in MeOH and TMS diazomethane (5 equiv.) is added slowly to the mixture. The solvent is concentrated and the residue is chromatographed on SiO$_2$ (10% EtOAc/hexanes) to provide the ester as a yellow oil.

To a solution of the ester (1 equiv.) in THF at −78° C. is added Lithium Aluminum Hydride (LAH) (1.3 equiv.) in one portion. The reaction mixture is stirred for 1 hour at −78° C. and then quenched with water. The solution is poured into CH$_2$Cl$_2$ and the aqueous layer is acidified to pH=1. The aqueous layer is re-extracted with CH$_2$Cl$_2$ and organics are combined. The organic layer is dried (Na$_2$SO$_4$) and concentrated. The residue is chromatographed on SiO$_2$ (10% EtOAc/hexanes) to provide the alcohol as a colorless oil.

To a solution of that alcohol and pyridine (1.6 equiv.) in acetonitrile is added, at 0° C., over 10 minutes solid dibromo-triphenylphosphine (1.4 equiv.). The reaction is monitored by TLC (4% EtOAc/hexanes) until complete. The solution is added to 5% EtOAc/hexanes and then the mixture is chromatographed on $SiO_2$ (5% EtOAc/hexanes) to provide the primary bromide as a colorless oil. This product is dissolved in pyridine and acetic anhydride (1.9 equiv.) and DMAP (0.05 equiv.). The reaction is stirred at 25° C. overnight. The reaction is then quenched with water. The organic layer is washed with brine, dried over $MgSO_4$, and concentrated in vacuo to give a crude product which is purified by flash chromatography on silica gel (hexanes then 1% MeOH in $CH_2Cl_2$) to 2-decarboxy-2-bromo-13,14-dihydryo-17-(3,5-difluorophenyl)-17-trinor-$PGF_{2\alpha}$11,15-bis tert-butyldimethylsilylate, 9-acetate (E1b).

Example 2

Preparation of 2-decarboxy-2-(P-methylphosphinico)-13,14-dihydryo-17-(3,5-difluorophenyl)-17-trinor-$PGE_2$ (E2c)

thylphosphinico)-13,14-dihydryo-17-(3,5-difluorophenyl)-17-trinor-$PGF_{2\alpha}$11,15-bis tert-butyldimethylsilylate, 9-acetate (E2a).

b. 2-decarboxy-2-(P-methylphosphinico)-13,14-dihydryo-17-(3,5-difluorophenyl)-17-trinor-$PGF_{1\alpha}$11,15-bis tert-butyldimethylsilylate (E2b): E2a is added to a 2.5M aqueous sodium hydroxide and is stirred at reflux for 3 hours. The mixture is then diluted with water and is washed two times with ethyl acetate. The combined washes are extracted with water. The combined aqueous phases are acidified with 1M aqueous hydrochloric acid and extracted four times with ethyl acetate. The combined extracts are dried (brine, $Na_2SO_4$) then redissolved in methylene chloride and pyridinium chlorochromate is added to effect oxidation of C-9 to the ketone. After three hours, the solution is filtered through silica, and the solvent is evaporated to give 2-decarboxy-2-(P-methylphosphinico)-13,14-dihydryo-17-(3,5-difluorophenyl)-17-trinor-$PGE_2$11,15-bis tert-butyldimethylsilylate (E2b).

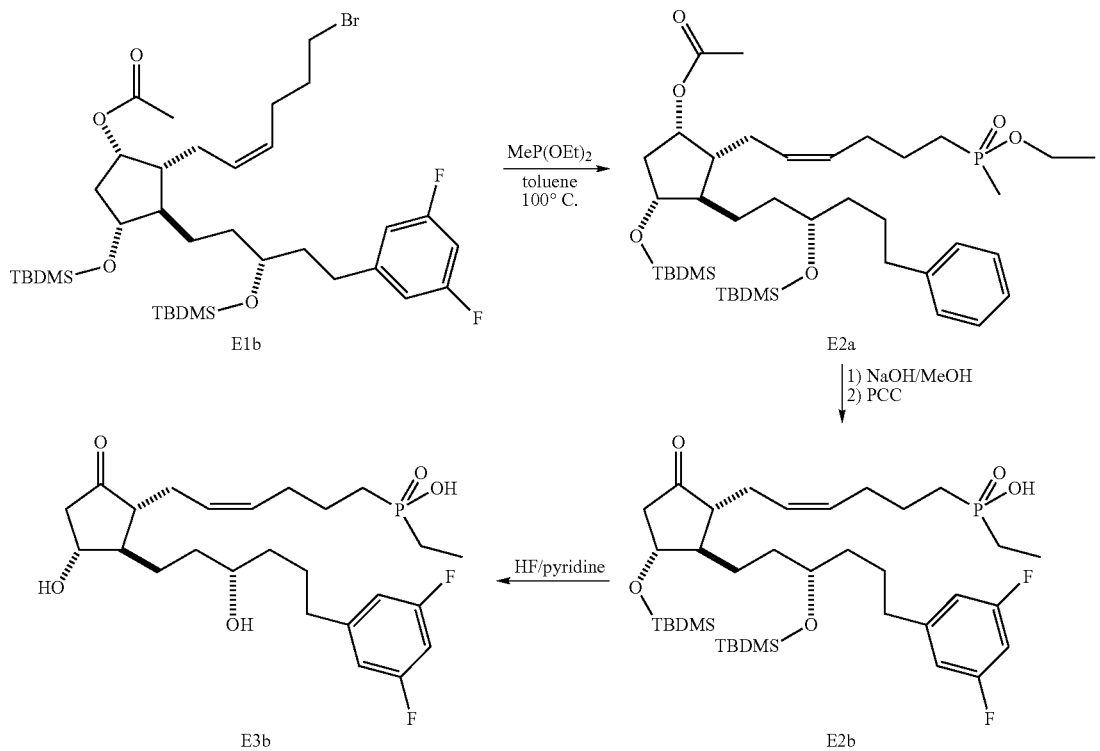

a. 2-decarboxy-2-(O-ethyl-P-methylphosphinico)-13,14-dihydryo-17-(3,5-difluorophenyl)-17-trinor-$PGF_{2\alpha}$11,15-bis tert-butyldimethylsilylate, 9-acetate (E2a): A mixture of 2-decarboxy-2-bromo-13,14-dihydryo-17-(3,5-difluorophenyl)-17-trinor-$PGF_{2\alpha}$11,15-bis tert-butyldimethylsilylate, 9-acetate, diethyl methylphosphonite (E1b) and toluene is stirred at 100° C. for 8 hours. The toluene is evaporated and the residue is purified by $SiO_2$ column chromatography (5–25% 2-propanol in 20% dichloromethane-hexane). Appropriate fractions are concentrated, diluted with water, and extracted three times with ethyl acetate. The combined extracts are washed with water, are dried (brine, $Na_2SO_4$), and are evaporated to give 2-decarboxy- 2-(O-ethyl-P-mec. 2-decarboxy-2-(P-methylphosphinico)-13,14-dihydryo-17-(3,5-difluorophenyl)-17-trinor-$PGE_2$ (E2c): The product E2b is dissolved in acetonitrile and HF/pyridine is added at zero degrees centigrade. The reaction is allowed to warm to room temperature, then the crude is concentrated by rotary evaporation, and the residue is chromatographed to yield 2-decarboxy-2-(P-methylphosphinico)-13,14-dihydryo-17-(3,5-difluorophenyl)-17-trinor-$PGE_2$ (E2c):

Examples 3–12

Using largely the procedure set forth in Examples 1 and 2 and substituting the appropriate starting materials the compounds 3–12 are made.

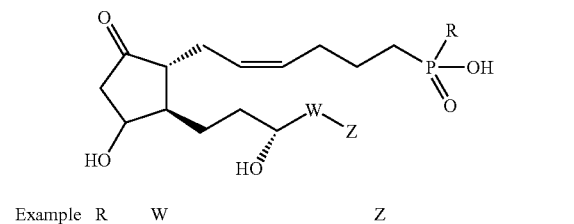

| Example | R | W | Z |
|---|---|---|---|
| 3 | Me | CH$_2$O |  |
| 4 | Et | CH=CH | 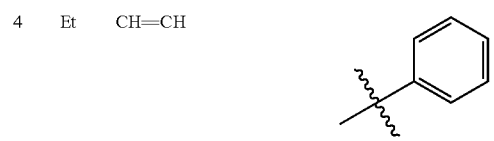 |
| 5 | Me | 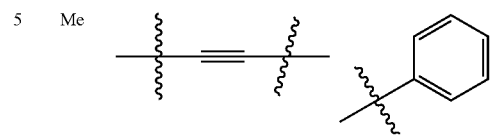 | |
| 6 | Me | —CH=C=CH— | 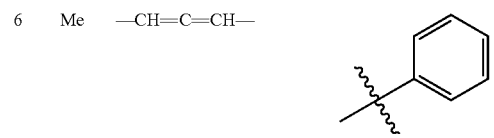 |
| 7 | Me | CH$_2$S |  |
| 8 | Me | CH$_2$O | 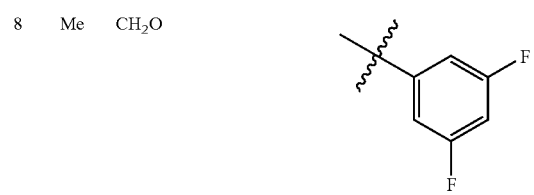 |
| 9 | Et | CH$_2$O |  |
| 10 | Me | CH$_2$CH$_2$ |  |
| 11 | Me | CH$_2$NH |  |

-continued

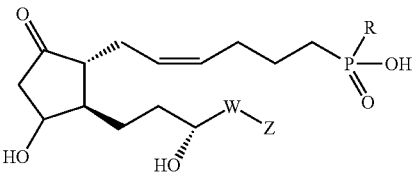

| Example | R | W | Z |
|---|---|---|---|
| 12 | H | CH$_2$NMe |  |

Examples 1–12 show that EP$_1$-specific agonists can be synthesized according to this invention.

Example 13

Preparation of 2-decarboxy-2-bromo-11-beta-fluoro-13,14-dihydryo-15-indanyl-15-pentanor-PGF$_{2\alpha}$11,15-tert-butyldimethylsilylate, 9-acetate (E1b)

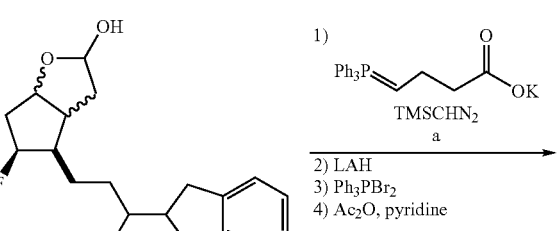

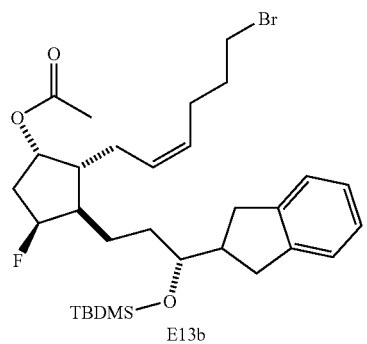

In a round bottom flask under argon the Wittig salt (a) (2.2 equiv.) is added to THF, and cooled to −78° C. Sodium hexamethyidisilazide (4.4 equiv.) is then added in one portion and the reaction is stirred for 15 minutes at −78° C. The solution is then warmed to 0° C. for two hours. The reaction mixture is cooled to −78° C. and the lactol E13a in THF is added over 10 minutes.

E13a is prepared from Corey Aldehyde in a manner analogous to that taught in PCT Publication No. WO 98/20880. The solution is stirred at −78° C. for 1 hour and then allowed to warm to room temperature and stirred an additional 17 hours. The reaction mixture is quenched with water and the THF is removed under reduced pressure. The residue is dissolved in EtOAc/hexane and washed two times with 1N HCl. The organic layer is dried with $Na_2SO_4$) and solvent is removed under reduced pressure. The residue is dissolved in MeOH and TMS diazomethane (5 equiv.) is added slowly to the mixture. The material is concentrated and it is then chromatographed on $SiO_2$ (10% EtOAc/hexanes) to provide the ester as a yellow oil.

To a solution of the ester (1 equiv.) in THF at −78° C. is added Lithium Aluminum Hydride (LAH) (1.3 equiv.) in one portion. The reaction mixture is stirred for 1 hour at −78° C. and then quenched with water. The solution is poured into $CH_2Cl_2$ and the aqueous layer is acidified to pH=1. The aqueous layer is re-extracted with $CH_2Cl_2$ and organics are combined. The organic layer is dried ($Na_2SO_4$) and concentrated. The residue is chromatographed on $SiO_2$ (10% EtOAc/hexanes) to provide the alcohol as a colorless oil. To a solution of that alcohol and pyridine (1.6 equiv.) in acetonitrile is added, at 0° C., over 10 min solid dibromotriphenylphosphine (1.4 equiv.). The reaction is monitored by TLC (4% EtOAc/hexanes) until complete. The solution is added to 5% EtOAc/hexanes and then the mixture is chromatographed on $SiO_2$ (5% EtOAc/hexanes) to provide the primary bromide as a colorless oil. This product is dissolved in pyridine and acetic anhydride (1.9 equiv.) and DMAP (0.05 equiv.). The reaction is stirred at 25° C. overnight. The reaction is then quenched with water. The organic layer is washed with brine, dried over $MgSO_4$, and concentrated in vacuo to give a crude product which is purified by flash chromatography on silica gel (hexanes then 1% MeOH in $CH_2Cl_2$) to 2-decarboxy-2-bromo-11-beta-fluoro-13,14-dihydryo-15-indanyl-15-pentanor-$PGF_{2\alpha}$15-tert-butyldimethylsilylate, 9-acetate (E13b).

Example 14

Preparation of 2-decarboxy-2-(P-methylphosphinico)-13,14-dihydryo-15-indanyl-15-pentanor-$PGF_{2a}$ (E14b)

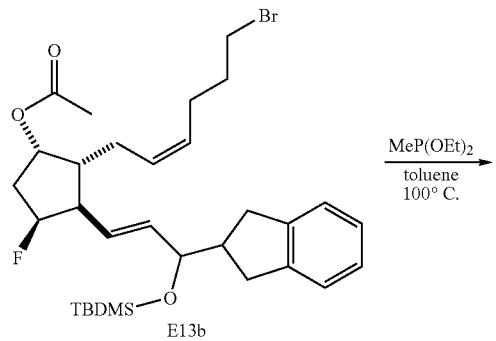

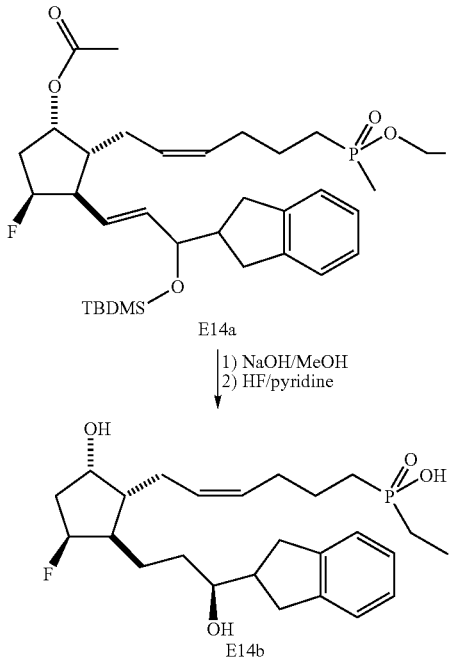

a. 2-decarboxy-2-(O-ethyl-P-methylphosphinico)-13,14-dihydryo-15-indanyl-15-pentanor-$PGF_{2\alpha}$15-tert-butyldimethylsilylate, 9-acetate (E14a): A mixture of 2-decarboxy-2-bromo-13,14-dihydryo-15-indanyl-15-pentanor-$PGF_{2\alpha}$15-tert-butyldimethylsilylate 9-acetate, diethyl methylphosphonite (E13b) and toluene is stirred at 100° C. for 8 hours. The toluene is evaporated and the residue is purified by $SiO_2$ column chromatography (5–25% 2-propanol in 20% dichloromethane-hexane). Appropriate fractions are concentrated, diluted with water, and extracted three times with ethyl acetate. The combined extracts are washed with water, are dried (brine, $Na_2SO_4$), and are evaporated to give 2-decarboxy-2-(O-ethyl-P-methyl phosphinico)-13,14-dihydryo-15-indanyl-15-pentanor-$PGF_{2\alpha}$15-tert-butyldimethylsilylate, 9-acetate (E14a).

b. 2-decarboxy-2-(P-methylphosphinico)-13,14-dihydryo-15-indanyl-15-pentanor-$PGF_{2\alpha}$ (E14b): E14a is added to a 2.5M aqueous sodium hydroxide and is stirred at reflux for 3 hours. The mixture is then diluted with water and is washed two times with ethyl acetate. The combined washes are extracted with water. The combined aqueous phases are acidified with 1M aqueous hydrochloric acid and extracted four times with ethyl acetate. The combined extracts are dried (brine, $Na_2SO_4$) then re dissolved in acetonitrile and HF/pyridine is added at zero degrees centigrade. The reaction is allowed to warm to room temperature, then the crude is concentrated by rotary evaporation. The residue is chromatographed to yield 2-decarboxy-2-(P-methylphosphinico)-13,14-dihydro-15-indanyl-15-pentanor-$PGF_{2\alpha}$ (E14b).

Examples 15–26

Using largely the procedure set forth in Examples 13 and 14 and substituting the appropriate starting materials the compounds 15–26 are made.

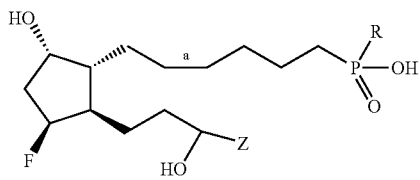
| Example | R | a | Z |
|---|---|---|---|
| 15 | Me | CH$_2$CH$_2$ | 5-fluoro-2,3-dihydro-1H-inden-2-yl |
| 16 | Et | CH=CH | 5-fluoro-2,3-dihydro-1H-inden-2-yl |
| 17 | Me | —C≡C— | benzo[b]thiophen-2-yl |
| 18 | Me | —CH=C=CH— | 2,3-dihydro-1H-inden-2-yl |
| 19 | Me | CH$_2$CH$_2$ | 2,3-dihydro-1H-inden-2-yl |
| 20 | Me | CH=CH | 2,3-dihydro-1H-inden-2-yl |
| 21 | Et | CH=CH | benzo[b]thiophen-2-yl |
| 22 | Me | CH$_2$CH$_2$ | benzo[b]thiophen-2-yl |
| 23 | Me | CH=CH | 7-fluorobenzo[b]thiophen-2-yl |
| 24 | H | CH=CH | benzofuran-2-yl |
| 25 | Me | CH$_2$CH$_2$ | 6-fluorobenzofuran-2-yl |

-continued

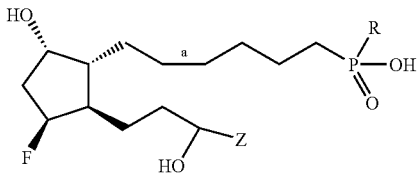

| Example | R  | a     | Z |
|---------|----|-------|---|
| 26      | Me | CH=CH | benzofuran-2-yl |

Examples 13–26 show that FP-specific antagonists can be prepared according to this invention.

Example 27

Preparation of 3-(6-iodo)hex-3-enyl)-2-morpholin-4-yl-4-((4-phenyl)phenyl)methoxy)cyclopentan-1-ol TBDMS ether (E27b)

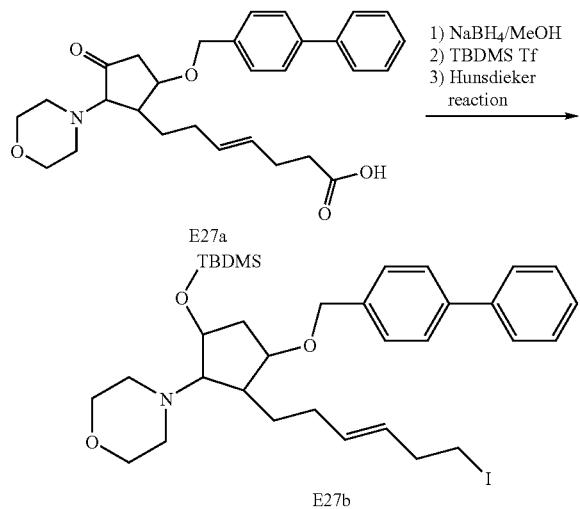

In a round bottom flask under argon the acid (E27a) (1 equiv.) is added to MeOH, and cooled to −10° C. Sodium borohydride (1.5 equiv.) is then added in one portion and the reaction is stirred for 15 minutes at −10° C. The solution is then warmed to room temperature for two hours. Acetic acid is added and the methanol removed under vacuum. The crude material is resuspended in dichloromethane and triethylamine (1.1 equiv.) is added. The solution is stirred at −78° C. while TBDMSTf (1.05 equiv.) is added dropwise. The reaction is stirred for 1 hour and then allowed to warm to room temperature and stirred an additional 1 hour. The reaction mixture is quenched with water and the methylene chloride is removed under reduced pressure. The residue is dissolved along with oxalyl chloride and dimethylformamide in dichloromethane and is allowed to stand at room temperature for 30 minutes and is then concentrated. The residue is taken up in dichloromethane. Separately, a mixture of the sodium salt of N-hydroxypyridine-2-thione, DMAP, and dichloromethane under argon is brought to reflux by irradiation with a 250 Watt General Electric floodlamp. To this mixture is added 1,1,1-trifluoro-2-iodo-ethane, followed by the solution of acid chloride which is added over 15 minutes. Irradiation is continued for 45 minutes and then the mixture is concentrated and purified by dry-flash column chromatography to give the 1-nor-primary iodide E27b.

Example 28

Preparation of 3-(6-(methyl(hydroxyphosphoryl))hex-3-enyl)-2-morpholin-4-yl-4-((4-phenyl)phenyl)methoxy)cyclopentan-1-one (E28c)

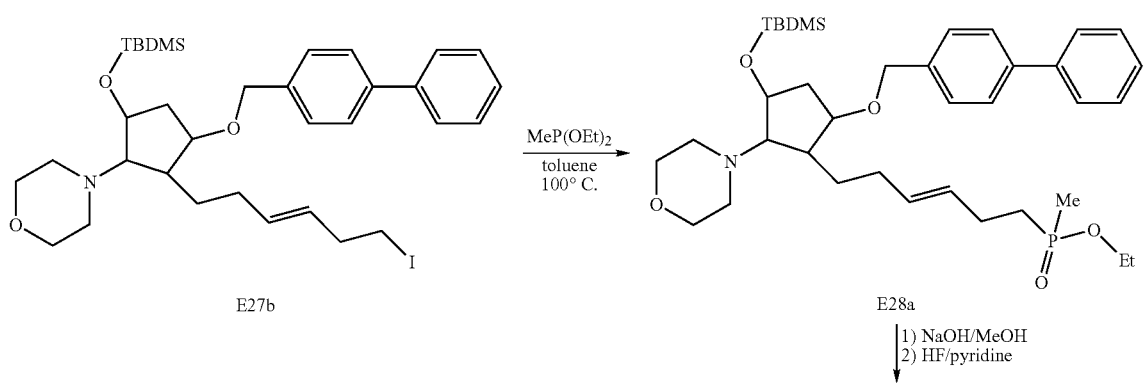

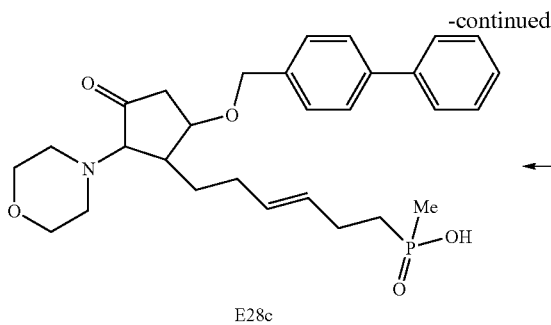
E28c

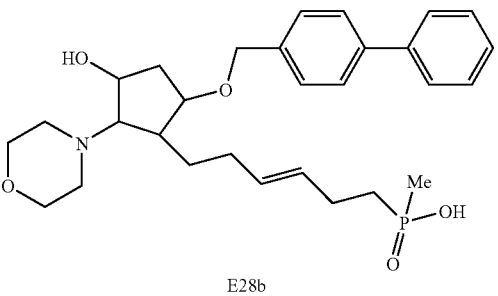
E28b a. Preparation of 3-(6-(methyl(ethoxyphosphoryl))hex-3-enyl)-2-morpholin-4-yl-4-((4-phenyl)phenyl)methoxy)cyclopentan-1-ol; TBDMS ether (E28a): A mixture of E27b and toluene is stirred at 100° C. for 8 hours. The toluene is evaporated and the residue is purified by $SiO_2$ column chromatography (5–25% 2-propanol in 20% dichloromethane-hexane). Appropriate fractions are concentrated, diluted with water, and extracted three times with ethyl acetate. The combined extracts are washed with water, are dried (brine, $Na_2SO_4$), and are evaporated to give 3-(6-(methyl(ethoxyphosphoryl))hex-3-enyl)-2-morpholin-4-yl-4-((4-phenyl)phenyl)methoxy)cyclopentan-1-ol; TBDMS ether (E28a):

b. Preparation of 3-(6-(methyl(hydroxyphosphoryl))hex-3-enyl)-2-morpholin-4-yl-4-((4-phenyl)phenyl)methoxy)cyclopentan-1-ol; (E28b): E28a is added to a 2.5M aqueous sodium hydroxide and is stirred at reflux for 3 hours. The mixture is then diluted with water and is washed two times with ethyl acetate. The combined washes are extracted with water. The combined aqueous phases are acidified with 1M aqueous hydrochloric acid and extracted four times with ethyl acetate. The combined extracts are dried (brine, $Na_2SO_4$) then re dissolved in acetonitrile and HF/pyridine is added at zero degrees centigrade. The reaction is allowed to warm to room temperature, then the crude is concentrated by rotary evaporation. The residue is chromatographed to 3-(6-(methyl)hydroxyphosphoryl))hex-3-enyl)-2-morpholin-4-yl-4-((4-phenyl)phenyl)methoxy)cyclopentan-1-ol; (E28b).

b. Preparation of 3-(6-(methyl(hydroxyphosphoryl))hex-3-enyl)-2-morpholin-4-yl-4-((4-phenyl)phenyl)methoxy)cyclopentan-1-one; (E28c): E28b is added to a solution of dichloromethane and PCC is slowly added along with molecular sieves. The solution is stirred and monitored by TLC until the complete consumption of starting material. The solution is then filtered thru Celite and Fluorosil and purified, if necessary by silica gel chromatography yielding 3-(6-(methyl(hydroxyphosphoryl))hex-3-enyl)-2-morpholin-4-yl-4-((4-phenyl)phenyl)methoxy)cyclopentan-1-one; (E28c):.

Examples 29–35

Using largely the procedure set forth in Examples 27 and 28 and substituting the appropriate starting materials the compounds 29–35, having the formula below, are made.

| Example | R | a | R' | R'' |
|---|---|---|---|---|
| 29 | Me | CH₂CH₂ | H | H |
| 30 | Et | CH=CH | H | 3,5-diF |
| 31 | Me | —C≡C— | H | H |
| 32 | Me | —CH=C=CH— | H | 3,5-diF |
| 33 | Me | CH₂CH₂ | 2-F | H |
| 34 | Me | CH=CH | 3-F | H |
| 35 | Et | CH=CH | 2,2'-diF | H |

Examples 27–35 show that EP4 antagonists can be synthesized according to this invention.

Example 36

Preparation of 7-methoxy-6-(3-methoxyoctyl)-2-oxabicyclo[3.3.0]octan-3-ol (E36b)

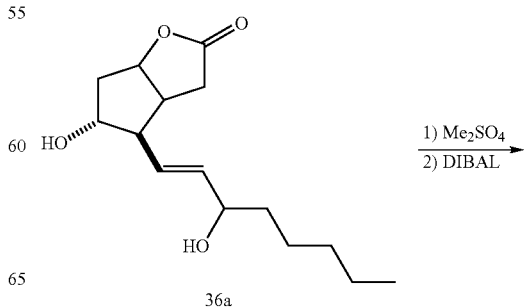
36a

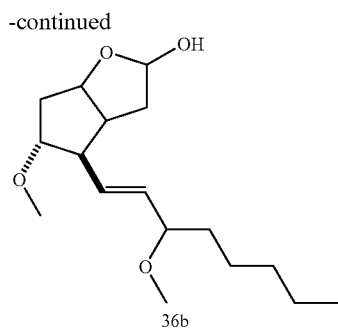

In a round bottom flask under argon the commercially-available Corey lactone (E36a) (available from Cayman Chemical or Aldrich Chemical) is placed in an inert solvent. Dimethyl sulfate (2 equivalents) is added dropwise, and the mixture is then stirred for 15 hours. The solution is then warmed for two hours. The reaction mixture is cooled and the lactone is isolated by chromatography, then cooled to −78° C. for 1 hour and DIBAL is added to effect reduction to the lactol, E36b. The material is concentrated and then taken to the next step as soon as possible without further purification.

Example 37

Preparation of 2-decarboxy-2-bromo-PGF$_{1\alpha}$11,15-dimethoxy, 9-tert-butyldimethylsilylate, (E37a)

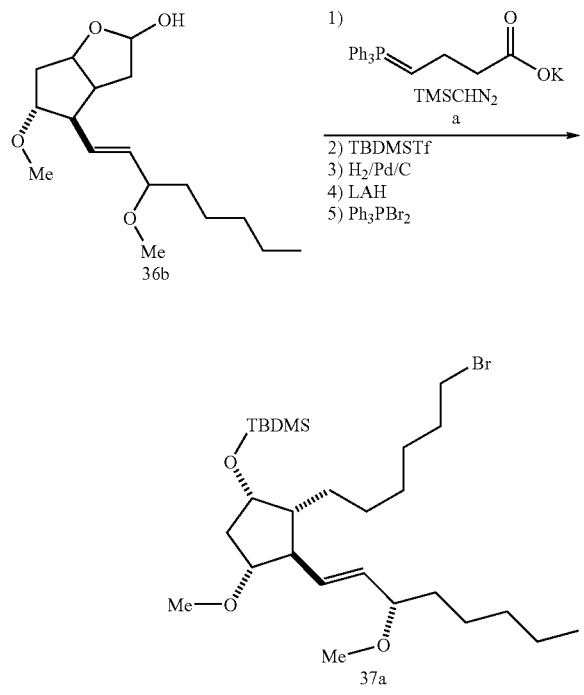

In a round bottom flask under argon the Wittig salt (a) (2.2 equiv.) is added to THF, and cooled to −78° C. Sodium hexamethyldisilazide (4.4 equiv.) is then added in one portion and the reaction is stirred for 15 minutes at −78° C. The solution is then warmed to 0° C. for two hours. The reaction mixture is recooled to −78° C. and the lactol E36b in THF is added over 10 minutes. The solution is stirred at −78° C. for 1 hour and then allowed to warm to room temperature and stirred an additional 17 hours. The reaction mixture is quenched with water and the THF is removed under reduced pressure. The residue is brought up in EtOAc/hexane and washed two times with 1N HCl. The organic layer is dried with $Na_2SO_4$ and solvent is removed under reduced pressure. The residue is taken up in MeOH and TMS diazomethane (5 equiv.) is added slowly to the mixture. The solvent is concentrated and the residue is chromatographed on $SiO_2$ (10% EtOAc/hexanes) to provide the ester as a yellow oil.

To a solution of the ester (1 equiv.) in $CH_2Cl_2$ is added dropwise at −78° C.: 2,6-lutidine (1.9 equiv.) followed by TBDMSOTf (1.8 equiv.). The reaction is stirred for 30 minutes at −78° C. and then warmed to 25° C. overnight. The reaction is quenched with water. The organic layer is then washed with water, dried over $MgSO_4$, and concentrated in vacuo to give a crude isolate which is subjected to flash chromatography on silica gel eluting with hexanes then 1% MeOH in $CH_2Cl_2$ to give the 9-silyl-protected product. This product is dissolved in ethyl acetate and hydrogenated carefully with hydrogen gas over Pd on C (5%). The product is filtered, then the ethyl acetate is removed in vacuo, and to the residue in THF at −78° C. is added Lithium Aluminum Hydride (LAH) (1.3 equiv.) in one portion. The reaction mixture is stirred for 1 hour at −78° C. and then quenched with water. The solution is poured into $CH_2Cl_2$ and the aqueous layer is acidified to pH=1. The aqueous layer is re-extracted with $CH_2Cl_2$ and organics are combined. The organic layer is dried ($Na_2SO_4$) and concentrated. The residue is chromatographed on $SiO_2$ (10% EtOAc/hexanes) to provide the alcohol as a colorless oil. To a solution of that alcohol and pyridine (1.6 equiv.) in acetonitrile is added, at 0° C., over 10 min solid dibromo-triphenylphosphine (1.4 equiv.). The reaction is monitored by TLC (4% EtOAc/hexanes) until complete. The solution is added to 5% EtOAc/hexanes and then the mixture is chromatographed on $SiO_2$ (5% EtOAc/hexanes) to provide the primary bromide as a colorless oil. This product is dissolved in pyridine and acetic anhydride (1.9 equiv.) and DMAP (0.05 equiv.). The reaction is stirred at 25° C. overnight. The reaction is then quenched with water. The organic layer is washed with brine, dried over $MgSO_4$, and concentrated in vacuo to give a crude product which is purified by flash chromatography on silica gel (hexanes then 1% MeOH in $CH_2Cl_2$) to give 2-decarboxy-2-bromo-PGF$_{1\alpha}$11,15-dimethoxy, 9-tert-butyldimethylsilylate, (E37a).

Example 38

Preparation of 2-decarboxy-2-(P-methylphosphinico)-13,14-dihydryo-17-(3,5-difluorophenyl)-17-trinor-PGE$_2$ (E2c)

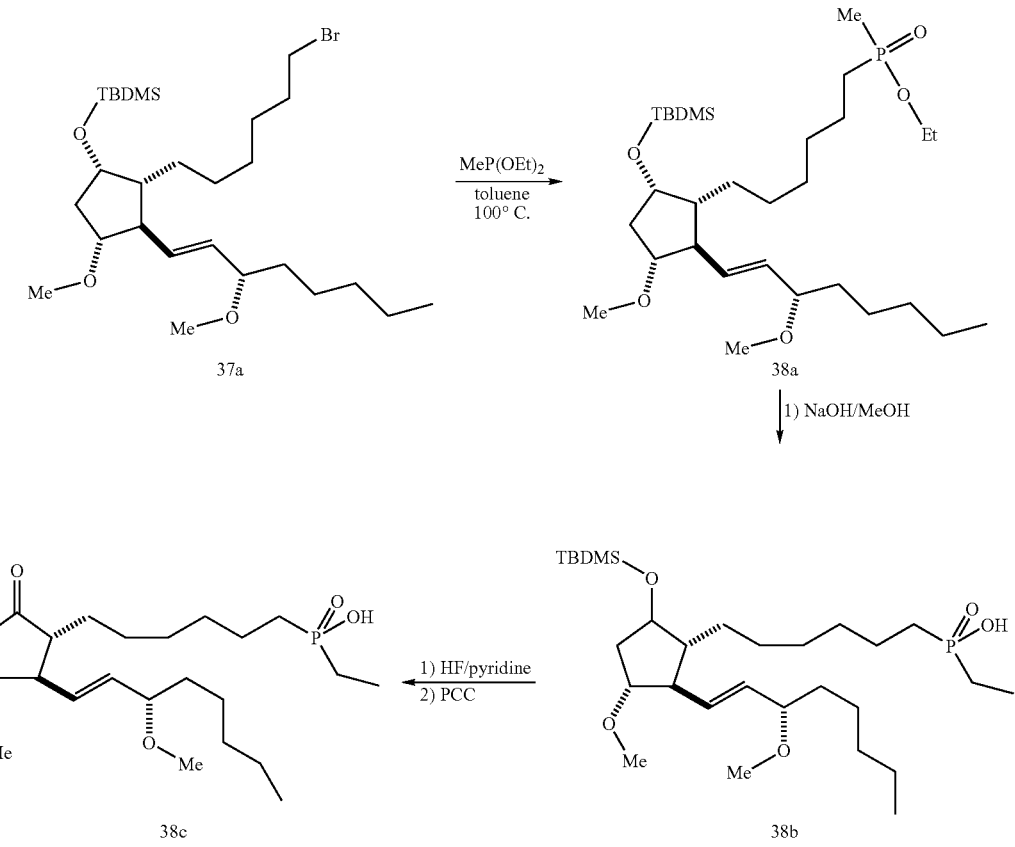

a. 2-decarboxy-2-(O-ethyl-P-methylphosphinico)-13,14-dihydryo-17-(3,5-difluorophenyl)-17-trinor-PGF$_{2\alpha}$11,15-bis tert-butyldimethylsilylate, 9-acetate (E38a): A mixture of 2-decarboxy-2-bromo-PGF$_{1\alpha}$11,15-dimethoxy, 9-tert-butyldimethylsilylate, (E37a), diethyl methylphosphonite, and toluene is stirred at 100° C. for 8 hours. The toluene is evaporated and the residue is purified by SiO$_2$ column chromatography (5–25% 2-propanol in 20% dichloromethane-hexane). Appropriate fractions are concentrated, diluted with water, and extracted three times with ethyl acetate. The combined extracts are washed with water, are dried (brine, Na$_2$SO$_4$), and are evaporated to give 2-decarboxy-2-(O-ethyl-P-methylphosphinico)-PGF$_{1\alpha}$111,15-dimethoxy, 9-tert-butyldimethylsilylate (E38a).

b. 2-decarboxy-2-(P-methylphosphinico)-11,15-dimethoxy PGF$_{1\alpha}$9-tert-butyl dimethyl silylate (E38b): E38a is added to a 2.5M aqueous sodium hydroxide and is stirred at reflux for 3 hours. The mixture is then diluted with water and is washed two times with ethyl acetate. The combined washes are extracted with water. The combined aqueous phases are acidified with 1M aqueous hydrochloric acid and extracted four times with ethyl acetate. The combined extracts are dried (brine, Na$_2$SO$_4$) then chromatographed on silica gel to yield 2-decarboxy-2-(P-methylphosphinico)-11,15-dimethoxy PGF$_{1\alpha}$9-tert-butyl dimethyl silylate (E38b).

c. 2-decarboxy-2-(P-methylphosphinico)-11,15-dimethoxy-PGE$_2$ (E38c): The product E38b is dissolved in acetonitrile and HF/pyridine is added at zero degrees centigrade. The reaction is allowed to warm to room temperature, then the crude is concentrated by rotary evaporation, and the residue is chromatographed to yield the free acohol, which is dissolved in methylene chloride and PCC is added. When the reaction is complete by TLS, the crude mixture is filtered through Fluorosil, and the residue is concentrated to yield 2-decarboxy-2-(P-methylphosphinico)-11,15-dimethoxy-PGE$_2$ (E38c).

Examples 39–52

Using largely the procedure set forth in Examples 36 to 38 and substituting the appropriate starting materials the compounds 39–52 are made.

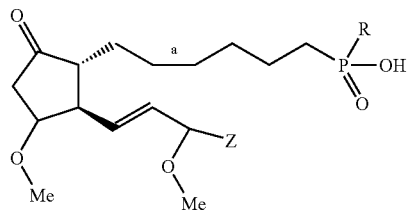
| Example | R | a | Z |
|---|---|---|---|
| 39 | Me | CH₂CH₂ | -CH₂-C₆H₅-phenyl (benzyl-CH₂) |
| 40 | Et | CH=CH | -CH(benzyl) |
| 41 | Me | -C≡C- | -CH₂-S-C₆H₅ |
| 42 | Me | -CH=C=CH- | -CH₂-O-C₆H₅ |
| 43 | Me | CH₂CH₂ | -(CH₂)₃-C₆H₅ |
| 44 | Me | CH=CH | 2-indanyl |
| 45 | Et | CH=CH | -CH₂-S-C₆H₅ |
| 46 | Me | CH₂CH₂ | -CH₂-S-C₆H₅ |
| 47 | Me | CH₂CH₂ | -CH₂-S-(2-F-C₆H₄) |
| 48 | H | CH=CH | -CH₂-O-C₆H₅ |

-continued

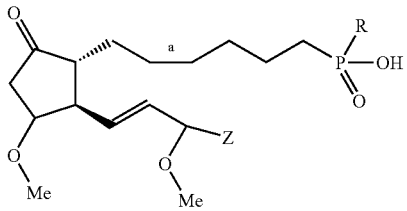

| Example | R | a | Z |
|---|---|---|---|
| 49 | Me | CH₂CH₂ | -CH₂-O-C₆H₄-F (meta) |
| 50 | Me | CH₂CH₂ | -CH₂-O-CH₂CH₂CH₂-O-CH₃ |

Examples 36–50 show that EP₃-specific agonists can be synthesized according to this invention. They are made in analogy to Examples 1 and 2 above, or when available, they can be made directly from the commercially-available prostaglandins or intermediates, such as in Example 36.

Example 51

Preparation of (4Z)-6-[(1R,2S,3S,4S)-3-(5-hydroxybenzo[b]thiophen-3-carbonylamino)bicyclo[2.2.1]-4-hexenyl-P-methyl-phosphinic acid (E51B) sodium salt

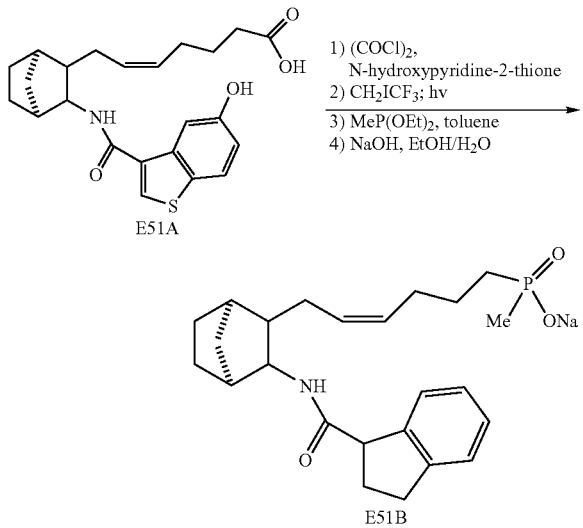

a. A mixture of (5Z)-7-[(1R,2S,3S,4S)-3-(5-hydroxybenzo[b]thiophen-3-carbonylamino)bicyclo[2.2.1]-5-heptenoic acid (E51A) (available as described in WO99/15502-A1), oxalyl chloride and dimethylformamide in dichloromethane is allowed to stand at room temperature for 30 minutes and is then concentrated. The residue is taken up in dichloromethane. Separately, a mixture of the sodium salt of N-hydroxypyridine-2-thione, DMAP, and dichloromethane under argon is brought to reflux by irradiation with a 250 Watt General Electric floodlamp. To this mixture is added 1,1,1-trifluoro-2-iodoethane, followed by the solution of acid chloride which is added over 15 minutes. Irradiation is continued for 45 minutes and then the mixture is concentrated and purified by dry-flash column chromatography to give the 1-nor-primary iodide A mixture of the iodide, diethyl methylphosphonite, and toluene is stirred at 100° C. for 7 hours. The solvents are evaporated and the residue is purified by SiO₂ column chromatography (5–25% 2-propanol in 20% dichloromethane-hexane). Appropriate fractions are concentrated, diluted with water and extracted with ethyl acetate three times. The combined extracts are washed with water, dried (brine, Na₂SO₄), and evaporated to yield the phosphinic acid ester.

A mixture of the phosphinic acid ester, 95% ethanol, and 2.5M aqueous sodium hydroxide is stirred at reflux for 3 hours. The mixture is diluted with water and is washed with ethyl acetate two times. The combined washes are extracted with water. The combined aqueous phases are acidified with 1M aqueous hydrochloric acid and extracted with ethyl acetate four times. The combined extracts are dried (brine, Na₂SO₄) and are evaporated. The residue is taken up in methanol and stirred with Amberlite CG-50 (Na⁺ form) for 15 minutes. The resin is removed by filtration and the filtrate is concentrated to give (4Z)-6-[(1R,2S,3S,4S)-3-(5-hydroxybenzo[b]thiophen-3-carbonylamino)bicyclo[2.2.1]-4-hexenyl-P-methyl-phosphinic acid sodium salt, (E51b).

Examples 52–60

Examples 52–60 are prepared using substantially the same procedure as that described in Example 51, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Examples 52–60

| Example | R₁ | X | R₂ |
|---|---|---|---|
| 52 | Me | C=O | benzofuran-OH |
| 53 | Et | SO₂ | benzothiophene-OH |
| 54 | Me | SO₂ | 2-Me-4-Cl-phenyl |
| 55 | iPr | C=O | 2-Me-4-Cl-phenyl |
| 56 | Me | SO₂ | 4-Cl-phenyl |
| 57 | Me | C=O | 4-CF₃-phenyl |
| 58 | Et | SO₂ | 2,4-diF-phenyl |
| 59 | Pr | SO₂ | benzothiophene-OH |
| 60 | Me | C=O | indanyl-OH |

For some structures, it is advantageous to construct a complete prostaglandin using known means and then transform the completed prostaglandin into the phosphinic acid using substantially the same means as Example 51. The skilled artisan will recognize when interfering functionality would make it desirable to do so.

Examples 51–60 show that TP antagonists can be prepared according to this invention. The TP-specific antagonists are made in analogy to examples 1 and 2 above, or when available, they can be made directly from the commercially-available prostaglandins or intermediates, such as in Example 51.

Example 61

Preparation of (E61b)

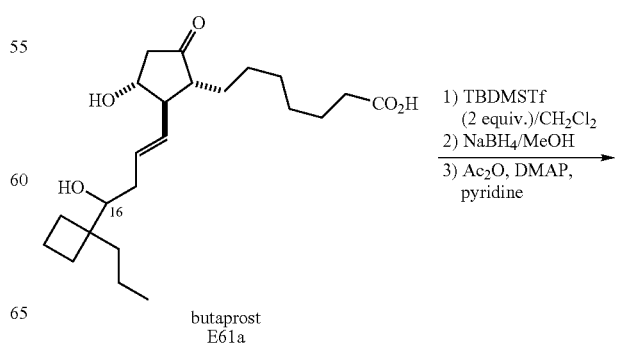

butaprost
E61a

1) TBDMSTf (2 equiv.)/CH₂Cl₂
2) NaBH₄/MeOH
3) Ac₂O, DMAP, pyridine

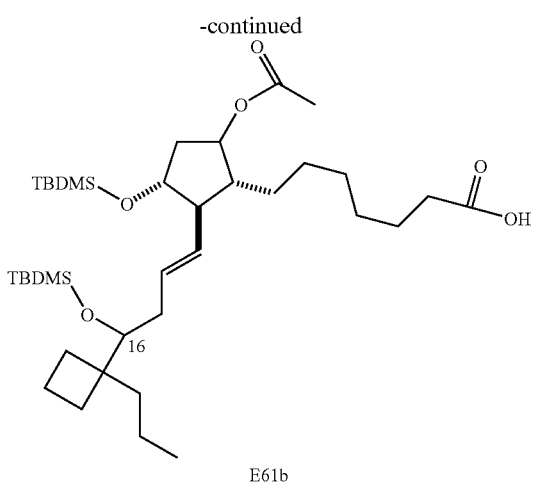

E61b

E61b: To a solution of butaprost (E61a) (1 equiv.) in CH$_2$Cl$_2$ at −78° C. is added 2,6 lutidine (2.3 equiv.) dropwise over 15 minutes. The solution is kept at 0° C., and TBDMS Triflate (2.2 equiv.) in CH$_2$Cl$_2$ is added dropwise over 15 minutes. The reaction is warmed gradually to room temperature and stirred for 15 hours. Aqueous 1N HCl is added and the layers are quickly separated. The water layer is extracted once with CH$_2$Cl$_2$ and the organic layers are combined. The combined organic layer is washed with brine, dried (over solid Na$_2$SO$_4$) and concentrated. The residue is chromatographed on SiO$_2$ (5% EtOAc/hexanes) to provide the bis-silylated ester as an oil. To a solution of this oil (1 equiv.) in methanol at 0° C. is added Sodium Borohydride (NaBH$_4$) (1.3 equiv.) in one portion. The reaction mixture is stirred for 1 hour at 0° C. and then concentrated, and the concentrate partitioned between water and ethyl acetate (EtOAc). The aqueous layer is re-extracted once with EtOAc and the organics are combined. The organic layer is then dried (Na$_2$SO$_4$) and concentrated. The residue is chromatographed on silica gel (10% EtOAc/hexanes) to provide a mixture of C-9 alcohols as a colorless oil. This mixture is dissolved in pyridine and acetic anhydride (1.8 equiv.) and DMAP (0.05 equiv.). The reaction is stirred at 25° C. overnight. The reaction is then quenched with water. The organic layer is washed with brine, dried over MgSO$_4$, and concentrated in vacuo to give a crude product which is purified by flash chromatography on silica gel (hexanes then 1% MeOH in CH$_2$Cl$_2$) to give the bis-t-butyldimethylsilylate, 9-acetate (E61b).

Example 62

Preparation of 2-nor-2-P-methylphosphinico butaprost (E62b)

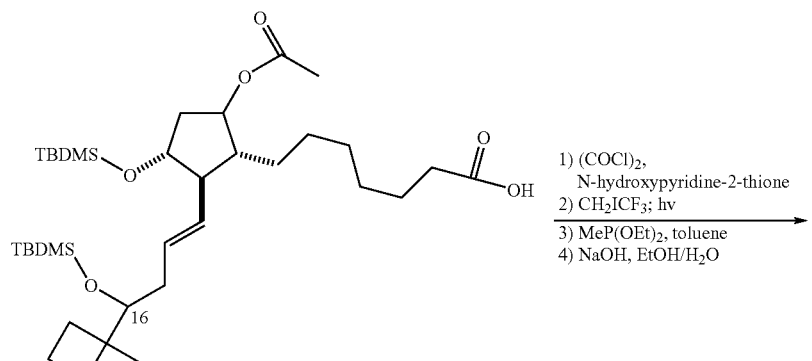

E61b 1) (COCl)$_2$, N-hydroxypyridine-2-thione
2) CH$_2$ICF$_3$; hv
3) MeP(OEt)$_2$, toluene
4) NaOH, EtOH/H$_2$O

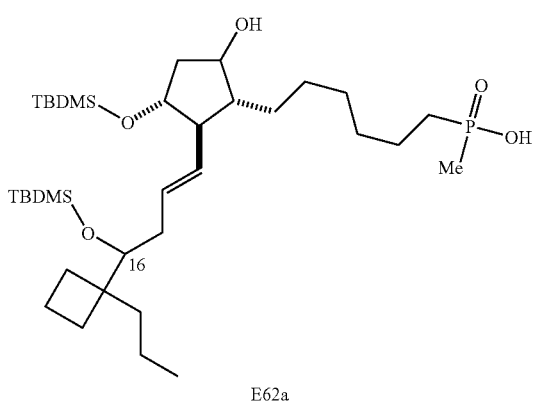

E62a a. A mixture of protected, reduced butaprost (E61b); oxalyl chloride and dimethylformamide in dichloromethane is allowed to stand at room temperature for 30 minutes and is then concentrated. The residue is taken up in dichloromethane. Separately, a mixture of the sodium salt of N-hydroxypyridine-2-thione, DMAP, and dichloromethane under argon is brought to reflux by irradiation with a 250 Watt General Electric floodlamp. To this mixture is added 1,1,1-trifluoro-2-iodoethane, followed by the solution of acid chloride which is added over 15 minutes. Irradiation is continued for 45 minutes and then the mixture is concentrated and purified by dry-flash column chromatography to give the 1-nor-primary iodide A mixture of the iodide, diethyl methylphosphonite, and toluene is stirred at 100° C. for 7 hours. The solvents are evaporated and the residue is purified by SiO$_2$ column chromatography (5–25% 2-propanol in 20% dichloromethane-hexane). Appropriate fractions are concentrated, diluted with water and extracted with ethyl acetate three times. The combined extracts are washed with water, dried (brine, Na$_2$SO$_4$), and evaporated to yield the phosphinic acid ester.

A mixture of the phosphinic acid ester, 95% ethanol, and 2.5M aqueous sodium hydroxide is stirred at reflux for 3 hours. The mixture is diluted with water and is washed with ethyl acetate two times. The combined washes are extracted with water. The combined aqueous phases are acidified with 1M aqueous hydrochloric acid and extracted with ethyl acetate four times. The combined extracts are dried (brine, Na$_2$SO$_4$) and are evaporated. The residue is taken up in methanol and stirred with Amberlite CG-50 (Na$^+$ form) for 15 minutes. The resin is removed by filtration and the filtrate is brought to a pH=3.0, then concentrated to give 5-(4-t-butyldimethylsilyloxy-4-(1-propylcyclobutyl)but-1-enyl)4-(6-(P-methyl(hydroxyphosphoryl))hexyl)3-t-butyldimethyl-silyloxycyclopentan-1-ol (E62a).

Example 63

Preparation of E63a

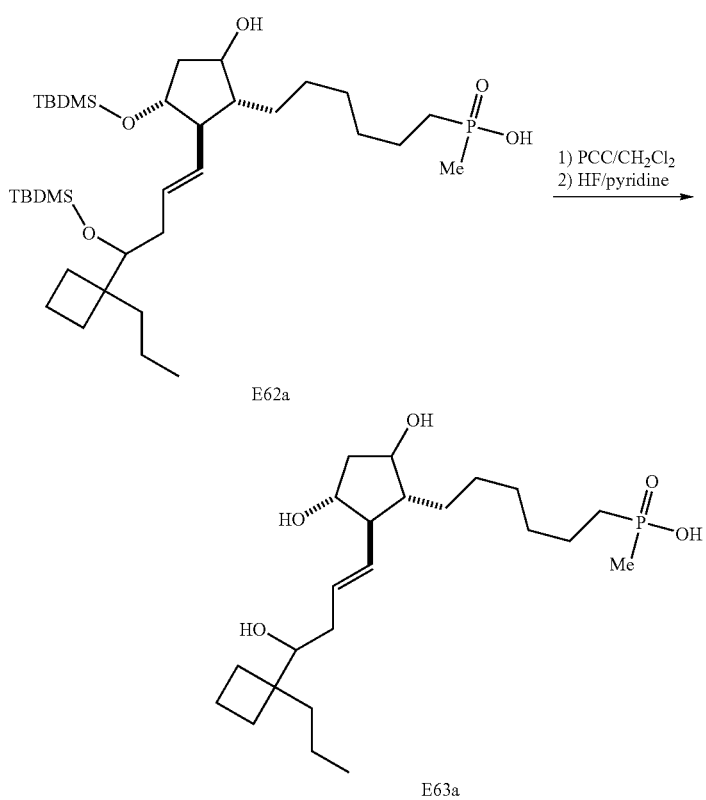

e. 5-(3-hydroxy-5-(2-fluorophenyl)pent-1-enyl)-4-(6-(methyl(hydroxyphosphoryl))hex-2-enyl)cyclopentane-1,3-diol, sodium salt (E1f): The compound E62a is dissolved in methylene chloride and PCC is added. The reaction is monitored by TLC and when the starting material is consumed, the reaction is poured through a plug of silica and Fluorosil, then concentrated. Without further purification to the crude reaction mixture of the 2-decarboxy-2-(O-ethyl-P-methylphosphinico)prostaglandin derivative acetonitrile and 1.1 equivalents of HF/Pyridine are added while the flask is kept at 0° C. After 3 hours at 0° C., the reaction is quenched with saturated aqueous NaCl. The aqueous layer is extracted three times with CH$_2$Cl$_2$. The organic layers are combined and washed three times with 1N HCl, brine, and dried over sodium sulfate. After column chromatography, (7:3, Hexane: ethyl acetate) the silyl-free product is obtained (E63a).

Examples 64–75

Using largely the procedure set forth in Examples 61 to 63 and substituting the appropriate starting materials the compounds 64–75 are made.

-continued
| Example | Structure |
|---|---|
| 64 | 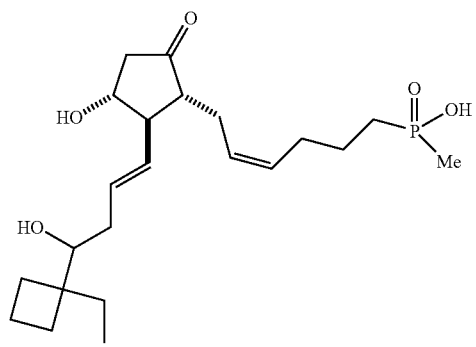 |
| 65 | 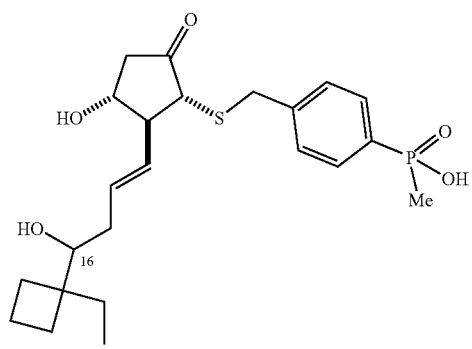 |
| 66 | 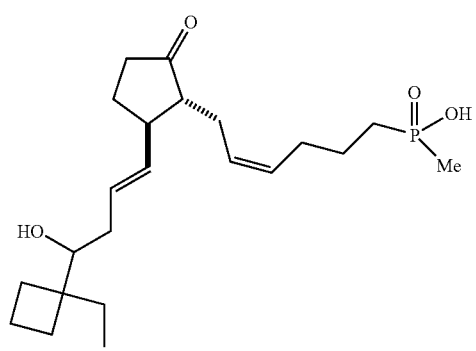 |
| 67 | 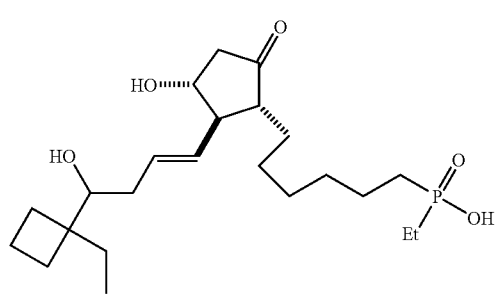 |
| 68 | 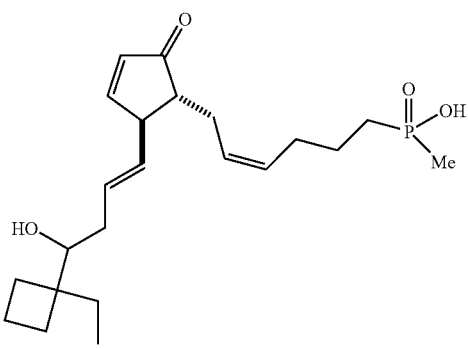 |
| 69 | 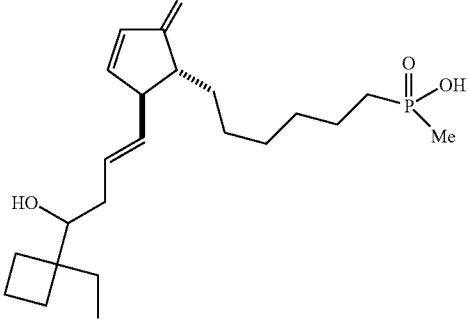 |
| 70 | 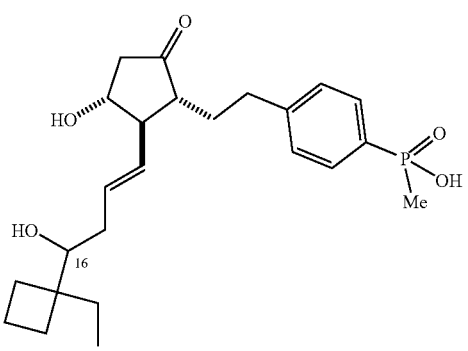 |
| 71 | 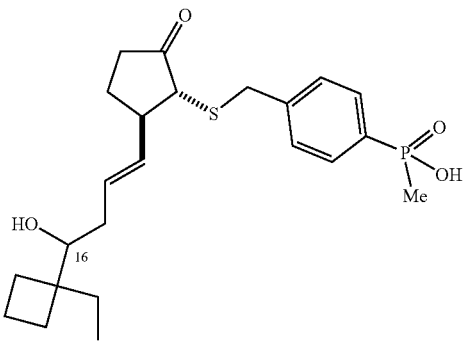 |

| Example | Structure |
|---|---|
| 72 | 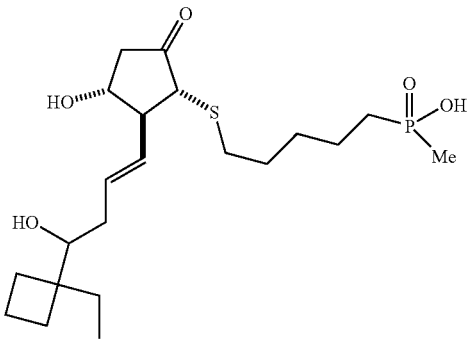 |
| 73 | 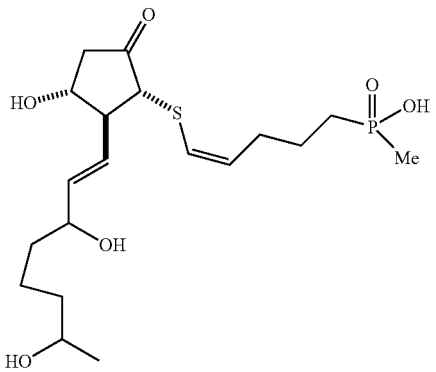 |
| 74 | 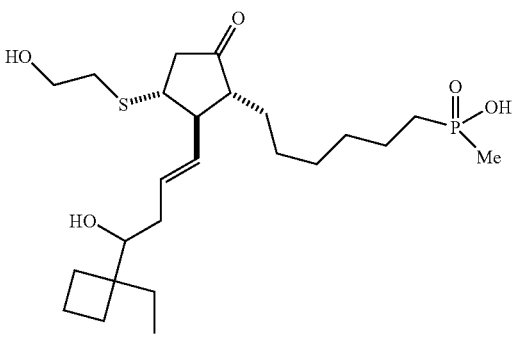 |
| 75 | 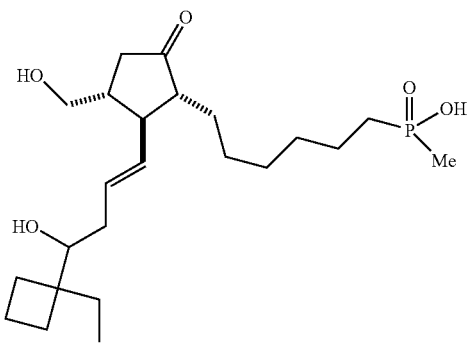 |

Examples 61–75 show that $EP_2$-specific agonists can be prepared according to this invention. They are made in analogy to Examples 1 and 2 above, or when available, they can be made directly from the commercially-available prostaglandins or intermediates, such as in Example 61.

Example 76

Preparation of 2-decarboxy-2-bromo-17-(3-methoxymethylphenyl)-17-trinor-$PGF_{2\alpha}$11,15-bis tert-butyldimethylsilylate, 9-acetate (E76b)

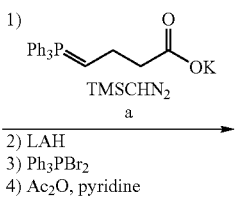

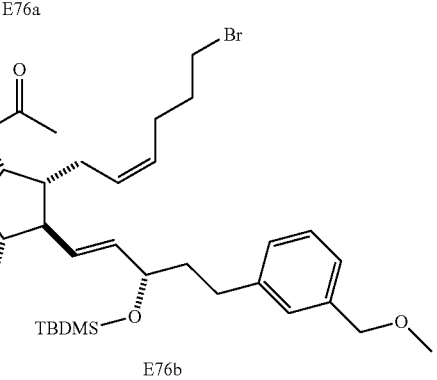

In a round bottom flask under argon the Wittig salt (a) (2.2 equiv.) is added to THF, and cooled to –78° C. Sodium hexamethyldisilazide (4.4 equiv.) is then added in one portion and the reaction is stirred for 15 minutes at –78° C. The solution is then warmed to 0° C. for two hours. The reaction mixture is then cooled again to –78° C. and the lactol E76a in THF is added over 10 minutes. E76a is prepared from Corey Aldehyde in a manner analogous to that taught in U.S. Pat. No. 6,048,895. The solution is stirred at –78° C. for 1 hour and then allowed to warm to room temperature and stirred an additional 17 hours. The reaction mixture is quenched with water and the THF is removed under reduced pressure. The residue is brought up in EtOAc/hexane and washed twice with 1N HCl. The organic layer is dried with ($Na_2SO_4$) and solvent is removed under reduced pressure. The residue is taken up in MeOH and TMS diazomethane (5 equiv.) is added slowly to the mixture. The solvent is concentrated and the residue is chromatographed on $SiO_2$ (10% EtOAc/hexanes) to provide the ester as a yellow oil.

To a solution of the ester (1 equiv.) in THF at –78° C. is added Lithium Aluminum Hydride (LAH) (1.3 equiv.) in one portion. The reaction mixture is stirred for 1 hour at –78° C. and then quenched with water. The solution is poured into $CH_2Cl_2$ and the aqueous layer is acidified to pH=1. The aqueous layer is re-extracted with $CH_2Cl_2$ and organics are combined. The organic layer is dried ($Na_2SO_4$) and concentrated. The residue is chromatographed on $SiO_2$ (10% EtOAc/hexanes) to provide the alcohol as a colorless oil. To a solution of that alcohol and pyridine (1.6 equiv.) in acetonitrile is added, at 0° C., over 10 min solid dibromotriphenylphosphine (1.4 equiv.). The reaction is monitored by TLC (4% EtOAc/hexanes) until complete. The solution is added to 5% EtOAc/hexanes and then the mixture is chromatographed on SiO$_2$ (5% EtOAc/hexanes) to provide the primary bromide as a colorless oil. This product is dissolved in pyridine and acetic anhydride (1.9 equiv.) and DMAP (0.05 equiv.). The reaction is stirred at 25° C. overnight. The reaction is then quenched with water. The organic layer is washed with brine, dried over MgSO$_4$, and concentrated in vacuo to give a crude product which is purified by flash chromatography on silica gel (hexanes then 1% MeOH in CH$_2$Cl$_2$) to 2-decarboxy-2-bromo-17-(3-methoxymethylphenyl)-17-trinor-PGF$_{2\alpha}$11,15-bis tert-butyldimethylsilylate, 9-acetate (E76b).

Example 77

Preparation of 2-decarboxy-2-(P-methylphosphinico)-17-(3-methoxymethylphenyl)-17-trinor-PGE$_1$ (E77c)

evaporated to give 2-decarboxy-2-(O-ethyl-P-methylphosphinico)-17-(3-methoxy methylphenyl)-17-trinor-PGF$_{2\alpha}$11,15-bis tert-butyldimethylsilylate, 9-acetate (E77a).

b. 2-decarboxy-2-(P-methylphosphinico)-17-(3-methoxymethylphenyl)-17-trinor-PGF$_{1\alpha}$11,15-bis tert-butyldimethylsilylate (E77b): The compound E77a is added to a flask in ethyl acetate and Pd/C 5% is added. This is stirred under an atmosphere of H$_2$ gas until gas uptake ceases, then filtered and the solvent removed in vacuuo. The residue is added to a 2.5M aqueous sodium hydroxide and is stirred at reflux for 3 hours. The mixture is then diluted with water and is washed two times with ethyl acetate. The combined washes are extracted with water. The combined aqueous phases are acidified with 1M aqueous hydrochloric acid and extracted four times with ethyl acetate. The combined extracts are dried (brine, Na$_2$SO$_4$) then dissolved in methylene chloride and pyridinium chlorochromate is added to effect oxidation

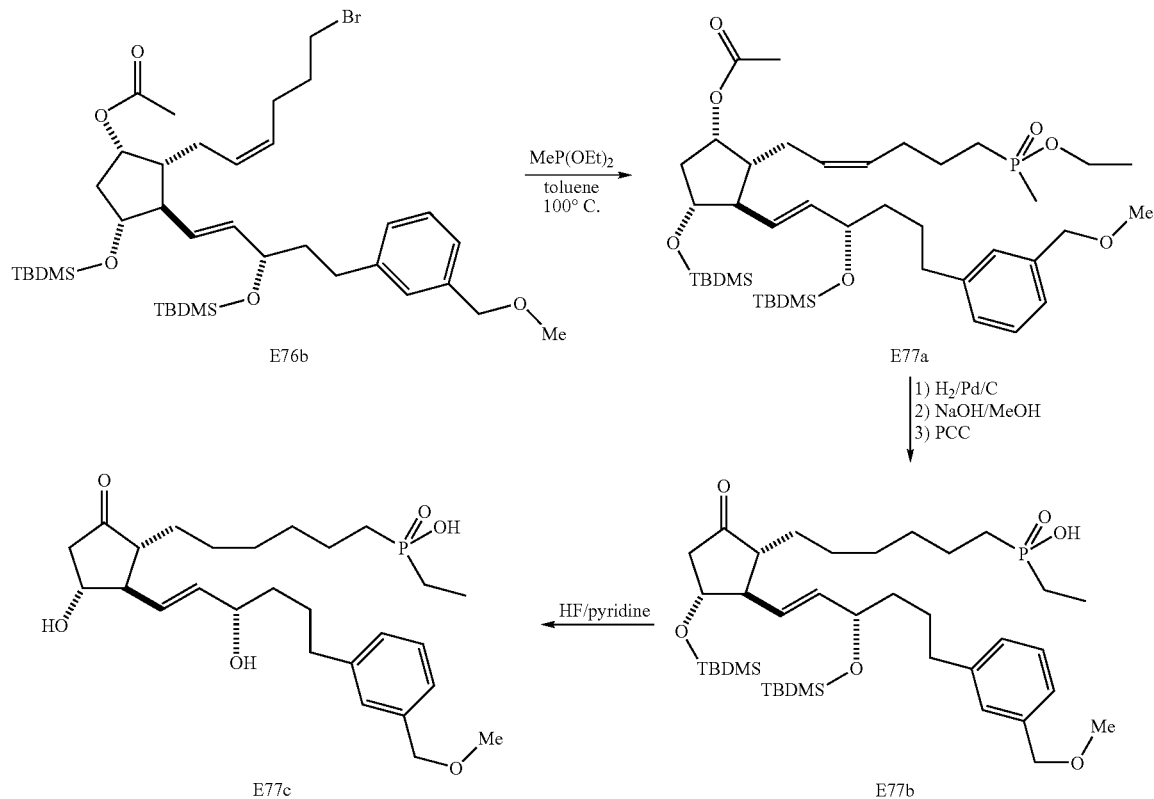

a. 2-decarboxy-2-(O-ethyl-P-methylphosphinico)-17-(3-methoxy-methylphenyl)-17-trinor-PGF$_{2\alpha}$11,15-bis tert-butyldimethylsilylate, 9-acetate (E77a): A mixture of 2-decarboxy-2-bromo-17-(3-methoxymethylphenyl)-17-trinor-PGF$_{2\alpha}$11,15-bis tert-butyldimethylsilylate, 9-acetate, diethyl methylphosphonite (E76b) and toluene is stirred at 100° C. for 8 hours. The toluene is evaporated and the residue is purified by SiO$_2$ column chromatography (5–25% 2-propanol in 20% dichloromethane-hexane). Appropriate fractions are concentrated, diluted with water, and extracted three times with ethyl acetate. The combined extracts are washed with water, are dried (brine, Na$_2$SO$_4$), and are of C-9 to the ketone. After three hours, the solution is filtered through silica, and the solvent is evaporated to give 2-decarboxy-2-(P-methylphosphinico)-17-(3-methoxymethylphenyl)-17-trinor-PGE$_1$11,15-bis tert-butyldimethylsilylate (E77b).

c. 2-decarboxy-2-(P-methylphosphinico)-17-(3-methoxymethylphenyl)-17-trinor-PGE$_1$ (E77c): The product E77b is dissolved in acetonitrile and HF/pyridine is added at zero degrees centigrade. The reaction is allowed to warm to room temperature, then the crude is concentrated by rotary evaporation, and the residue is chromatographed to yield 2-decarboxy-2-(P-methylphosphinico)-17-(3-methoxymethylphenyl)-17-trinor-PGE$_1$ (E77c).

Using largely the procedure set forth in Examples 76 and 77 and substituting the starting materials the compounds 78–85 are made.

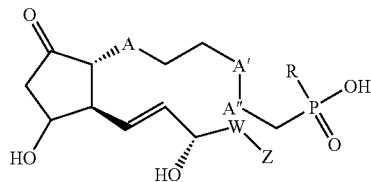

| Example | R  | A   | A'  | A"  | W      | Z |
|---------|----|-----|-----|-----|--------|---|
| 78 | Me | CH$_2$ | S | CH$_2$ | CH$_2$ | 3-(methoxymethyl)phenyl |
| 79 | Et | S | CH$_2$ | S | CH$_2$ | phenyl |
| 80 | Me | S | CH$_2$ | S | CH$_2$ | 3-(methoxymethyl)phenyl |
| 81 | Me | S | CH$_2$ | S | CH$_2$ | phenyl |
| 82 | Me | S | CH$_2$ | S | CH(CH$_3$) | n-butyl |
| 83 | Me | CH$_2$ | S | CH$_2$ | CH$_2$O | n-butyl |
| 84 | Et | CH$_2$ | S | CH$_2$ | CH$_2$ | 2-fluoro-5-(methoxymethyl)phenyl |
| 85 | Me | CH$_2$ | S | CH$_2$ | CH$_2$CH$_2$ | n-butyl |

Example 86

Preparation of [1α(Z),2β,5α]-7-{5-([1,1'-biphenyl]-4-yl methoxy)-2-(4-morpholinyl)-3-oxocyclopentyl]-4-heptenyl P-methyl phosphinic acid sodium salt (E86b)

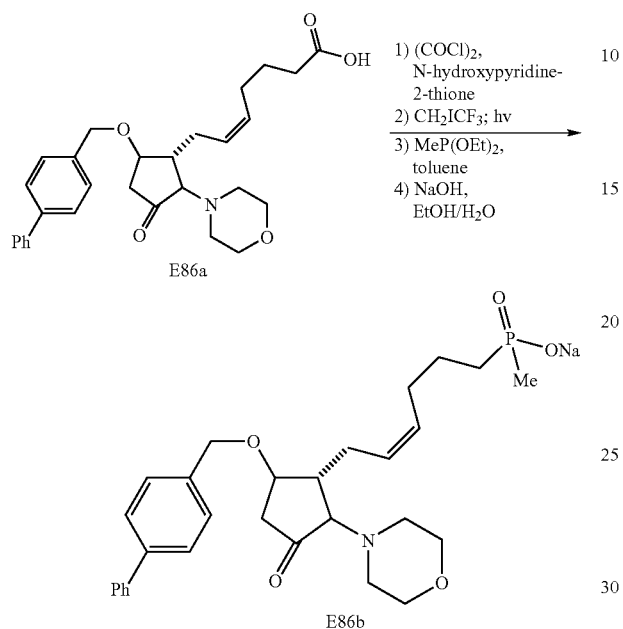

A mixture of [1α(Z),2β,5α]-7-{5-([1,1'-biphenyl]-4-yl methoxy)-2-(4-morpholinyl)-3-oxocyclopentyl]4-heptenoic acid (E86a) (available from Cayman Chemical Company), (or its reduced 3-alcohol), oxalyl chloride and dimethylformamide in dichloromethane is allowed to stand at room temperature for 30 minutes and is then concentrated. The residue is taken up in dichloromethane. Separately, a mixture of the sodium salt of N-hydroxypyridine-2-thione, DMAP, and dichloromethane under argon is brought to reflux by irradiation with a 250 Watt General Electric floodlamp. To this mixture is added 1,1,1-trifluoro-2-iodo-ethane, followed by the solution of acid chloride which is added over 15 minutes. Irradiation is continued for 45 minutes and then the mixture is concentrated and purified by dry-flash column chromatography to give the 1-nor-primary iodide A mixture of the iodide, diethyl methylphosphonite, and toluene is stirred at 100° C. for 7 hours. The solvents are evaporated and the residue is purified by $SiO_2$ column chromatography (5–25% 2-propanol in 20% dichloromethane-hexane). Appropriate fractions are concentrated, diluted with water and extracted with ethyl acetate three times. The combined extracts are washed with water, dried (brine, $Na_2SO_4$), and evaporated to yield the phosphinic acid ester.

A mixture of the phosphinic acid ester, 95% ethanol, and 2.5M aqueous sodium hydroxide is stirred at reflux for 3 hours. The mixture is diluted with water and is washed with ethyl acetate two times. The combined washes are extracted with water. The combined aqueous phases are acidified with 1M aqueous hydrochloric acid and extracted with ethyl acetate four times. The combined extracts are dried (brine, $Na_2SO_4$) and are evaporated. If the free alcohol is used it is oxidized with PCC to the ketone at this point. The residue is taken up in methanol and stirred with Amberlite CG-50 ($Na^+$ form) for 15 minutes. The resin is removed by filtration and the filtrate is concentrated to give [1α(Z),2β,5α]-7-{5-([1,1'-biphenyl]-4-yl methoxy)-2-(4-morpholinyl)-3-oxocyclopentyl]-4-heptenyl P-methyl phosphinic acid sodium salt, (E86b).

Example 87

Preparation of [1α(Z),2β,5α]-7-{5-([1,1'-biphenyl] 4-yl methoxy)-2-(4-morpholinyl)-3-oxocyclopentyl]-heptanyl P-ethyl phosphinic acid sodium salt, (E87)

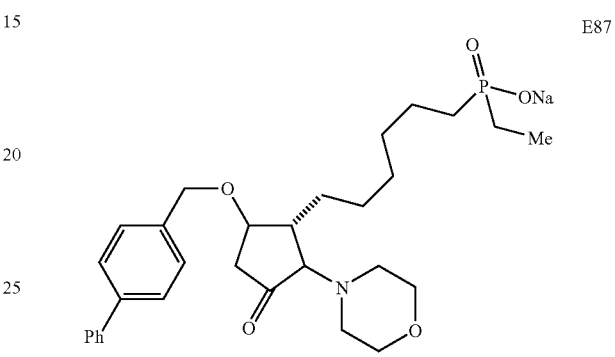

Examples 76–87 show that EP4 agonists can be synthesized according to this invention.

Example 88

Preparation of 1-(3-cyclohexyl-3-hydroxypropyl)-5-(6-(methyl(hydroxy-phosphoryl))hexyl)imiddazolidine-2,4-dione (E88b)

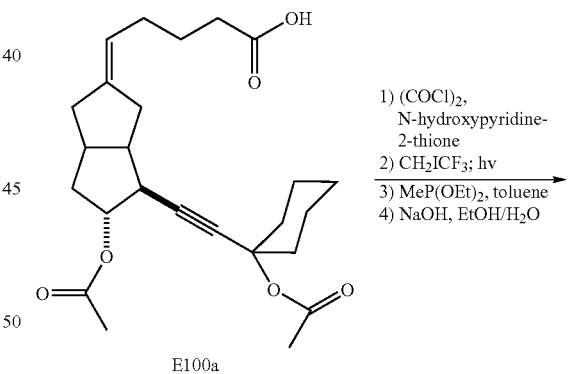

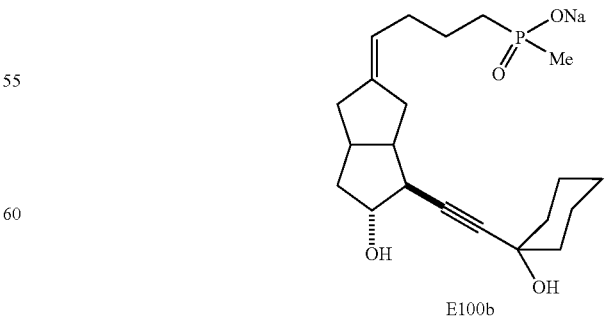

A mixture of (4S)-(3-[3R,S)-3-cyclohexyl-3-hydroxypropyl]-2,5-dioxo)-4-imidazolidineheptanoic acid (E88A)

67

(available from Cayman Chemical Company), oxalyl chloride and dimethylformamide in dichloromethane is allowed to stand at room temperature for 30 minutes and is then concentrated. The residue is taken up in dichloromethane. Separately, a mixture of the sodium salt of N-hydroxypyridine-2-thione, DMAP, and dichloromethane under argon is brought to reflux by irradiation with a 250 Watt General Electric floodlamp. To this mixture is added 1,1,1-trifluoro-2-iodoethane, followed by the solution of acid chloride which is added over 15 minutes. Irradiation is continued for 45 minutes and then the mixture is concentrated and purified by dry-flash column chromatography to give the 1-nor-primary iodide A mixture of the iodide, diethyl methylphosphonite, and toluene is stirred at 100° C. for 7 hours. The solvents are evaporated and the residue is purified by $SiO_2$ column chromatography (5–25% 2-propanol in 20% dichloromethane-hexane). Appropriate fractions are concentrated, diluted with water and extracted with ethyl acetate three times. The combined extracts are washed with water, dried (brine, $Na_2SO_4$), and evaporated to yield the phosphinic acid ester.

A mixture of the phosphinic acid ester, 95% ethanol, and 2.5M aqueous sodium hydroxide is stirred at reflux for 3 hours. The mixture is diluted with water and is washed with ethyl acetate two times. The combined washes are extracted with water. The combined aqueous phases are acidified with 1M aqueous hydrochloric acid and extracted with ethyl acetate four times. The combined extracts are dried (brine, $Na_2SO_4$) and are evaporated. The residue is taken up in methanol and stirred with Amberlite CG-50 ($Na^+$ form) for 15 minutes. The resin is removed by filtration and the filtrate is concentrated to give 1-(3-cyclohexyl-3-hydroxypropyl)-5-(6-(methyl(hydroxy-phosphoryl))hexyl)imiddazolidine-2,4-dione sodium salt, (E88b).

Examples 89–90

Examples 89–90 are prepared using substantially the same procedure as that described in Example 88, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 89

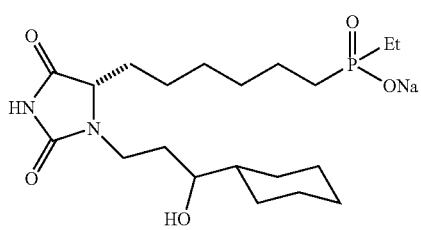

E89

68

Example 90

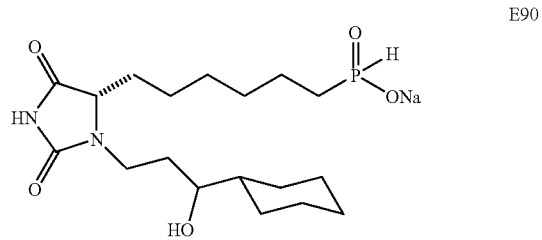

E90

Example 91

Preparation of 7-[3β-[(1,1'-biphenyl]-4-sulfonyl)amino]1α,4α-bicyclo[2.2.1]hept-2α-yl-5Z-heptenyl-P-methyl-phosphinic acid (E91b) sodium salt

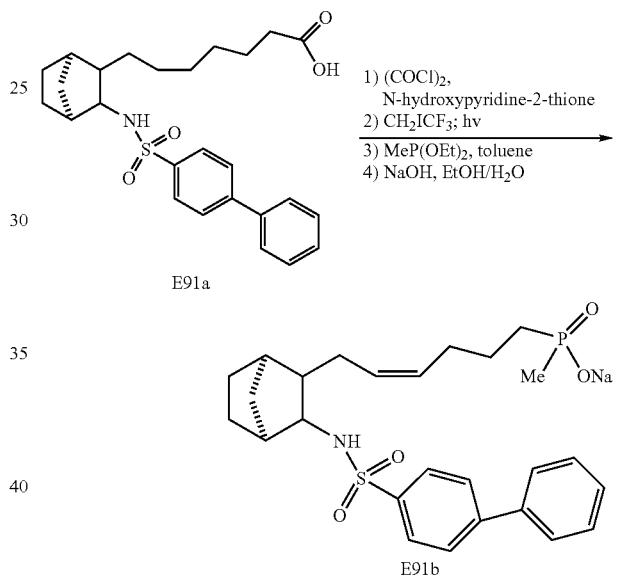

A mixture of 7-[3β-[(1,1'-biphenyl]-4-sulfonyl)amino]1α,4α-bicyclo[2.2.1]hept-2α-yl-5Z-heptenoic acid, (E91a) (available from Cayman Chemical Company) oxalyl chloride and dimethylformamide in dichloromethane is allowed to stand at room temperature for 30 minutes and is then concentrated. The residue is taken up in dichloromethane. Separately, a mixture of the sodium salt of N-hydroxypyridine-2-thione, DMAP, and dichloromethane under argon is brought to reflux by irradiation with a 250 Watt General Electric floodlamp. To this mixture is added 1,1,1-trifluoro-2-iodoethane, followed by the solution of acid chloride which is added over 15 minutes. Irradiation is continued for 45 minutes and then the mixture is concentrated and purified by dry-flash column chromatography to give the 1-nor-primary iodide A mixture of that iodide, diethyl methylphosphonite, and toluene is stirred at 100° C. for 7 hours. The solvents are evaporated and the residue is purified by $SiO_2$ column chromatography (5–25% 2-propanol in 20% dichloromethane-hexane). Appropriate fractions are concentrated, diluted with water and extracted with ethyl acetate three times. The combined extracts are washed with water, dried (brine, Na$_2$SO$_4$), and evaporated to yield the phosphinic acid ester.

A mixture of the phosphinic acid ester, 95% ethanol, and 2.5M aqueous sodium hydroxide is stirred at reflux for 3 hours. The mixture is diluted with water and is washed with ethyl acetate two times. The combined washes are extracted with water. The combined aqueous phases are acidified with 1M aqueous hydrochloric acid and extracted with ethyl acetate four times. The combined extracts are dried (brine, Na$_2$SO$_4$) and are evaporated. The residue is taken up in methanol and stirred with Amberlite CG-50 (Na$^+$ form) for 15 minutes. The resin is removed by filtration and the filtrate is concentrated to give 7-[3β-[(1,1'-biphenyl]-4-sulfonyl)amino]1α,4α-bicyclo[2.2.1]hept-2α-yl-5Z-heptenyl-P-methyl-phosphinic acid sodium salt, (E91b).

Examples 92–94

Examples 92–94 are prepared using substantially the same procedure as that described in Example 91, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 92–94

| Example | Structure |
|---|---|
| 92 | 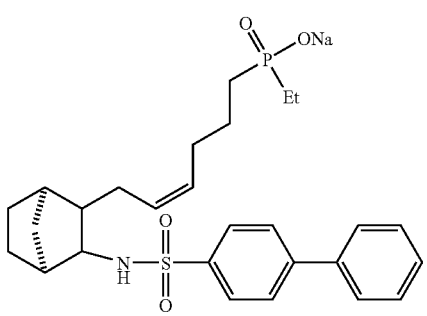 |
| 93 | 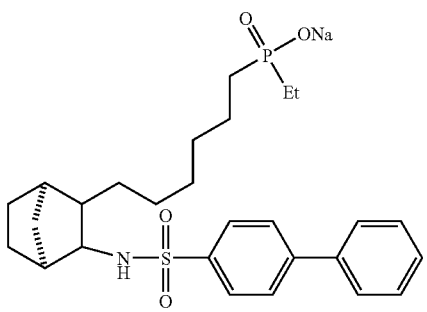 |
| 94 | 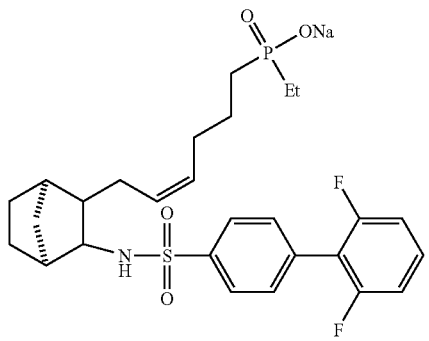 |

—continued

Example 95

Preparation of 3-(3-hydroxyoctyl)-2-(6-(methyl(hydroxyphosphoryl))hexyl)-1,3-thiazolidin-4-one (E95B) sodium salt

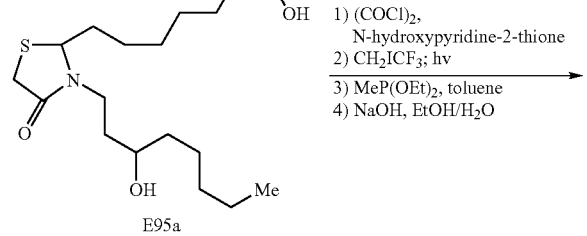

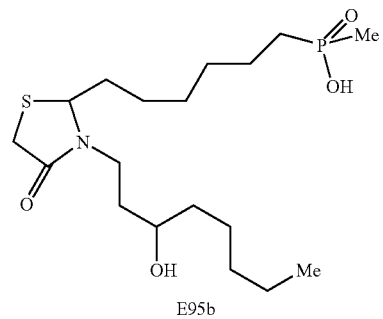

A mixture of 3-(3-hydroxyoctyl)-2-(carboxyheptyl)-1,3-thiazolidin-4-one (E95a), oxalyl chloride and dimethylformamide in dichloromethane is allowed to stand at room temperature for 30 minutes and is then concentrated. The residue is taken up in dichloromethane. Separately, a mixture of the sodium salt of N-hydroxypyridine-2-thione, DMAP, and dichloromethane under argon is brought to reflux by irradiation with a 250 Watt General Electric floodlamp. To this mixture is added 1,1,1-trifluoro-2-iodo-ethane, followed by the solution of acid chloride which is added over 15 minutes. Irradiation is continued for 45 minutes and then the mixture is concentrated and purified by dry-flash column chromatography to give the 1-nor-primary iodide A mixture of the iodide, diethyl methylphosphonite, and toluene is stirred at 100° C. for 7 hours. The solvents are evaporated and the residue is purified by SiO$_2$ column chromatography (5–25% 2-propanol in 20% dichloromethane-hexane). Appropriate fractions are concentrated, diluted with water and extracted with ethyl acetate three times. The combined extracts are washed with water, dried (brine, Na$_2$SO$_4$), and evaporated to yield the phosphinic acid ester.

A mixture of the phosphinic acid ester, 95% ethanol, and 2.5M aqueous sodium hydroxide is stirred at reflux for 3 hours. The mixture is diluted with water and is washed with ethyl acetate two times. The combined washes are extracted with water. The combined aqueous phases are acidified with 1M aqueous hydrochloric acid and extracted with ethyl acetate four times. The combined extracts are dried (brine, Na$_2$SO$_4$) and are evaporated. The residue is taken up in methanol and stirred with Amberlite CG-50 (Na$^+$ form) for 15 minutes. The resin is removed by filtration and the filtrate is concentrated to 3-(3-hydroxyoctyl)-2-(6-(methyl(hydroxy-phosphoryl))hexyl)-1,3-thiazolidin-4-one sodium salt (E95b).

Examples 96–99

Examples 96–99 are prepared using substantially the same procedure as that described in Example 95, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 96–99

| Example | Structure |
|---|---|
| 96 | 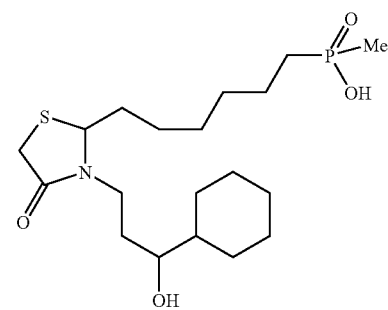 |
| 97 | 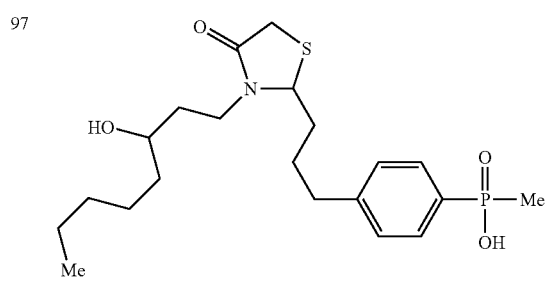 |
| 98 | 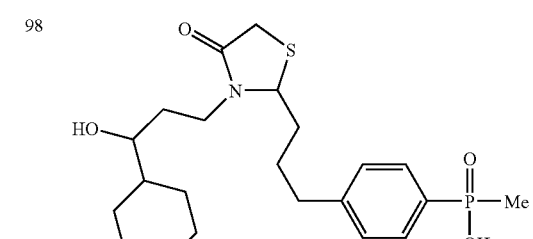 |
| 99 | 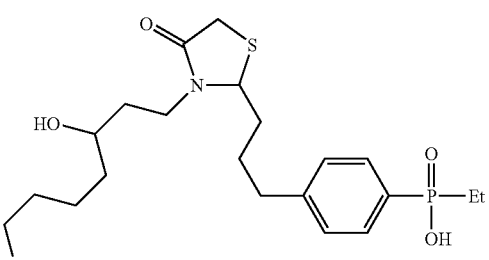 |

Examples 88–97 show that DP agonists can be prepared according to this invention. The DP agonists are made in analogy to Examples 1 and 2 above, or when available, they can be made directly from the commercially-available prostaglandins or intermediates, such as in Example 88.

Example 100

Preparation of 2-(2-(hydroxycyclohexyl)vinyl)-7-(4-(methyl(hydroxyphosphoryl))butylidene)bicyclo[3.3.0]octan-3-ol (E100b)

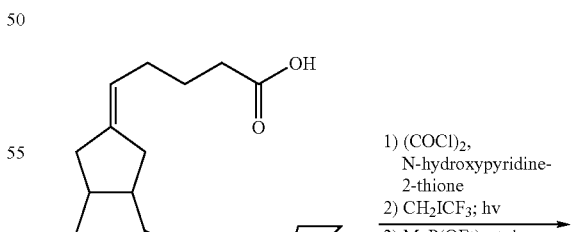

1) (COCl)$_2$, N-hydroxypyridine-2-thione
2) CH$_2$ICF$_3$; hv
3) MeP(OEt)$_2$, toluene
4) NaOH, EtOH/H$_2$O E100a -continued

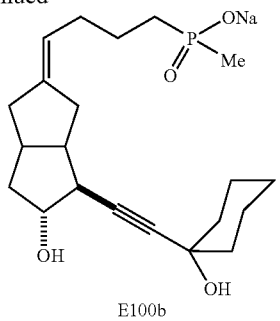

E100b

A mixture of 9,15-diacetyl, 13,14 dehydro-15-cyclohexyl carbaprostacyclin (E100a) (prepared from 13,14 dehydro-15-cyclohexyl carbaprostacyclin, which is available from Cayman Chemical Company), oxalyl chloride and dimethylformamide in dichloromethane is allowed to stand at room temperature for 30 minutes and is then concentrated. The residue is taken up in dichloromethane. Separately, a mixture of the sodium salt of N-hydroxypyridine-2-thione, DMAP, and dichloromethane under argon is brought to reflux by irradiation with a 250 Watt General Electric floodlamp. To this mixture is added 1,1,1-trifluoro-2-iodo-ethane, followed by the solution of acid chloride which is added over 15 minutes. Irradiation is continued for 45 minutes and then the mixture is concentrated and purified by dry-flash column chromatography to give the 1-nor-primary iodide A mixture of the iodide, diethyl methylphosphonite, and toluene is stirred at 100° C. for 7 hours. The solvents are evaporated and the residue is purified by $SiO_2$ column chromatography (5–25% 2-propanol in 20% dichloromethane-hexane). Appropriate fractions are concentrated, diluted with water and extracted with ethyl acetate three times. The combined extracts are washed with water, dried (brine, $Na_2SO_4$), and evaporated to yield the phosphinic acid ester.

A mixture of the phosphinic acid ester, 95% ethanol, and 2.5M aqueous sodium hydroxide is stirred at reflux for 3 hours. The mixture is diluted with water and is washed with ethyl acetate two times. The combined washes are extracted with water. The combined aqueous phases are acidified with 1M aqueous hydrochloric acid and extracted with ethyl acetate four times. The combined extracts are dried (brine, $Na_2SO_4$) and are evaporated. The residue is taken up in methanol and stirred with Amberlite CG-50 ($Na^+$ form) for 15 minutes. The resin is removed by filtration and the filtrate is concentrated to give 2-(2-(hydroxycyclohexyl)vinyl)-7-(4-(methyl(hydroxyphosphoryl))butylidene)bicyclo[3.3.0]octan-3-ol sodium salt, (E100b).

Example 101–107

Examples 101–107 are prepared using substantially the same procedure as that described in Example 100, substituting the appropriate starting materials, such as ones available from the Cayman Chemical company. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Examples 100–107

| Example | Structure |
|---------|-----------|
| 101 | 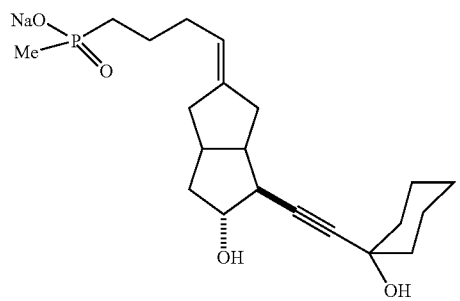 |
| 102 | 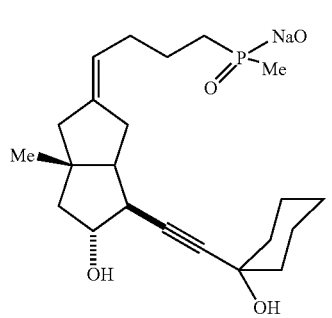 |
| 103 | 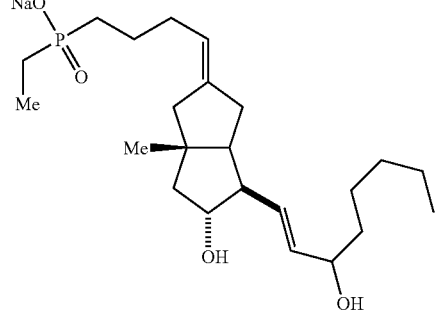 |
| 104 | 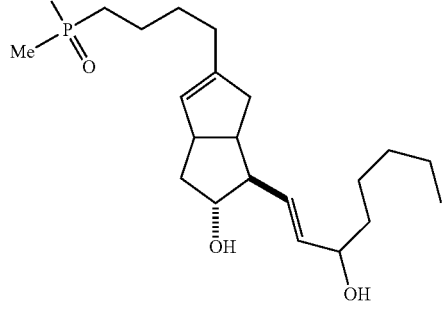 |

-continued

| Example | Structure |
|---------|-----------|
| 105 | 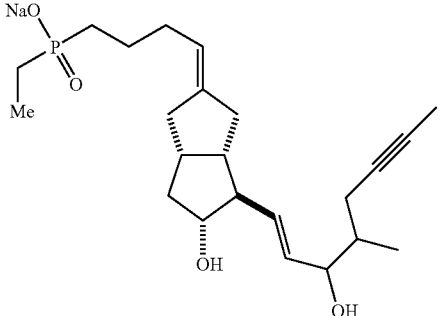 |
| 106 | 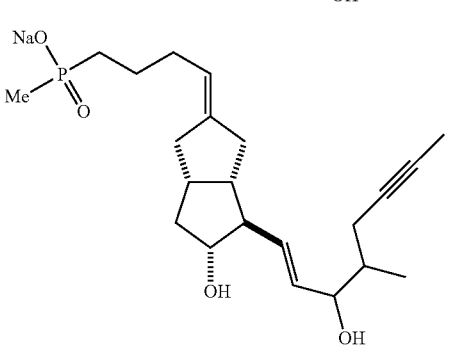 |
| 107 | 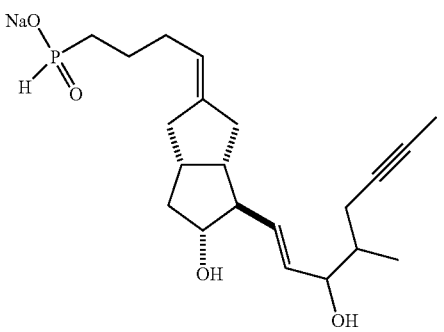 |

Examples 100–107 are of the syntheses of IP-specific agonists. They are made in analogy to Examples 1 and 2 above, or when available, they can be made directly from the commercially-available prostaglandins or intermediates, such as in Example 100.

Reference Example 1

Radioligand Binding Assay $IC_{50}$ of a prostaglandin derivative can be determined relative to a naturally occurring prostaglandin using the Radioligand Binding Assay. As a control, the $IC_{50}$ for the naturallly occurring prostaglandin itself should be no lower than 1.0 nM and no higher than 50 nM.

In a typical assay, COS-7 cells are transiently transfected with the hFP recombinant plasmid using LipofectAMINE Reagent. Forty-eight hours later, the tranfected cells are washed with Hank's Balanced Salt Solution (HBSS, without $CaCl_2$, $MgCl_2$, $MgSO_4$, or phenol red). The cells are detached with versene, and HBSS is added. The mixture is centrifuged at 200 g for 10 minutes, at 4° C. to pellet the cells. The pellet is resuspended in Phosphate-Buffered Saline-EDTA buffer (PBS; 1 mM EDTA; pH 7.4; 4° C.). The cells are disrupted by nitrogen cavitation (Parr model 4639), at 800 psi, for 15 minutes at 4° C. The mixture is centrifuged at 1000 g for 10 minutes at 4° C. The supernatant is centrifuged at 100,000 g for 60 minutes at 4° C. The pellet is resuspended to 1 mg protein/mL TME buffer (50 mM Tris; 10 mM MgCl2; 1 mM EDTA; pH 6.0; 4° C.) based on protein levels measured using the Pierce BCA Protein Assay kit. The homogenate is mixed for 10 seconds using a Kinematica POLYTRON® (available from KINEMATICA AG, Luzernerstrasse147A CH-6014 Littau, Switzerland. The membrane preparations are then stored at −80° C., until thawed for assay use.

The receptor competition binding assays are developed in a 96 well format. Each well contains 100 g of hFP membrane, 5 nM (3H) $PGF2\alpha$, and the various competing compounds in a total volume of 200 L. The plates are incubated at 23° C. for 1 hour. The incubation is terminated by rapid filtration using the Packard Filtermate 196 harvester through Packard UNIFILTER® GF/B filters (available from Packard Instrument Co., Inc. of Downers Grove Ill.) pre-wetted with TME buffer. The filter is washed four times with TME buffer. Packard Microscint 20, a high efficiency liquid scintillation cocktail, is added to the filter plate wells and the plates remain at room temperature for three hours prior to counting. The plates are read on a Packard TOPCOUNT® Microplate Scintillation Counter (also available from Packard Instrument Co., Inc.)

Reference Example 2

Ovariectomized Rat Assay (EP1, 2, 3, 4, Agonists)

Bone activity of the prostaglandins can be conveniently demonstrated using an assay designed to test the ability of the prostaglandins to increase bone volume, mass, or density. An example of such assays is the ovariectomized rat assay.

In the ovariectomized rat assay, six-month old rats are ovariectomized, aged 2 months, and then dosed once a day subcutaneously with a prostaglandin. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Example 108

Pharmaceutical compositions in the form of tablets are prepared by conventional methods, such as mixing and direct compaction, formulated as follows:

| Ingredient | Quantity (mg per tablet) |
|---|---|
| Prostaglandin Derivative | 5 |
| Microcrystalline Cellulose | 100 |
| Sodium Starch Glycollate | 30 |
| Magnesium Stearate | 3 |

An $EP_1$ agonist according to this invention is used as the prostaglandin derivative. When administered orally once daily, the above composition substantially increases bone volume in a patient suffering from osteoporosis.

Example 109

Example 108 is repeated using a $EP_2$ agonist according to this invention instead of the $EP_1$ agonist. When administered orally once daily, the above composition substantially increases bone volume in a patient suffering from osteoporosis.

Example 110

Pharmaceutical compositions in liquid form are prepared by conventional methods, formulated as follows:

| Ingredient | Quantity |
| --- | --- |
| Prostaglandin Derivative | 1 mg |
| Phosphate buffered physiological saline | 10 ml |
| Methyl Paraben | 0.05 ml |

An $EP_3$ agonist according to this invention is used as the prostaglandin derivative. When 1.0 ml of the above composition is administered subcutaneously once daily, the above composition substantially increases bone volume in a patient suffering from osteoporosis.

Example 111

Example 110 is repeated using a $EP_4$ agonist according to this invention instead of the $EP_3$ agonist. When administered orally once daily, the above composition substantially increases bone volume in a patient suffering from osteoporosis.

Reference Example 3

Pharmacological Activity for Glaucoma Assay

Pharmacological activity for glaucoma can be demonstrated using assays designed to test the ability of the subject compounds to decrease intraocular pressure. Examples of such assays are described in the following reference, incorporated herein: C. Iiljebris, G. Selen, B. Resul, J. Sternschantz, and U. Hacksell, "Derivatives of 17-Phenyl-18,19, 20-trinorprostaglandin $F_2\alpha$ Isopropyl Ester: Potential Antiglaucoma Agents", *Journal of Medicinal Chemistry*, Vol. 38 No. 2 (1995), pp. 289–304.

Example 112

Topical pharmaceutical compositions for lowering intraocular pressure are prepared by conventional methods and formulated as follows:

| Ingredient | Amount (wt %) |
| --- | --- |
| Prostaglandin Derivative | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCl and/or NaOH | pH 7.2–7.5 |
| Purified water | q.s. to 100% |

An $EP_2$ antagonist according to this invention is used as the prostaglandin derivative. When the composition is topically administered to the eyes once daily, the above composition decreases intraocular pressure in a patient suffering from glaucoma.

Example 113

Example 112 is repeated using an $EP_4$ antagonist according to this invention instead of the $EP_2$ antagonist. When administered orally once daily, the above composition substantially increases bone volume in a patient suffering from osteoporosis.

Reference Example 4

Telogen Conversion Assay

Prostaglandins are tested for their potential to grow hair using the Telogen Conversion Assay. The Telogen Conversion Assay measures the potential of a prostaglandin to convert mice in the resting stage of the hair growth cycle ("telogen"), to the growth stage of the hair growth cycle ("anagen").

Without intending to be limited by theory, there are three principal phases of the hair growth cycle: anagen, catagen, and telogen. It is believed that there is a longer telogen period in C3H mice (Harlan Sprague Dawley, Inc., Indianapolis, Ind.) from approximately 40 days of age until about 75 days of age, when hair growth is synchronized. It is believed that after 75 days of age, hair growth is no longer synchronized. Wherein about 40 day-old mice with dark fur (brown or black) are used in hair growth experiments, melanogenesis occurs along with hair (fur) growth wherein the topical application of hair growth inducers are evaluated. The Telogen Conversion Assay herein is used to screen prostaglandins for potential hair growth by measuring melanogenesis.

Three groups of 44 day-old C3H mice are used: a vehicle control group, a positive control group, and a test prostaglandin group, wherein the test prostaglandin group is administered a prostaglandin used in the method of this invention. The length of the assay is 24 days with 15 treatment days (wherein the treatment days occur Mondays through Fridays). Day 1 is the first day of treatment. A typical study design is shown in Table 4 below. Typical dosage concentrations are set forth in Table RE1, however the skilled artisan will readily understand that such concentrations may be modified.

TABLE RE1

| | | Assay Parameters | | | |
| --- | --- | --- | --- | --- | --- |
| Group # | Animal # | Compound | Concentration | Application volume | Length of Study |
| 1 | 1–10 | Test Compound | 0.01% in vehicle** | 400 µL topical | 26 days |
| 2 | 11–20 | Positive Control (T3)* | 0.01% in vehicle** | 400 µL topical | 26 days |
| 3 | 21–30 | Vehicle** | N/A | 400 µL topical | 26 days |

*T3 is 3,5,3'-triiodothyronine.
**The vehicle is 60% ethanol, 20% propylene glycol, and 20% dimethyl isosorbide (commercially available from Sigma Chemical Co., St. Louis, MO).

The mice are treated topically Monday through Friday on their lower back (base of tail to the lower rib). A pipettor and tip are used to deliver 400 µL to each mouse's back. The 400 µL application is applied slowly while moving hair on the mouse to allow the application to reach the skin.

While each treatment is being applied to the mouse topically, a visual grade of from 0 to 4 will be given to the skin color in the application area of each animal. As a mouse converts from telogen to anagen, its skin color will become more bluish-black. As indicated in Table RE2, the grades 0 to 4 represent the following visual observations as the skin progresses from white to bluish-black.

TABLE RE2

Evaluation Criteria

| Visual Observation | Grade |
| --- | --- |
| Whitish Skin Color | 0 |
| Skin is light gray (indication of initiation of anagen) | 1 |
| Appearance of Blue Spots | 2 |
| Blue Spots are aggregating to form one large blue area | 3 |
| Skin is dark blue (almost black) with color covering majority of treatment area (indication of mouse in full anagen) | 4 |

Example 114

Compositions for topical administration are made, comprising:

| Component | 114-1 | 114-2 | 114-3 | 114-4 |
| --- | --- | --- | --- | --- |
| PGF agonist (wt %) | 0.01 | 0.1 | 1.0 | 10.0 |
| $IC_{50}$ the PGF (nM) | 1 | 10 | 100 | 1000 |
| Ethanol (wt %) | 59.99 | 59.9 | 59.4 | 54.0 |
| Propylene Glycol (wt %) | 20.00 | 20.0 | 19.8 | 18.0 |
| Dimethyl Isosorbide (wt %) | 20.00 | 20.0 | 19.8 | 18.0 |

A human male subject suffering from male pattern baldness is treated by a method of this invention. Specifically, for 6 weeks, one of the above compositions is daily administered topically to the subject.

Example 115

A composition for topical administration is made according to the method of Dowton et al., "Influence of Liposomal Composition on Topical Delivery of Encapsulated Cyclosporin A: I. An in vitro Study Using Hairless Mouse Skin", *S.T.P. Pharma Sciences*, Vol. 3, pp. 404–407 (1993), using a PGF agonist according to this invention in lieu of cyclosporin A and using the NOVASOME® 1 (available from Micro-Pak, Inc. of Wilmington, Del.) for the non-ionic liposomal formulation.

A human male subject suffering from male pattern baldness is treated each day with the above composition. Specifically, for 6 weeks, the above composition is administered topically to the subject.

Example 116

Shampoos are made, comprising:

| Component | Ex. 116-1 | Ex. 116-2 | Ex. 116-3 | Ex. 116-4 |
| --- | --- | --- | --- | --- |
| Ammonium Lauryl Sulfate | 11.5% | 11.5% | 9.5% | 7.5% |
| Ammonium Laureth Sulfate | 4% | 3% | 2% | 2% |
| Cocamide MEA | 2% | 2% | 2% | 2% |
| Ethylene Glycol Distearate | 2% | 2% | 2% | 2% |
| Cetyl Alcohol | 2% | 2% | 2% | 2% |
| Stearyl Alcohol | 1.2% | 1.2% | 1.2% | 1.2% |
| Glycerin | 1% | 1% | 1% | 1% |
| Polyquaternium 10 | 0.5% | 0.25% | — | — |
| Polyquaternium 24 | — | — | 0.5% | 0.25% |
| Sodium Chloride | 0.1% | 0.1% | 0.1% | 0.1% |
| Sucrose Polyesters of Cottonate Fatty Acid | 3% | 3% | — | — |
| Sucrose Polyesters of Behenate Fatty Acid | 2% | 3% | — | — |
| Polydimethyl Siloxane | — | — | 3% | 2% |
| Cocaminopropyl Betaine | — | 1% | 3% | 3% |
| Lauryl Dimethyl Amine Oxide | 1.5% | 1.5% | 1.5% | 1.5% |
| Decyl Polyglucose | — | — | 1% | 1% |
| DMDM Hydantoin | 0.15% | 0.15% | 0.15% | 0.15% |
| PGF agonist having $IC_{50}$ of 200 nM | — | 0.2% | 0.2% | — |
| PGF agonist having $IC_{50}$ of 100 nM | 0.1% | — | — | 0.1% |
| Minoxidil | — | — | 3% | 2% |
| Phenoxyethanol | 0.5% | 0.5% | 0.5% | 0.5% |
| Fragrance | 0.5% | 0.5% | 0.5% | 0.5% |
| Water | q.s. | q.s. | q.s. | q.s. |

A human subject suffering from male pattern baldness is treated by a method of this invention. Specifically, for 12 weeks, a shampoo described above is used daily by the subject.

Example 117

Pharmaceutical compositions in liquid form are prepared by conventional methods, formulated as follows:

| Ingredient | Quantity |
| --- | --- |
| Prostaglandin Derivative | 1 mg |
| Phosphate buffered physiological saline | 10 ml |
| Methyl Paraben | 0.05 ml |

An FP antagonist according to this invention is used as the prostaglandin derivative. When 0.25 mL/min of the above composition is instilled into a uterus undergoing premature labor, the above composition decreases uterine contractions within the first hour, preventing premature birth.

Example 118

Pharmaceutical compositions in the form of tablets are prepared by conventional methods, such as mixing and direct compaction, formulated as follows:

| Ingredient | Quantity (mg per tablet) |
| --- | --- |
| Prostaglandin Derivative | 5 |
| Microcrystalline Cellulose | 100 |
| Sodium Starch Glycollate | 30 |
| Magnesium Stearate | 3 |

An DP antagonist according to this invention is used as the prostaglandin derivative. When administered orally twice daily, the above composition substantially reduces allergic symptoms in a patient suffering from seasonal allergies.

Example 119

Pharmaceutical compositions in the form of tablets are prepared by conventional methods, such as mixing and direct compaction, formulated as follows:

| Ingredient | Quantity (mg per tablet) |
| --- | --- |
| Prostaglandin Derivative | 5 |
| Microcrystalline Cellulose | 100 |
| Sodium Starch Glycollate | 30 |
| Magnesium Stearate | 3 |

An EP1 antagonist according to this invention is used as the prostaglandin derivative. When administered orally four times daily, the above composition substantially reduces pain of headache, migraine pain or muscle pain in a patient.

Example 120

Pharmaceutical compositions in the form of tablets are prepared by conventional methods, such as mixing and direct compaction, formulated as follows:

| Ingredient | Quantity (mg per tablet) |
| --- | --- |
| Prostaglandin Derivative | 5 |
| Microcrystalline Cellulose | 100 |
| Sodium Starch Glycollate | 30 |
| Magnesium Stearate | 3 |

An TP antagonist according to this invention is used as the prostaglandin derivative. When administered orally four times daily, the above composition substantially reduces the severity of ulcerative colitis in a patient suffering from that disease.

Example 121

Pharmaceutical compositions in the form of tablets are prepared by conventional methods, such as mixing and direct compaction, formulated as follows:

| Ingredient | Quantity (mg per tablet) |
| --- | --- |
| Prostaglandin Derivative | 5 |
| Microcrystalline Cellulose | 100 |
| Sodium Starch Glycollate | 30 |
| Magnesium Stearate | 3 |

An IP agonist according to this invention is used as the prostaglandin derivative. When administered orally twice daily, the above composition substantially reduces blood pressure and improves peripheral circulation in patients suffering from high blood pressure and/or poor peripheral circulation.

What is claimed is:

1. A composition comprising:
   (A) a 2-decarboxy-2-phosphinico prostaglandin derivative having a structure selected from the group consisting of:

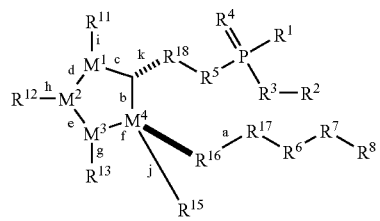

wherein bond a is selected from the group consisting of a single bond, a trans double bond, and a triple bond;

each of bonds b, c, d, e, and f are independently selected from the group consisting of a single bond and a double bond;

each of bonds g, h, i, and j are independently selected from the group consisting of nil, a single bond, and a double bond;

bond k is selected from the group consisting of a single bond and a double bond;

$R^1$ is selected from the group consisting of a hydrogen atom, a monovalent hydrocarbon group having 1 to 4 carbon atoms, and a monovalent heterogenous group having 1 to 4 member atoms;

$R^2$ is selected from the group consisting of a hydrogen atom, a monovalent hydrocarbon group, a substituted monovalent hydrocarbon group, a monovalent heterogeneous group, a substituted monovalent heterogeneous group, a carbocyclic group, a substituted carbocyclic group, a heterocyclic group, a substituted heterocyclic group, an aromatic group, a substituted aromatic group, a heteroaromatic group, and a substituted heteroaromatic group;

$R^3$ is selected from the group consisting of an oxygen atom, a sulfur atom, and NH;

$R^4$ is selected from the group consisting of an oxygen atom and a sulfur atom;

$R^5$ is a divalent group selected from the group consisting of a hydrocarbon group, a substituted hydrocarbon group, a heterogeneous group, and a substituted heterogeneous group;

$R^6$ is nil or a divalent group selected from the group consisting of —$CH_2$—, —C(O)— and —C($R^{10}$)(O$R^{10}$)—;

$R^7$ is nil or a divalent group having the formula —(CD(D))$_p$-X—(CD(D))$_q$-, wherein p is an integer from 0 to 3 and q is an integer from 0 to 3, X is selected from the group consisting of an oxygen atom, a divalent hydrocarbon group, a sulfur atom, SO, $SO_2$, and ND, and each D is independently selected from the group consisting of a hydrogen atom, a monovalent hydrocarbon group of 1 to 4 carbon atoms, and a monovalent heterogenous group of 1 to 4 member atoms;

$R^8$ is selected from the group consisting of a hydrocarbon group, a substituted hydrocarbon group, a heterogenous group, a substituted heterogenous group, a carbocyclic group, a substituted carbocyclic group, a heterocyclic group, a substituted heterocyclic group, an aromatic group, a substituted aromatic group, a heteroaromatic group, and a substituted heteroaromatic group;

$R^9$ is selected from the group consisting of a hydrogen atom, a monovalent hydrocarbon group of 1 to 4 carbon atoms, and a monovalent heterogenous group of 1 to 4 member atoms;

$R^{10}$ is selected from the group consisting of a hydrogen atom, a monovalent hydrocarbon group of 1 to 4 carbon atoms, and a monovalent heterogenous group of 1 to 4 member atoms;

$M^1$, $M^2$, $M^3$, and $M^4$ are each independently selected from the group consisting of a carbon atom and a heteroatom, with the proviso that no two heteroatoms may be adjacent;

$R^{11}$, $R^{12}$, $R^{13}$, and $R^{15}$ are each independently selected from the group consisting of nil, a halogen atom, a heteroatom, and $R^2$, with the provisos that optionally, $R^{11}$ and $R^{12}$, $R^{12}$ and $R^{13}$, or $R^{11}$ and $R^{13}$ may be bonded together to form a ring structure such as a carbocyclic group, a heterocyclic group, an aromatic group, a heteroaromatic group, a substituted carbocyclic group, a substituted heterocyclic group, a substituted aromatic group, or a substituted heteroaromatic group, when $R^{11}$ is $OR^9$, $R^{12}$ is a hydrogen atom, and $M^2$ is a carbon atom; $R^{13}$ is not a hydrogen atom, $OR^9$, a monovalent hydrocarbon group of 1 to 4 carbon atoms, a monovalent heterogenous group of 1 to 4 carbon atoms, a substituted monovalent hydrocarbon group of 1 to 4 carbon atoms, or a substituted monovalent heterogenous group of 1 to 4 carbon atoms, $R^{13}$ is not $N(R^9)(OR^9)$ when bond g is a single bond and $R^{13}$ is not $NOR^9$ when bond g is a double bond, and $R^{13}$ is not $OR^9$ when $R^{11}$ is $OR^9$; $M^1$, $M^2$, $M^3$, and $M^4$ are each carbon atoms, and $R^{12}$ is a hydrogen atom;

$R^{16}$ is selected from the group consisting of —$CH_2$—, —NH—, and —$NR^{19}$—, wherein $R^{19}$ is selected from the group consisting of hydrocarbon groups, substituted hydrocarbon groups, heterogenous groups, and substituted heterogenous groups; with the proviso that $R^{19}$ may optionally be bonded together with $R^8$ to form a ring structure selected from the group consisting of heterocyclic groups and substituted heterocyclic groups;

$R^{17}$ is selected from the group consisting of —$SO_2$—, C(O)—, and —$CH_2$—;

$R^{18}$ is selected from the group consisting of a sulfur atom and —$CH_2$—; and an optical isomer of the structure described above, a diastereomer of the structure, an enantiomer of the structure, a pharmaceutically-acceptable salt of the structure, a biohydrolyzable amide of the structure, a biohydrolyzable ester of the structure, and a biohydrolyzable imide of the structure; and (B) a carrier.

2. The composition of claim 1, wherein the carrier is selected from the group consisting of systemic and topical carriers.

3. The composition of claim 2, wherein the systemic carrier comprises one or more ingredients selected from the group consisting of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, and combinations thereof.

4. The composition of claim 2, wherein the topical carrier comprises one or more ingredients selected from the group consisting of water, alcohols, aloe vera gel, allantoin, glycerin, vitamin A and E oils, mineral oil, propylene glycol, PPG-2 myristyl propionate, dimethyl isosorbide, q) emollients, r) propellants, s) solvents, t) humectants, u) thickeners, v) powders, w) fragrances, x) pigments, y) sugars, z) cellulose or a derivative thereof, aa) a salt, bb) Edetate disodium, cc) a pH adjusting additive, and combinations thereof.

* * * * *

UNITED STATES PATENT AND TRADEMARK OFFICE
CERTIFICATE OF CORRECTION

PATENT NO. : 7,074,942 B2  Page 1 of 2
APPLICATION NO. : 11/035602
DATED : July 11, 2006
INVENTOR(S) : Mitchell Anthony deLong It is certified that error appears in the above-identified patent and that said Letters Patent is hereby corrected as shown below:

Column 58, Example 69, delete

"

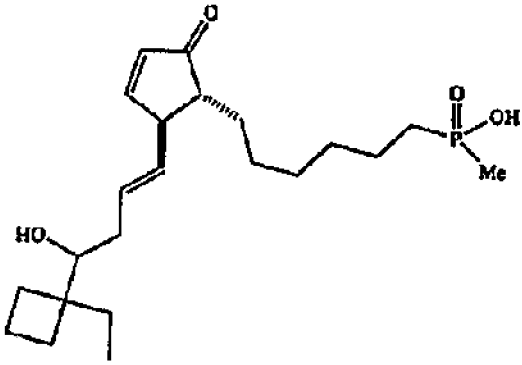

"

and insert therefor

--

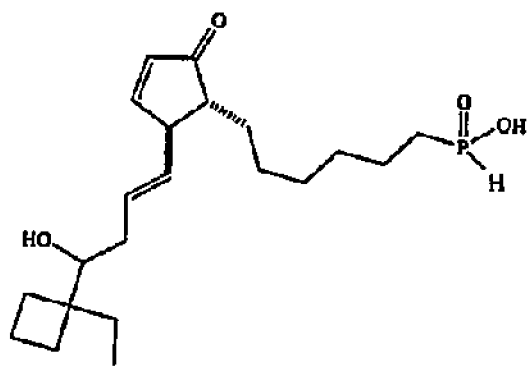

--

Column 63, line 2, insert --appropriate-- between the words "the" and "starting".

Column 70, Example 94, delete

"

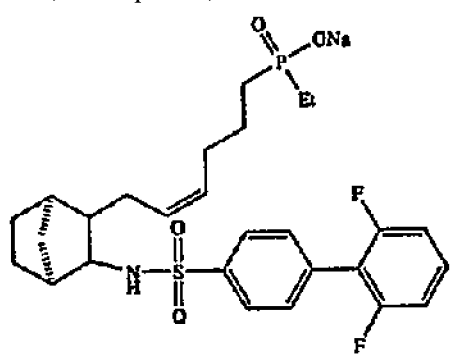

"

UNITED STATES PATENT AND TRADEMARK OFFICE
CERTIFICATE OF CORRECTION

PATENT NO. : 7,074,942 B2
APPLICATION NO. : 11/035602
DATED : July 11, 2006
INVENTOR(S) : Mitchell Anthony deLong It is certified that error appears in the above-identified patent and that said Letters Patent is hereby corrected as shown below:

Column 70, Example 94 (cont'd)
and insert therefor

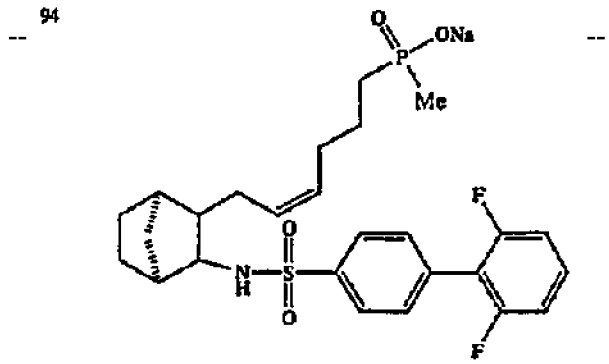

Signed and Sealed this

Tenth Day of April, 2007

JON W. DUDAS
*Director of the United States Patent and Trademark Office*